United States Patent
Kawada et al.

(10) Patent No.: US 9,416,189 B2
(45) Date of Patent: Aug. 16, 2016

(54) ANTI-CXADR ANTIBODY

(71) Applicants: MICROBIAL CHEMISTRY RESEARCH FOUNDATION, Tokyo (JP); MEDICAL & BIOLOGICAL LABORATORIES CO., LTD., Nagoya-shi, Aichi (JP)

(72) Inventors: Manabu Kawada, Tokyo (JP); Hiroyuki Inoue, Tokyo (JP); Shuichi Sakamoto, Tokyo (JP); Masunori Kajikawa, Komagane (JP); Masahito Sugiura, Komagane (JP); Sakiko Urano, Komagane (JP)

(73) Assignees: MICROBIAL CHEMISTRY RESEARCH FOUNDATION, Tokyo (JP); MEDICAL & BIOLOGICAL LABORATORIES CO., LTD., Aichi (JP)

( * ) Notice: Subject to any disclaimer, the term of this patent is extended or adjusted under 35 U.S.C. 154(b) by 8 days.

(21) Appl. No.: 14/400,207

(22) PCT Filed: May 13, 2013

(86) PCT No.: PCT/JP2013/063326
§ 371 (c)(1),
(2) Date: Nov. 10, 2014

(87) PCT Pub. No.: WO2013/168820
PCT Pub. Date: Nov. 14, 2013

(65) Prior Publication Data
US 2015/0140018 A1 May 21, 2015

(30) Foreign Application Priority Data
May 11, 2012 (JP) ................................ 2012-109902

(51) Int. Cl.
| | | |
|---|---|---|
| *C07K 16/30* | (2006.01) | |
| *G01N 33/574* | (2006.01) | |
| *A61K 39/395* | (2006.01) | |
| *C07K 16/28* | (2006.01) | |
| *A61K 39/00* | (2006.01) | |

(52) U.S. Cl.
CPC ............ *C07K 16/30* (2013.01); *C07K 16/2803* (2013.01); *C07K 16/3069* (2013.01); *G01N 33/57484* (2013.01); *G01N 33/57492* (2013.01); *A61K 39/00* (2013.01); *A61K 2039/505* (2013.01); *C07K 2317/34* (2013.01); *C07K 2317/732* (2013.01); *C07K 2317/734* (2013.01); *C07K 2317/76* (2013.01); *G01N 2333/705* (2013.01)

(58) Field of Classification Search
CPC . C07K 16/30; C07K 16/2803; C07K 16/3069
See application file for complete search history.

(56) References Cited

FOREIGN PATENT DOCUMENTS

JP 2005-304497 A 11/2005
WO 2009/100159 A2 8/2009

OTHER PUBLICATIONS

Almagro & Fransson, Frontiers in Bioscience 2008; 13:1619-33.*
Rudikoff et al., Proc. Nat'l Acad. Sci. USA 1982; 79:1979-83.*
Brown et al., J. Immunol. 1996; 156(9):3285-91.*
Reichert & Valge-Archer, Nat. Rev. Drug Disc. 2007; 6:349-356.*
E. A. Padlan, Adv Prot Chem 49:57-133; 1996.*
Corada et al., Blood, 2001; 97:1679-84.*
Martin et al., Clin. Exp. Med. 2005; 5:122-28.*
Korn et al. Cancer Gene Therapy 2006; 13:792-97.*
Anders et al., Br. J. Cancer 2009; 100:352-59.*
Kim et al., Br. J. Cancer 2003; 88:1411-16.*
Yamashita et al., Int. J. Cancer 2007; 121:1690-96.*
Veena et al., Lab Invest. 2009; 89:875-86.*
Tomko et al., Exp. Cell Res. 2000; 255:47-55.*
Patzke et al., J. Neurosci. 2010; 30(8):2897-910.*
International Preliminary report on Patentability dated Nov. 11, 2014, issued by the International Bureau of WIPO in counterpart International Application No. PCT/JP2013/063326.
Shaokai Jiang et al., "Solution structure of the coxsackievirus and adenovirus receptor domain 2", Protein Science 2007, pp. 539-542, vol. 16, No. 3.
Steven D. Carson, "Receptor for the group B coxsackieviruses and adenoviruses: CAR", Rev. Med. Virol. 2001, pp. 219-226, vol. 11, No. 4.
Katherine J.D.A. Excoffon et al., The Role of the Extracellular Domain in the Biology of the Coxsackievirus and Adenovirus Receptor, A, J. Respir. Cell Mol. Biol. 2005, pp. 498-503, vol. 32, No. 6.

(Continued)

*Primary Examiner* — Jessica H Roark
(74) *Attorney, Agent, or Firm* — Sughrue Mion, PLLC

(57) ABSTRACT

An object is to find a target molecule effective for cancer treatments and the like and to provide an antibody capable of specifically binding to the molecule, an anticancer agent comprising the antibody as an active ingredient, and so forth. Hence, prostate cancer cell lines (LNCaP-CR cells and LNCaP cells) were compared by SST-REX, and CXADR was identified as a molecule involved in tumor formation and so on. Then, a monoclonal antibody against CXADR was prepared, and the anti-cancer activity, ADCC activity, CDC activity, and so forth were examined. The result revealed that an antibody capable of binding to an epitope present at positions 181 to 230 of a CXADR protein derived from human exhibited an anti-cancer activity against prostate cancer cells, pancreatic cancer cells, and colorectal cancer cells. Further, it was also revealed that the antibody had an ADCC activity and a CDC activity. Moreover, the structures of light chain and heavy chain variable regions of the antibody were successfully determined.

7 Claims, 43 Drawing Sheets
(1 of 43 Drawing Sheet(s) Filed in Color)

(56) References Cited

OTHER PUBLICATIONS

Katherine J.D.A. Excoffon et al., "Functional Effects of Coxsackievirus and Adenovirus Receptor Glycosylation on Homophilic Adhesion and Adenoviral Infection", Journal of Virology, Jun. 2007, pp. 5573-5578, vol. 81, No. 11.

P. Freimuth et al., "The Coxsackievirus and Adenovirus Receptor", Curr. Top. Microbiol. Immunol. 2008, pp. 67-87, vol. 323.

Takatsugu Okegawa et al., "the Mechanism of the Growth-inhibitory Effect of Coxsackie and Adenovirus Receptor (CAR) on Human Bladder Cancer: A Functional Analysis of CAR Protein Structure", Cancer Res. 2001, pp. 6592-6600, vol. 61, No. 17.

International Search Report for PCT/JP2013/063326 dated Aug. 13, 2013.

Communication dated Nov. 27, 2015 from the European Patent Office issued in corresponding Application No. 13787178.6.

\* cited by examiner

Fig. 35

[BASE SEQUENCE OF HEAVY CHAIN OF ANTI-CXADR ANTIBODY CLONE 6G10A]

ATGGGATGGAGCTGTATCATCCTCTTTGTAGCAGCAGCTACAGGTGTCCACTCCAGTCCAACT
GCAGCAGCCTGGGCCTGAACTTGTGAAGCCTGGGGCCTCAGTGAAGATGTCCTGCAAGGCTTCTGG
CTACACTTTCACCAGTACTACTGGATAAACTGGGTGAAGCAGAGGCCTGGACAAGGCCTTGAGTGGATT
GGAAATATTTATCCTGGTAGTAGTACTAAGTACAATGAGAAGTTCAAGAGCAAGGCCACACTGA
CTGTAGACACATCCTCCAGACAATCCAGCCCACAGTGCAGCTGACAGCTCAGCCTGACGACTGCGGTC
TATTATTGTGCAAAGGGGATGGTACTACTTTGCTGACTGGGGCCAAGGGACTCTGGTCACTGTCT
CTGCA

[AMINO ACID SEQUENCE OF HEAVY CHAIN OF ANTI-CXADR ANTIBODY CLONE 6G10A]

<u>MGWSCIILSLVAAATG VHS</u>QVQLQQPGAELVKPGASVKLSCKASGYTFTS<u>YWIN</u>WVKQRPGQ
<SIGNAL SEQUENCE>                                       CDR1

GLEWIG<u>NIYPGSSSTKYNEKFKS</u>KATLTVDTSSSTAHMQLSSLTSDDSAVYYCAK<u>GDGDYFAD</u>
       CDR2                                              CDR3

WGQGTLVTVSA

Fig. 36

[BASE SEQUENCE OF LIGHT CHAIN OF ANTI-CXADR ANTIBODY CLONE 6G10A]

ATGAGTGTGCCCACTCAGCTCCTGGGGTTGCTGCTGCTGTGGCTTACAGATGCCAGATGTGACAT
CCAGATGACTCAGTCTCCAGCTTCCCTGTCTGCATCTGTGGGAGAAACTGTCACCATCACATGTC
GAGCAAGTGAGAATATTGACAGTTATTTAGCATGGTATCAGCAGAAACAGGGAAAATCTCCTCA
GCTCCTGGTCTATGCTGCAACACTCTTAGACATGGTGTGCCATCAAGGTTCAGTGGCAGTGGAT
CAGGCACACAGTATTCTCAAGATCAACAGCCTGCAGTCTGAAGATGTTGCGAGATATTACTGT
CAACATTATTATAGTACTCCGTGGACGTTCGGTGGAGGCACCAAGCTGGAAATCAAACGGGCT

[AMINO ACID SEQUENCE OF LIGHT CHAIN
OF ANTI-CXADR ANTIBODY CLONE 6G10A]

MSVPTQLLGLLLLWLTDARC DIQMTQSPASLSASVGETVTITCRASENIDSYLA

<SIGNAL SEQUENCE>                              CDR1

WYQQKQGKSPQLLVYAATLLADGVPSRFSGSGSGTQYSLKINSLQSEDVARYYC

CDR2

QHYYSTPWTFGGGTKLEIKRA

CDR3

Fig. 37

[BASE SEQUENCE OF HEAVY CHAIN OF ANTI-CXADR ANTIBODY CLONE 7F8A]

ATGAGAGTGTTGATTCTTGTGTACCTGTTGACAGCCCTTCCTGGTATCTTGTCTGATGTACAGTT
CAGGAGTCAGGACCTGGCCTGGTGAAGCCTTCTCAGACAGTGTCCCTCACTGTCACTGTCACTG
GCTACTCTATCACTGGTAATTGGTAATCACTGGTTGGATCGGCAGTTTCAGGAAGCAAACT
GGAGTGGATAGGTACATTAACTCCAGTGGTAGCACTGACAGCAATCCATCTCAAAAGTCGA
ATCTCATCACTAGAGACACTTCCAAGAACCAGTATTCCTGCAGTTGAACTCTGTGACAATTGA
AGATATAGCCACATATTACTGTGCAAGAGATGATTACTACTTTGACTACTGGGGCCAAGGCACCA
CTCTCACAGTCTCCTCA

[AMINO ACID SEQUENCE OF HEAVY CHAIN OF ANTI-CXADR ANTIBODY CLONE 7F8A]

MRVLILVYLLTALPGILSDVQLQESGPGLVKPSQTVSLTCTVTGYSIT<u>NGNHWWN</u>
       <SIGNAL SEQUENCE>                           CDR1

WIRQVSGSKLEWIGYINSSGTDSNPSLKSRISITRDTSKNQLFLQLNSVTIEDIATYYCAR
                      CDR2

<u>DDYEDY</u>WGQGTTLTVSS
 CDR3

Fig. 38

[BASE SEQUENCE OF LIGHT CHAIN OF ANTI-CXADR ANTIBODY CLONE 7F8A]

ATGAGTGTGCCCACTCAGCTCCTGGGGTTGCTGCTGTGGCTTACAGATGCCAGAT
GTGACATCCAGATGACTCAGTCTCCAGCTTCCCTGTCTGTGGGAGAAACTGT
CACCATCACATGTCGAGCAAGTGAGAATATTGACAGTTATTAGCATGTATCAGCAG
AAACAGGGAAAATCTCCTCAGCTCCTGGTCTATGCTGCAACACTCTTAGACAGATGGTG
TGCCATCAAGGTTCAGTGGCAGTGGATCAGGCACACAGTATTCTCAAGATCAACA
GCCTGCAGTCTGAAGATGTTGCAGATATTACTGTCAACATTATTAGTACTCCACTC
AGTTCGGGTGCTGGGACCAAGCTGGAGCTGAAACGGGCT

[AMINO ACID SEQUENCE OF LIGHT CHAIN OF ANTI-CXADR ANTIBODY CLONE 7F8A]

<u>MSVPTQLLGLLLLWLTDAR</u>CDIQMTQSPASLSASVGETVTITC<u>RASENIDSYLA</u>
<SIGNAL SEQUENCE>                                   CDR1

WYQQKQGKSPQLLVY<u>AATLLAD</u>GVPSRFSGSGSGTQYSLKINSLQSEDVARYYC
              CDR2

<u>QHYYSTPLT</u>FGAGTKLELKRA
CDR3

ANTI-CXADR ANTIBODY

CROSS REFERENCE TO RELATED APPLICATIONS

This application is a National Stage of International Application No. PCT/JP2013/063326 filed May 13, 2013, claiming priority based on Japanese Patent Application No. 2012-109902 filed May 11, 2012, the contents of all of which are incorporated herein by reference in their entirety.

TECHNICAL FIELD

The present invention relates to an anti-CXADR antibody, and more specifically relates to an antibody capable of binding to an epitope present at positions 181 to 230 of a CXADR protein derived from human, and a pharmaceutical composition and a testing agent which comprise the antibody as an active ingredient. Moreover, the present invention relates to: a method for determining effectiveness of a cancer treatment using the antibody for a patient on the basis of the presence or absence of a CXADR protein; a method for treating a cancer by administering the antibody to the patient for whom the effectiveness is determined to be high by the determination method; and a cancer treatment agent comprising the antibody as an active ingredient, which is administered to the patient.

BACKGROUND ART

Cancers in addition to coronary artery disease are the main cause of death in developed countries, and the proportion of cancers is increasing steadily year by year. Moreover, among cancers, lung cancer, prostate cancer, pancreatic cancer, breast cancer, colon cancer, and ovarian cancer are typical causes of cancer death. Particularly, prostate cancer is the fourth prevalent cancer spreading in males worldwide. The development of the cancer is observed in approximately 20% of males in Europe and the United States. Furthermore, prostate cancer accounts for approximately 3.5% of deceased patients due to cancers in Japan, and as a recent trend, the proportion is rapidly increasing.

In addition, surgical resection, radiation therapy, hormonal therapy, and chemotherapy are given as the main treatment methods against prostate cancer and the like. Nevertheless, the effects of these treatment methods are small for many people. Hence, an effective treatment method has not been established against cancers yet at present.

Under such circumstances, the use of an antibody as an anticancer agent has drawn attention recently. The importance is increasingly recognized as an approach in treating various disease conditions (of cancer types). For example, in a case of an antibody targeting a tumor-specific antigen, the administered antibody is assumed to accumulate at the tumor. Accordingly, attack on cancer cells by an immune system through a complement-dependent cytotoxicity (CDC) activity or an antibody-dependent cell-mediated cytotoxicity (ADCC) activity can be expected. Moreover, by binding a drug such as a radionuclide or cytotoxic substance to an antibody in advance, the bound drug can be efficiently delivered to the tumor site. Thereby, the amount of the drug reaching to other tissues can be reduced, and consequently a reduction in side effect can be expected. By administering an antibody having an agonistic activity in a case where a tumor-specific antigen has an activity to induce cell death, or by administering an antibody having a neutralizing activity in a case where a tumor-specific antigen is involved in cell growth and survival, termination or shrinkage of tumor growth can be expected from the accumulation of the tumor-specific antibody and the activity of the antibody. Because of such abilities, it is thought that an antibody is suitably applied as an anticancer agent.

As antibody drugs having been put on the market so far for leukemia and lymphoma, rituximab (product name: Rituxan) and inotuzumabozogamicin (product name: Zevailn) targeting CD20, gemtuzumab ozogamicin (product name: Mylotarg) targeting CD33, and so forth have been developed. Further, against epithelial solid cancer such as breast cancer, trastuzumab (product name: Herceptin) targeting Her2/neu, bevacizumab (product name: Avastin) targeting VEGF, and so forth have been developed.

However, the number of antibody drugs approved by 2008 is approximately 20 in the United States and approximately 10 in Japan. Particularly, against solid cancers, only few antibody drugs are effective. Hence, further development of effective antibody drugs is desired, and it is strongly desired to identify particularly target molecules (antigen, epitope) that greatly influence the effectiveness of antibody drugs.

Meanwhile, as a protein involved in infections by coxsackieviruses and the like, coxsackievirus and adenovirus receptor (CXADR) is known. In addition, regarding this protein, it has been reported that the expression is promoted in ovarian cancer and skin basal cell carcinoma (PTL 1). On the other hand, a homozygous deletion of CXADR has been observed in cholangiocarcinoma, suggesting that CXADR functions as a tumor suppressor gene (PTL 2).

Although there are reports about the association between CXADR and cancer as described above, whether CXADR contributes to the development, malignant transformation, and the like of a cancer, or functions in a suppressive manner is not confirmed at present. Thus, it is still unknown whether an antibody against CXADR can have an anti-cancer activity.

CITATION LIST

Patent Literatures

[PTL 1] International Publication No. WO2009/100159
[PTL 2] Japanese Unexamined Patent Application Publication No. 2005-304497

SUMMARY OF INVENTION

Technical Problem

The present invention has been made in view of the above-described problems of the conventional techniques. An object of the present invention is to find a target molecule effective for cancer treatments and the like, and to provide an antibody capable of specifically binding to the molecule, and thus a pharmaceutical composition comprising the antibody as an active ingredient.

Solution to Problem

A human androgen-dependent prostate cancer cell line LNCaP has a low tumorigenicity in immunodeficient mice, and the application as a xenograft in animal experiments is difficult. On the other hand, the present inventors had established a LNCaP cell subline: LNCaP-CR. LNCaP-CR has a quite high tumorigenicity in immunodeficient mice, and is useful as a xenograft model of human androgen-dependent prostate cancer cells (see "Kawada, M. et al., Cancer Lett., 2006, vol. 242, pp. 46 to 52," "Kawada, M. et al., Cancer Sci., 2007, vol. 98, pp. 350 to 356").

Then, the present inventors thought that a factor involved in malignant progression of cancer might be found by comparing a membrane protein and a secretory protein expressed in LNCaP-CR cells with those expressed in its parental line LNCaP cells. Thus, the inventors carried out a signal sequence trap (SST-REX) method, a technique for specifically isolating and identifying membrane proteins and secretory proteins. As a result, CXADR was successfully identified as a protein which was not expressed in LNCaP cells but was expressed in LNCaP-CR cells.

Next, the present inventors prepared a monoclonal antibody against this protein, and examined the binding to various cancer cell lines, the in vitro and in vivo anti-cancer activities, the ADCC activity, and the CDC activity. As a result, it was found that an antibody capable of binding to an epitope present at positions 181 to 230 of the CXADR protein derived from human had an excellent anti-cancer activity in mice into which the LNCaP-CR cells had been transplanted, particularly mice having the LNCaP-CR cells transplanted orthotopically, i.e., to the prostate. Moreover, it was also found that the antibody exhibited the anti-cancer activity against not only prostate cancer but also pancreatic cancer and colorectal cancer. Further, it was verified that such an effect of suppressing cancers in vivo was demonstrated when the antibody bound to CXADR, in other words, the antibody was capable of demonstrating the effect of suppressing a cancer expressing the CXADR protein. Additionally, it was also revealed that the antibody had an ADCC activity and a CDC activity. Furthermore, the present inventors successfully determined structures of light chain and heavy chain variable regions of the antibody, and thus completed the present invention.

Specifically, the present invention relates to an antibody capable of binding to an epitope present at positions 181 to 230 of a CXADR protein derived from human, and a pharmaceutical composition and so forth which comprise the antibody as an active ingredient. More specifically, the present invention provides the followings.
(1) An antibody capable of binding to an epitope present at positions 181 to 230 of a CXADR protein derived from human.
(2) The antibody according to (1) having any one of the following features (a) to (d):
  (a) comprising
    a light chain variable region including amino acid sequences of SEQ ID NOs: 1 to 3 or the amino acid sequences in at least any one of which one or more amino acids are substituted, deleted, added, and/or inserted, and
    a heavy chain variable region including amino acid sequences of SEQ ID NOs: 6 to 8 or the amino acid sequences in at least any one of which one or more amino acids are substituted, deleted, added, and/or inserted;
  (b) comprising
    a light chain variable region including an amino acid sequence of SEQ ID NO: 5, the amino acid sequence from which a signal sequence is removed, or at least any one of these amino acid sequences in which one or more amino acids are substituted, deleted, added, and/or inserted, and
    a heavy chain variable region including an amino acid sequence of SEQ ID NO: 10, the amino acid sequence from which a signal sequence is removed, or at least any one of these amino acid sequences in which one or more amino acids are substituted, deleted, added, and/or inserted;
  (c) comprising
    a light chain variable region including amino acid sequences of SEQ ID NOs: 11 to 13 or the amino acid sequences in at least any one of which one or more amino acids are substituted, deleted, added, and/or inserted, and
    a heavy chain variable region including amino acid sequences of SEQ ID NOs: 16 to 18 or the amino acid sequences in at least any one of which one or more amino acids are substituted, deleted, added, and/or inserted; and
  (d) comprising
    a light chain variable region including an amino acid sequence of SEQ ID NO: 15, the amino acid sequence from which a signal sequence is removed, or at least any one of these amino acid sequences in which one or more amino acids are substituted, deleted, added, and/or inserted, and
    a heavy chain variable region including an amino acid sequence of SEQ ID NO: 20, the amino acid sequence from which a signal sequence is removed, or at least any one of these amino acid sequences in which one or more amino acids are substituted, deleted, added, and/or inserted.
(3) A pharmaceutical composition comprising the antibody according to any one of (1) and (2) as an active ingredient.
(4) An agent for testing a disease associated with a CXADR protein, the agent comprising the antibody according to any one of (1) and (2) as an active ingredient.
(5) A method for determining effectiveness of a cancer treatment, the method comprising a step of detecting the presence or absence of a CXADR protein in a sample isolated from a patient, wherein if the presence of the CXADR protein is detected in the step, it is determined that the effectiveness of the cancer treatment using a cancer treatment agent comprising the antibody according to any one of (1) and (2) as an active ingredient is high for the patient.
(6) A cancer treatment agent comprising the antibody according to any one of (1) and (2) as an active ingredient, which is administered to the patient for whom the effectiveness is determined to be high by the method according to (5).
(7) A method for treating a cancer, comprising administering a cancer treatment agent comprising the antibody according to any one of (1) and (2) as an active ingredient to the patient for whom the effectiveness is determined to be high by the method according to (5).

Advantageous Effects of Invention

The present invention provides an antibody capable of binding to a CXADR protein derived from human, the antibody having excellent in vivo anti-cancer activity and so forth. The antibody of the present invention makes it possible to treat, prevent, and test a disease associated with the CXADR protein. Particularly, the antibody of the present invention is effective against cancers (such as prostate cancer, pancreatic cancer, and colorectal cancer).

BRIEF DESCRIPTION OF DRAWINGS

The patent or application file contains at least one drawing executed in color. Copies of this patent or patent application publication with color drawings will be provided by the Office upon request and payment of the necessary fee.

FIG. 35 is a figure showing a base sequence (SEQ ID NO:4) and an amino acid sequence (SEQ ID NO:5) of a heavy chain variable region of the anti-CXADR antibody produced from the hybridoma (clone name: 6G10A). In the figure, amino acid sequences which are underlined indicate amino acid sequences of predicted signal sequence and CDRs 1 to 3.

FIG. 36 is a figure showing a base sequence (SEQ ID NO:9) and an amino acid sequence (SEQ ID NO:10) of a light chain variable region of the anti-CXADR antibody produced from the hybridoma (clone name: 6G10A). In the figure, amino acid sequences which are underlined indicate amino acid sequences of predicted signal sequence and CDRs 1 to 3.

FIG. 37 is a figure showing a base sequence (SEQ ID NO:11) and an amino acid sequence (SEQ ID NO:12) of a heavy chain variable region of the anti-CXADR antibody produced from the hybridoma (clone name: 7F8A). In the figure, amino acid sequences which are underlined indicate amino acid sequences of predicted signal sequence and CDRs 1 to 3.

FIG. 38 is a figure showing a base sequence (SEQ ID NO:19) and an amino acid sequence (SEQ ID NO:20) of a light chain variable region of the anti-CXADR antibody produced from the hybridoma (clone name: 7F8A). In the figure, amino acid sequences which are underlined indicate amino acid sequences of predicted signal sequence and CDRs 1 to 3.

DESCRIPTION OF EMBODIMENTS

Figure 1:
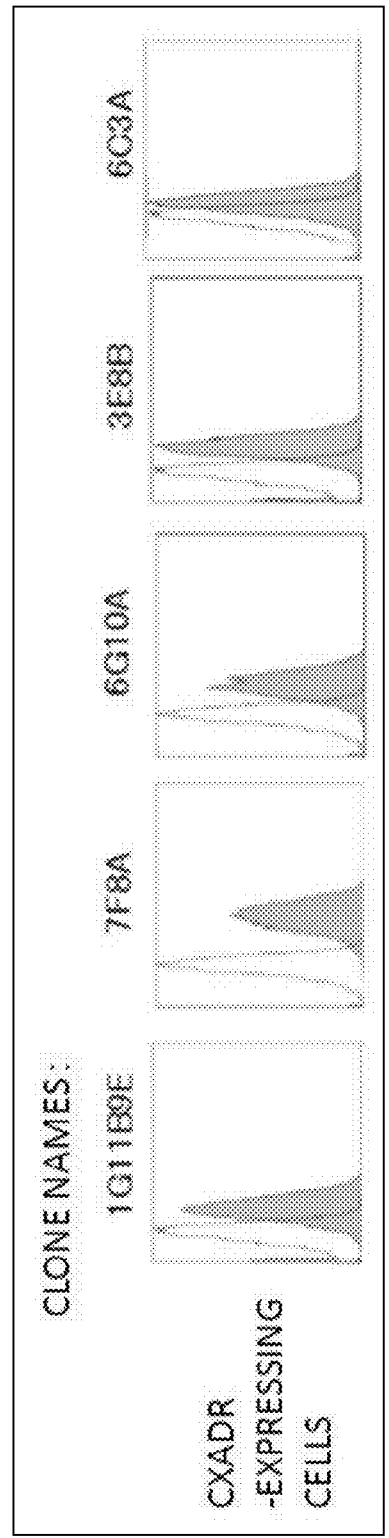
FIG. 1 shows graphs for illustrating the result of analyzing with a flow cytometer the reactivity between CXADR-expressing cells and each of anti-CXADR antibodies produced from hybridomas (clone names: 1G11B9E, 7F8A, 6G10A, 3E8B, 6C3A). A filled histogram part in each flow cytometer data illustrates the reaction with the anti-CXADR antibody produced from the corresponding hybridoma, whereas a white histogram part illustrates a reaction with a negative control mouse IgG (mixture of isotype control antibodies) (The same applies to FIG. 2).

As described in Examples later, it has been revealed that an antibody capable of binding to a specific site (positions 181 to 230) of a CXADR protein derived from human has an ADCC (antibody-dependent cell-mediated cytotoxicity) activity and so forth and exhibits an excellent anti-cancer activity. Thus, the present invention provides an antibody capable of binding to an epitope present at positions 181 to 230 of a CXADR protein derived from human.

In the present invention, the term "antibody" includes all classes and subclasses of immunoglobulins. An "antibody" includes a polyclonal antibody and a monoclonal antibody, and is also meant to include the form of a functional fragment of an antibody. A "polyclonal antibody" is an antibody preparation including different antibodies against different epitopes. Meanwhile, a "monoclonal antibody" means an antibody (including an antibody fragment) obtained from a substantially uniform antibody population. In contrast to a polyclonal antibody, a monoclonal antibody recognizes a single determinant on an antigen. The antibody of the present invention is preferably a monoclonal antibody. The antibody of the present invention is an antibody separated and/or recovered (i.e., isolated) from components in a natural environment.

In the present invention, "CXADR" is a protein also called "coxsackievirus and adenovirus receptor", "CAR", "CVB3 binding protein", or "coxsackievirus B receptor". The CXADR protein derived from human is typically a protein specified under RefSeq ID: NP_001329 (the protein is encoded by a base sequence specified under RefSeq ID: NM_001338). Thus, the "positions 181 to 230 of a CXADR protein derived from human" is typically an amino acid sequence from position 181 (serine residue) to position 230 (valine residue) of the protein specified under RefSeq ID: NP_001329.

In addition, the "positions 181 to 230 of a CXADR protein derived from human" may exist in a form having some amino acid naturally mutated, besides one having a typical amino acid sequence as described above. Thus, the "positions 181 to 230 of a CXADR protein derived from human" according to the present invention is preferably an amino acid sequence at the positions 181 to 230 of the protein specified under RefSeq ID: NP_001329, but further includes the amino acid sequence of the positions 181 to 230 of the protein specified under RefSeq ID: NP_001329 in which one or more amino acids are substituted, deleted, inserted, or added. Generally, 10 amino acids or less (for example, 5 amino acids or less, 3 amino acids or less, 1 amino acid) in the amino acid sequence are substituted, deleted, inserted, or added.

In the present invention, the term "epitope" means an antigenic determinant present in an antigen, that is, a site on an antigen where an antigen-binding domain in the antibody binds. Thus, the epitope in the present invention may be a polypeptide (linear epitope) having several consecutive amino acids in a primary sequence of amino acids, or may be a polypeptide (discontinuous epitope, conformational epitope) formed of amino acids which are not next to each other in the primary sequence of the amino acids, but which come near each other in a three-dimensional conformation by folding or the like of a peptide or protein. Moreover, such an epitope typically has at least 3 amino acids, most usually at least 5 amino acids (for example, 8 to 10, 6 to 20).

In the present invention, the term "anti-cancer activity" means an activity to suppress the growth of cancer cells and/or an activity to induce cancer cells to die. An anti-cancer activity can be evaluated, for example, according to an analysis using a tumor bearing model (such as cancer cell-transplanted mice) as described in Examples later. A preferable embodiment of the antibody of the present invention is an antibody capable of reducing the weight of a tumor to be excised in comparison with a control by 20% or more (for example, 25% or more, 30% or more, 35% or more, 40% or more, 45% or more, 50% or more, 55% or more, 60% or more), 21 days after a cancer cell line transplantation, according to an analysis described in Examples 4 and 5 later using mice into which a human androgen-dependent prostate cancer cell line: LNCaP-CR has been heterotopically (subcutaneously) transplanted. Another preferable embodiment of the antibody of the present invention is an antibody capable of reducing the weight of a tumor to be excised in comparison with a control by 70% or more (for example, 75% or more, 80% or more, 85% or more, 90% or more), 21 days after the cancer cell line transplantation, according to an analysis using mice into which LNCaP-CR has been transplanted orthotopically (i.e., in the prostate). Another preferable embodiment of the antibody of the present invention is an antibody capable of reducing the weight of a tumor to be excised in comparison with a control by 20% or more (for example, 25% or more, 30% or more, 35% or more, 40% or more, 45% or more, 50% or more, 55% or more, 60% or more), 21 days after the cancer cell line transplantation, according to an analysis using mice into which a human androgen-independent prostate cancer cell line: DU-145 has been heterotopically (subcutaneously) transplanted. Another preferable embodiment of the antibody of the present invention is an antibody capable of reducing the weight of a tumor to be excised in comparison with a control by 10% or more (for example, 15% or more, 20% or more, 25% or more), 21 days after the cancer cell line transplantation, according to an analysis using mice into which a pancreatic cancer cell line: BxPC-3 has been heterotopically (subcutaneously) transplanted. Another preferable embodiment of the antibody of the present invention is an antibody capable of reducing the weight of a tumor to be excised in comparison with a control by 10% or more (for example, 15% or more, 20% or more, 25% or more), 21 days after the cancer cell line transplantation, according to an analysis using mice into which a colorectal cancer cell line: DLD-1 has been heterotopically (subcutaneously) transplanted. Another preferable embodiment of the antibody of the present invention is an antibody capable of exhibiting an ADCC activity and/or a CDC activity against cancer cells.

Moreover, when used as an anticancer agent, these antibodies preferably further have a characteristic of not reducing the weight of an administration target. In addition, in order to allow the route of administration such as intravenous administration, these antibodies preferably further have a characteristic of not binding to vascular endothelial cells. The antibody of the present invention particularly preferably has multiple activities mentioned above in combination.

Other preferable embodiments of the antibody of the present invention are:
an antibody comprising
a light chain variable region including light chain CDR1 to CDR3 (amino acid sequences of SEQ ID NOs: 1 to 3), and
a heavy chain variable region including heavy chain CDR1 to CDR3 (amino acid sequences of SEQ ID NOs: 6 to 8); and
an antibody comprising
a light chain variable region including light chain CDR1 to CDR3 (amino acid sequences of SEQ ID NOs: 11 to 13), and
a heavy chain variable region including heavy chain CDR1 to CDR3 (amino acid sequences of SEQ ID NOs: 16 to 18).

Examples of other preferable embodiments of the antibody of the present invention include:
an antibody comprising
a light chain variable region having an amino acid sequence of SEQ ID NO: 5 (or the amino acid sequence from which a signal sequence is removed), and
a heavy chain variable region having an amino acid sequence of SEQ ID NO: 10 (or the amino acid sequence from which a signal sequence is removed); and
an antibody comprising
a light chain variable region having an amino acid sequence of SEQ ID NO: 15 (or the amino acid sequence from which a signal sequence is removed), and
a heavy chain variable region having an amino acid sequence of SEQ ID NO: 20 (or the amino acid sequence from which a signal sequence is removed).

Moreover, among these, from the viewpoints of having a higher anti-cancer activity and having a characteristic of not binding to vascular endothelial cells, more preferable as the antibody of the present invention is an antibody comprising
a light chain variable region including light chain CDR1 to CDR3 (amino acid sequences of SEQ ID NOs: 1 to 3), and
a heavy chain variable region including heavy chain CDR1 to CDR3 (amino acid sequences of SEQ ID NOs: 6 to 8); and particularly preferable as the antibody of the present invention is an antibody comprising
a light chain variable region having an amino acid sequence of SEQ ID NO: 5 (or the amino acid sequence from which a signal sequence is removed), and
a heavy chain variable region having an amino acid sequence of SEQ ID NO: 10 (or the amino acid sequence from which a signal sequence is removed).

Once the antibody comprising the light chain variable region and the heavy chain variable region is obtained, those skilled in the art can prepare various antibodies capable of binding to a peptide region (epitope) specified on the positions 181 to 230 of the human-derived CXADR protein recognized by the antibody, and also capable of exhibiting an anti-cancer activity. The epitope of the antibody can be determined by well-known methods such as checking binding to an overlapping synthetic oligopeptide obtained from the amino acid sequence of the CXADR protein derived from human (for example, Ed Harlow and D. Lane, Using Antibodies, a Laboratory Manual, Cold Spring Harbor Laboratory Press, U.S. Pat. No. 4,708,871). A peptide library in phage display can also be used for the epitope mapping. Whether two antibodies bind to the same epitope or sterically overlapping epitopes can be determined by a competitive assay method.

The antibody of the present invention includes a mouse antibody, a chimeric antibody, a humanized antibody, a human antibody, and a functional fragment of these antibodies. In a case where the antibody of the present invention is administered as a drug to a human, a chimeric antibody, a humanized antibody, or a human antibody is desirable from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Specifically, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. Nos. 4,816,397, 4,816,567, and 5,807, 715). Moreover, in the present invention, a "humanized antibody" is an antibody obtained by grafting (CDR grafting) a gene sequence of an antigen-binding site (CDR) of a non-human-derived antibody onto a human antibody gene. The preparation methods are known (see, for example, EP239400, EP125023, WO90/07861, WO96/02576). In the present invention, a "human antibody" is an antibody, all regions of which are derived from human. In preparing a human antibody, it is possible to utilize a screening method for a production of an antibody having a higher activity than human B cells, a phage display method, a transgenic animal (for example, a mouse) capable of producing a repertoire of the human antibody by immunization. Preparation methods for a human antibody are known (for example, Nature, 362:255-258 (1993), Intern. Rev. Immunol, 13: 65-93 (1995), J. Mol. Biol, 222: 581-597 (1991), Nature Genetics, 15: 146-156 (1997), Proc. Natl. Acad. Sci. USA, 97. 722-727 (2000), Japanese Unexamined Patent Application Publication Nos. Hei 10-146194 and Hei 10-155492, Japanese Patent No. 2938569, Japanese Unexamined Patent Application Publication No. Hei 11-206387, International Application Japanese-Phase Publication Nos. Hei 8-509612 and Hei 11-505107).

In the present invention, a "functional fragment" of an antibody means a part (partial fragment) of an antibody, which specifically recognizes the epitope present at the positions 181 to 230 of the CXADR protein derived from human.

Specific examples thereof include Fab, Fab', F(ab') 2, a variable region fragment (Fv), a disulfide bonded Fv, a single chain Fv (scFv), a sc (Fv) 2, a diabody, a polyspecific antibody, polymers thereof, and the like.

Here, "Fab" means a monovalent antigen-binding fragment, of an immunoglobulin, composed of a part of one light chain and a part of one heavy chain. Fab can be obtained by papain digestion of an antibody or by a recombinant method. "Fab'" is different from Fab in that a small number of residues are added to the carboxy terminus of a heavy chain CH1 domain including one or more cysteines from an antibody hinge region. "F(ab') 2" means a bivalent antigen-binding fragment, of an immunoglobulin, composed of parts of both light chains and parts of both heavy chains.

A "variable region fragment (Fv)" is a smallest antibody fragment having complete antigen recognition and binding sites. An Fv is a dimer in which a heavy chain variable region and a light chain variable region are strongly linked by non-covalent bonding. A "single chain Fv (scFv)" includes a heavy chain variable region and a light chain variable region of an antibody, and these regions exist in a single polypeptide chain. A "sc (Fv) 2" is a single chain obtained by linking two heavy chain variable regions and two light chain variable regions with a linker or the like. A "diabody" is a small antibody fragment having two antigen-binding sites. This fragment includes a heavy chain variable region linked to a light chain variable region in a single polypeptide chain. Each region forms a pair with a complementary region in another chain. A "polyspecific antibody" is a monoclonal antibody having a binding specificity to at least two different antigens. For example, a polyspecific antibody can be prepared by coexpression of two immunoglobulin heavy chain/light chain pairs in which two heavy chains have different specificities.

The present invention provides a peptide comprising a light chain or a heavy chain of an antibody comprising a CDR identified in the present invention, or a variable region of these chains. Preferable peptides are:

a peptide comprising the light chain or the variable region of the antibody of the present invention having the amino acid sequences of SEQ ID NOs: 1 to 3;

a peptide comprising the light chain or the variable region of the antibody of the present invention having the amino acid sequences of SEQ ID NOs: 11 to 13;

a peptide having the amino acid sequence of SEQ ID NO: 5 or the amino acid sequence from which a signal sequence is removed; and a peptide having the amino acid sequence of SEQ ID NO: 15 or the amino acid sequence from which a signal sequence is removed.

Other preferable peptides are:

a peptide comprising the heavy chain or the variable region of the antibody of the present invention having the amino acid sequences of SEQ ID NOs: 6 to 8;

a peptide comprising the heavy chain or the variable region of the antibody of the present invention having the amino acid sequences of SEQ ID NOs: 16 to 18;

a peptide having the amino acid sequence of SEQ ID NO: 10 or the amino acid sequence from which a signal sequence is removed; and a peptide having the amino acid sequence of SEQ ID NO: 20 or the amino acid sequence from which a signal sequence is removed.

In addition, by linking these peptides, for example, with a linker or the like, a functional antibody can be prepared.

The antibody of the present invention includes antibodies whose amino acid sequences are modified without impairing desirable activities (binding activity to an antigen, anti-cancer activity, and/or other biological properties). An amino acid sequence mutant of the antibody of the present invention can be prepared by introduction of a mutation into a DNA encoding an antibody chain of the present invention or by peptide synthesis. Examples of such a modification include substitution, deletion, addition, and/or insertion of a residue in the amino acid sequence of the antibody of the present invention. A site where the amino acid sequence of the antibody is modified may be a constant region of the heavy chain or the light chain of the antibody or a variable region (framework region and CDR) thereof, as long as the resulting antibody has activities equivalent to those before the modification. It is conceivable that modification on an amino acid other than CDR has a relatively small influence on binding affinity for an antigen. As of now, there are known screening methods for an antibody whose affinity for an antigen has been enhanced by modifying an amino acid of CDR (PNAS 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

Moreover, now, an antibody whose affinity for an antigen has been enhanced can also be monitored by utilizing an integrated computing chemical system or the like (for example, Molecular Operating Environment, manufactured by CCG Inc. in Canada) (see, for example, www.rsi.co.jp/kagaku/cs/ccg/products/application/protein.html).

The number of amino acids modified is preferably 10 amino acids or less, more preferably 5 amino acids or less, and most preferably 3 amino acids (for example, 2 amino acids or less, 1 amino acid). The modification of amino acids is preferably conservative substitution. In the present invention, the term "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), amino acids containing sulfur (cysteine, methionine), amino acids having an amide group (asparagine, glutamine), an amino acid having an imino group (proline), and amino acids having an aromatic group (phenylalanine, tyrosine, tryptophan). Meanwhile, "having equivalent activities" or similar phrases mean the binding activity to an antigen or the anti-cancer activity is equivalent (for example, 70% or more, preferably 80% or more, more preferably 90% or more) to that of a target antibody (typically, an anti-CXADR antibody 6G10A, an anti-CXADR antibody 7F8A). The binding activity to an antigen can be evaluated, for example, by preparing Ba/F3 cells expressing an antigen, and analyzing the reactivity with an antibody sample with a flow cytometer (Example 2). Moreover, the anti-cancer activity can be evaluated as described above by the analysis using the tumor bearing model (Example 4 and so forth).

Further, the modification on the antibody of the present invention may be a modification on post-translational process of the antibody such as, for example, alternation of the number or position of the glycosylation sites. Thereby, for example, the ADCC activity of the antibody can be improved. Glycosylation of the antibody is typically N-linked or O-linked glycosylation. The glycosylation of the antibody largely depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. Nos. 5,047,335, 5,510,261, and 5,278,299, International Publication No. WO99/54342). Furthermore, in the present invention, for the purpose of increasing the stability of the antibody or other purposes, an amino acid subjected to deamidation or an amino acid next to the amino acid subjected to the deamidation may be substituted with a different amino acid to suppress the deamidation. Alternatively, the stability of the antibody can also be increased by substituting glutamic acid with a different amino acid. The present invention also provides an antibody thus stabilized.

If the antibody of the present invention is a polyclonal antibody, the polyclonal antibody can be obtained as follows. Specifically, an animal to be immunized is immunized with an antigen (a polypeptide having the amino acid sequence of the positions 181 to 230 of the CXADR protein derived from human, a partial peptide thereof, cells expressing these, or the like). An antiserum from the animal is purified by conventional means (for example, salting-out, centrifugation, dialysis, column chromatography, or the like) to obtain the polyclonal antibody. Meanwhile, a monoclonal antibody can be prepared by a hybridoma method or a recombinant DNA method.

The hybridoma method is typically a method by Kohler and Milstein (Kohler & Milstein, Nature, 256: 495 (1975)). Antibody-producing cells used in the cell fusion process of this method are spleen cells, lymph node cells, peripheral blood leukocytes, or the like of an animal (for example, mouse, rat, hamster, rabbit, monkey, goat) immunized with an antigen (a polypeptide having the amino acid sequence of the positions 181 to 230 of the CXADR protein derived from human, a partial peptide thereof, cells expressing these, or the like). It is also possible to use antibody-producing cells obtained by causing the antigen to act, in a medium, on the above-described types of cells, lymphocytes, or the like, which are isolated from non-immunized animals in advance. As myeloma cells, various known cell lines can be used. The antibody-producing cells and the myeloma cells may be ones originated from different animal species, as long as they can be fused. However, the antibody-producing cells and the myeloma cells are preferably originated from the same animal species. Hybridomas can be produced, for example, by cell fusion between mouse myeloma cells and spleen cells obtained from a mouse immunized with the antigen. By the subsequent screening, a hybridoma which produces a monoclonal antibody specific to the CXADR protein derived from human can be obtained. The monoclonal antibody against the CXADR protein derived from human can be obtained by culturing the hybridoma, or from the ascites of a mammal to which the hybridoma is administered.

The recombinant DNA method is a method by which the antibody of the present invention is produced as a recombinant antibody as follows. A DNA encoding the antibody of the present invention or a peptide thereof is cloned from a hybridoma, B cells, or the like. The cloned DNA is incorporated into an appropriate vector, which is introduced into host cells (for example, a mammalian cell line, *Escherichia coli*, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)). For the expression of the DNA encoding the antibody of the present invention, DNAs encoding a heavy chain and a light chain may be incorporated into expression vectors, respectively, to transform the host cells. Alternatively, DNAs encoding a heavy chain and a light chain may be incorporated into a single expression vector to transform the host cells (see International Publication No. WO94/11523). The antibody of the present invention can be obtained in a substantially pure and homogeneous form by culturing the host cells, followed by separation and purification from the host cells or the culture solution. For the separation and purification of the antibody, normal methods used for polypeptide purification can be employed. When a transgenic animal (cattle, goat, sheep, pig, or the like) incorporating the antibody gene is prepared using a transgenic animal production technique, a large amount of monoclonal antibodies derived from the antibody gene can also be obtained from milk of the transgenic animal.

The present invention can also provide: a DNA encoding the antibody or peptide of the present invention; a vector comprising the DNA; host cells comprising the DNA; and a method for producing the antibody, comprising culturing the host cells and recovering the antibody.

As described in Examples later, the antibody of the present invention exhibits the anti-cancer activity and so forth by inhibiting a function of the CXADR protein. Accordingly, the antibody of the present invention can be used to treat or prevent a disease associated with the CXADR protein. Thus, the present invention provides: a pharmaceutical composition comprising the antibody of the present invention as an active ingredient (for example, a cancer treatment agent comprising the antibody of the present invention as an active ingredient); and a method for treating or preventing a disease (for example, a cancer) associated with a CXADR protein, the method comprising a step of administering a therapeutically or preventively effective amount of the antibody of the present invention to a mammal including a human. The treatment or prevention method of the present invention is applicable to various mammals, other than human, including, for example, dogs, cats, cattle, horses, sheep, pigs, goats, rabbits, and the like.

The disease associated with the CXADR protein targeted by the antibody of the present invention should be a disease, in the development, the progression of the symptom, the exacerbation, and so forth of which the CXADR protein is involved. Examples of the disease include cancers and infectious diseases (such as coxsackievirus infection, adenovirus infection). Desirably, the disease is a cancer.

In addition, the cancer targeted by the antibody of the present invention is not particularly limited, as long as the antibody of the present invention can exhibit an anti-cancer activity thereon. Nevertheless, the cancer is particularly preferably prostate cancer, pancreatic cancer, and colorectal cancer because the antibody of the present invention strongly suppresses the growth of prostate cancer cells, pancreatic cancer cells, and colorectal cancer cells as described in Examples later.

The pharmaceutical composition comprising the antibody of the present invention as an active ingredient can be used in the form of a composition comprising the antibody of the present invention and any ingredient, for example, a saline, an aqueous glucose solution, a phosphate buffer, or the like. The pharmaceutical composition of the present invention may be formulated in a liquid or lyophilized form as necessary, and may optionally comprise a pharmaceutically acceptable carrier or medium, for example, a stabilizer, a preservative, an isotonic agent, or the like.

Examples of the pharmaceutically acceptable carrier include: mannitol, lactose, saccharose, human albumin, and the like for a lyophilized preparation; and a saline, water for injection, phosphate buffer, aluminium hydroxide, and the like for a liquid preparation. However, the examples are not limited to these.

The method for administering the pharmaceutical composition differs depending on the age, weight, sex, health state of an administration target, and the like. The administration can be carried out by any administration route: oral administration and parenteral administration (for example, intravenous administration, intraarterial administration, local administration). A preferable administration method is parenteral administration. The dose of the pharmaceutical composition may vary depending on the age, weight, sex, and health state of a patient, the degree of the progression of the symptom, and components of the pharmaceutical composition to be administered. Nevertheless, the dose is generally 0.1 to 1000 mg, preferably 1 to 100 mg, per kg body weight for an adult per day in the case of intravenous administration.

The antibody of the present invention is presumably applicable not only to the treatment and prevention of the disease associated with the CXADR protein but also to testing for such a disease. Particularly, since the positions 181 to 230 of the CXADR protein derived from human where the epitope of the antibody of the present invention is present are located in an extracellular region of the CXADR protein, cells expressing the CXADR protein can be easily and efficiently detected by cell immunostaining, flow cytometry, or the like. Particularly, regarding the cancers, the level of the CXADR gene expressed is generally low in non-cancerous cells (non-cancerous tissues), but high in various cancer cell lines as described in the gene expression profile database (BioGPS, biogps.org/#goto=welcome), too. Furthermore, in comparing LNCaP-CR cells with LNCaP cells, there is a possibility that the CXADR protein is involved in the malignant progression of cancer. Accordingly, the antibody of the present invention may be utilized in testing for the malignancy of a cancer based on the CXADR protein expression. Thus, the present invention provides an agent for testing a disease (for example, a cancer) associated with a CXADR protein, the agent comprising the antibody of the present invention as an active ingredient.

When the antibody of the present invention is used in the testing for the disease associated with the CXADR protein, or used in the detection of a diseased site in treating the disease (for example, a tumor site in a cancer treatment), the antibody of the present invention may be labeled. As the label, it is possible to use, for example, a radioactive substance, a fluorescent dye, a chemiluminescent substance, an enzyme, or a coenzyme. Specific examples thereof include radioisotopes, fluoresceins, rhodamines, dansyl chloride, luciferases, peroxidases, alkaline phosphatases, lysozymes, biotin/avidin, and the like. When the antibody of the present invention is to be prepared as a testing agent, it can be obtained in any dosage form by adopting any means suitable for the purpose. For example, a purified antibody is measured for the antibody titer and diluted as appropriate with PBS (Phosphate buffer saline, phosphate buffer containing saline) or the like; thereafter, 0.1% sodium azide or the like can be added as a preservative thereto. Alternatively, for example, the antibody of the present invention adsorbed to latex or the like is measured for the antibody titer and diluted as appropriate, and a preservative is added thereto for use.

Additionally, the pre sent invention has revealed that the antibody capable of binding to the epitope present at the positions 181 to 230 of the CXADR protein derived from human has an anti-cancer activity. Accordingly, the polypeptide having the amino acid sequence of the positions 181 to 230 of the CXADR protein derived from human or the partial peptide can be administered as a cancer vaccine to a mammal including a human (see, for example, Japanese Unexamined Patent Application Publication Nos. 2007-277251 and 2006-052216). The present invention also provides a cancer vaccine composition for use as such a cancer vaccine, the cancer vaccine composition comprising a polypeptide having an amino acid sequence of positions 181 to 230 of a CXADR protein derived from human or a partial peptide thereof.

When formulated, the cancer vaccine composition may comprise a pharmaceutically acceptable carrier or medium, for example, a stabilizer, a preservative, an isotonic agent, or the like, as in the case of the anticancer agent of the present invention.

In addition, as described in Examples 9 and 14 later, it has been revealed that the anti-cancer activity of the anti-CXADR antibody of the present invention is demonstrated when the antibody binds to CXADR, in other words, the antibody of the present invention is capable of exhibiting the anti-cancer activity against cancer cells expressing the CXADR protein. Furthermore, as described above, the level of the CXADR gene expressed is generally low in non-cancerous cells (non-cancerous tissues), but high in various cancer cell lines.

Thus, the present invention provides a method for determining effectiveness of a cancer treatment, the method comprising a step of detecting the presence or absence of a CXADR protein in a sample isolated from a patient, wherein if the presence of the CXADR protein is detected in the step, it is determined that the effectiveness of the cancer treatment using a cancer treatment agent comprising the antibody of the present invention as an active ingredient is high for the patient.

Moreover, the present invention provides a cancer treatment agent comprising the antibody of the present invention as an active ingredient, which is administered to the patient for whom the effectiveness is determined to be high by the method described above.

Further, the present invention provides a method for treating a cancer, comprising administering a cancer treatment agent comprising the antibody of the present invention as an active ingredient to the patient for whom the effectiveness is determined to be high by the method described above.

In the present invention, the term "patient" may be not only a person having a cancer, but may also be a person who may have a cancer. Moreover, examples of a "sample" to be isolated from such patients include not only biological samples (for example, cells, tissues, organs, body fluids (such as blood, lymph), digestive juices, sputa, and bronchoalveolar lavage fluid, urine, feces), but also protein extracts and nucleic acid extracts (mRNA extracts, cDNA preparations and cRNA preparations prepared from mRNA extracts) obtained from these biological samples. Further, the sample may be subjected to a formal in fixation treatment, an alcohol fixation treatment, a freezing treatment, or a paraffin embedding treatment. In addition, those skilled in the art can prepare the protein, mRNA, cDNA, and the like by taking the type and the state of the sample and so forth into consideration and selecting a known technique appropriate therefor.

In "detecting the presence or absence of a CXADR protein" in the present invention, the CXADR protein may be detected directly, or may be detected indirectly by detecting an mRNA, a cDNA, or the like encoding the protein.

Known methods can be employed for such detections. In the case of targeting the "CXADR protein" itself, examples of such known methods include immunological methods using an antibody against the CXADR protein (a western blot method, an ELISA method, flow cytometry, immunohistochemical staining, imaging cytometry, radioimmunoassay, immunoprecipitation, an analysis method using an antibody array, and the like). In the case of targeting "an mRNA, a cDNA, or the like encoding the CXADR protein," the examples include an RT-PCR method, a northern blotting method, a dot blot method, and an analysis method using a cDNA microarray.

If the presence of the CXADR protein is detected in a sample isolated from a patient in the method of the present invention, it is determined that the effectiveness of a cancer treatment using the cancer treatment agent comprising the antibody of the present invention as an active ingredient is high for the patient. On the other hand, if the presence of the protein is not detected, it is determined that the effectiveness of the cancer treatment using the treatment agent is low for the patient.

In addition, regarding the "cancer treatment agent" and the "method for treating a cancer" of the present invention, the administration to the patient for whom the effectiveness of the cancer treatment agent of the present invention is determined to be high differs, as described above, depending on the age, weight, sex, health state of the administration target, and the like. The administration can be carried out by selecting any of routes of administration: oral administration and parenteral administration (for example, intravenous administration, intraarterial administration, local administration).

EXAMPLES

Hereinafter, the present invention will be more specifically described on the basis of Examples. However, the present invention is not limited to the following Examples. Moreover, the present Examples were carried out according to the following methods using the following cells, antibodies, and so forth.

<Cells, Antibodies, and so Forth>

Human prostate cancer cells LNCaP, human prostate cancer cells DU-145, human prostate cancer cells PC-3, human pancreatic cancer cells BxPC-3, and human colorectal cancer cells DLD-1 were purchased from ATCC. LNCaP-CR cells were established by the present inventors. The cells were cultured at 37° C. in 5% $CO_2$ in media of DMEM supplemented with 10% FBS (manufactured by GIBCO), 100 units/ml of penicillin G, and 100 µg/ml of streptomycin.

A rabbit anti-asialo GM1 antibody was purchased from Wako Pure Chemical Industries, Ltd. A mouse IgG2a isotype control antibody was purchased from Sigma-Aldrich Co. or Cell Lab. A mouse IgG2b isotype control antibody was purchased from Cell Lab. Calcein AM was purchased from Molecular Probes. Low-Tox®-M rabbit complement was purchased from Cedarlane Corporation.

<SST-REX>

The established prostate cancer cells of the LNCaP cells and the LNCaP-CR cells, each $2 \times 10^7$, were suspended in 1 ml of Trizol (manufactured by Invitrogen corp., #15596-026) and left standing for 5 minutes. Then, 200 µl of chloroform was added thereto, followed by suspension for 15 seconds. After that, the resultant was centrifuged at 12000 g for 15 minutes to obtain a supernatant. The supernatant was mixed with 500 µl of isopropanol, followed by centrifugation at 12000 g for 10 minutes. The obtained pellets were washed with 80% ethanol, and 200 µg of Total RNA was obtained. All of the RNA was dissolved in 100 µl of water. FastTrack 2.0 mRNA Isolation kit (manufactured by Invitrogen corp., #K1593-02) was used to perform an operation according to the specification to thus obtain 3 µg of an mRNA. SuperScript Choice System (manufactured by Invitrogen corp., #18090-019) was used to perform an operation according to the specification utilizing all of the obtained mRNA. Thus, a cDNA was prepared. BstXI Adapter (manufactured by Invitrogen corp., #N408-18), 9 µg, was ligated to the obtained cDNA using Ligation High (manufactured by TOYOBO CO., LTD., #LGK-201) for 16 hours. After that, the resultant was electrophoresed on a 1.5% agarose gel, and portions corresponding to sites of 500 to 4000 bp were cut out. Wizard (R) SV Gel and PCR Clean-Up System (manufactured by Promega corporation, #A9282) was used to perform an operation according to the specification for the purification. A pMX-SST vector was treated using a BstXI enzyme (manufactured by Takara Bio Inc., #1027A), and electrophoresed on a 1% agarose gel. A portion corresponding to the vector was cut out. Wizard (R) SV Gel and PCR Clean-Up System was used to perform the operation according to the specification for the purification. Half the amount of the cDNA with BstXI Adapter having been cut out and purified was ligated to 50 ng of the pMX-SST vector having been treated with BstXI, cut out, and purified, using a T4 DNA ligase for 3 hours. The resultant was purified by ethanol precipitation, and dissolved to 10 µl. Of this, 2 µl was mixed with 23 µl of competent cells (manufactured by Invitrogen corp., #18920-015), followed by electroporation under a condition of 1.8 kV. Immediately thereafter, the resultant was suspended in 1 ml of SOC. After these operations were performed twice, shaking culture was performed at 37° C. for 90 minutes. After that, ampicillin was added to 500 ml of LB, and shaking culture was performed for 16 hours. Cells were collected, and the plasmid was purified using 10 NucleoBond® AX 500 columns (manufactured by NIPPON Genetics Co., Ltd., #740574). Thus, the cDNA library was established.

To produce a virus, $2 \times 10^6$ packaging cells Plat-E were suspended in 4 ml of DMEM (manufactured by Wako Pure Chemical Industries, Ltd., #044-29765), poured into a 6-cm dish, and cultured under conditions of 37° C. and 5% $CO_2$ for 24 hours. After 100 µl of opti-MEM (manufactured by GIBCO, #31985070) and 9 µl of Fugene (manufactured by Roche Applied Science, #1814443) were mixed and left standing for 5 minutes at room temperature, 3 µl of the cDNA library was added thereto and left standing at room temperature for 15 minutes. Then, the resultant was added dropwise to the prepared Plat-E. After 24 hours, the supernatant was replaced. After another 24 hours, the supernatant was filtered through a 0.45-µm filter. The obtained filtered supernatant, 0.5 ml, was added to a 10-cm dish prepared to contain $4 \times 10^6$ Ba/F3 cells in 9.5 ml of RPMI-1640 (manufactured by Kohjin Bio Co., Ltd.). Ten µg of polybrene (manufactured by CHEMICON, #TR-1003-G) was added, and further 10 ng of IL-3 was added. After 24 hours, the cells were washed with RPMI-1640 three times, suspended to 200 ml, and spread in each of twenty 96-well plates in an equal amount. The cells grown for 10 days to 20 days thereafter were cultured until the wells were full of the cells. Half the amount of the cells was cultured to expand as stock. Meanwhile, a genome was extracted from the remaining half. PCR was performed using LA Taq DNA Polymerase (manufactured by Takara Bio Inc., #RR002) or PrimeSTAR MAX DNA Polymerase (manufactured by Takara Bio Inc., #R045A) according to the specification. As PCR primers, SST3'-T7 5'-TAATACGACTCACTATAGGGCGCG-CAGCTGTAAACGGTAG-3' (SEQ ID NO: 21) and SST5'-T3 5'-ATTAACCCTCACTAAAGGGAGGGGGTG-GACCATCCTCTA-3' (SEQ ID NO: 22) were used. The PCR products were purified using Wizard(R) SV Gel and PCR Clean-Up System and so forth to perform the operation according to the specification. BigDye Terminator v3.1 Cycle sequencing (manufactured by ABI, #4337456) was used to perform an operation according to the specification for the sequencing. As a primer in the sequencing, SST5'-T3 5'-ATTAACCCTCACTAAAGGGAGGGGGTGGAC-CATCCTCTA-3' (SEQ ID NO: 22) was used. The sequence data were analyzed utilizing www.ncbi.nlm.nih.gov/BLAST/ and www.cbs.dtu.dk/services/SignalP/.

<Preparation of Anti-CXADR Antibody>

As an animal to be immunized, a Balb/c mouse was used. On the day before the day when the immunization was started, 50 µl of an emulsified mixture of TiterMax Gold (manufactured by Alexis Biochemicals, ALX-510-002-L010) with an equivalent amount of PBS was administered to the mouse. Then, $5 \times 10^6$ to $1 \times 10^7$ SST clone cells having the CXADR gene were intraperitoneally injected to the mouse four times at intervals of 2 days for the immunization. After the immunization, the second lymphoid tissues were took out and loosened to obtain a cell population including antibody-producing cells. These cells were mixed with fusion partner cells for cell fusion using polyethylene glycol (manufactured by MERCK KGaA, 1.09727.0100). Thereby, hybridomas were prepared. As the fusion partner cells, mouse myeloma P3U1 (P3-X63-Ag8.U1) cells were used.

The hybridomas were cultured for 10 to 14 days in a DMEM (manufactured by SIGMA-ALDRICH CO., D6046) selective medium containing HAT (manufactured by SIGMA-ALDRICH CO., H0262), 15% FBS containing 30 ml of a culture supernatant of T-24 cells, penicillin/streptomycin (manufactured by GIBCO BRL, 15140-122) at a final concentration of 100 units/ml. Next, hybridomas which reacted with CXADR-expressing cells, but which did not react with negative control cells expressing no CXADR were selected by flow cytometry. The flow cytometry was conducted in such a manner that cells, each $5 \times 10^4$ to $1 \times 10^5$ cells/sample, were stained with 50 µl of a culture supernatant and an PE-labeled anti-mouse antibody (manufactured by Beckman Coulter Inc., IM-0855) was used as an secondary antibody.

The hybridomas producing the culture supernatant which specifically reacted with the CXADR-expressing cells were subjected to limiting dilution to thereby produce monoclones. The reaction was confirmed by flow cytometry. Thus, anti-CXADR antibodies were obtained.

The monoclonal clones each producing the anti-CXADR antibody were acclimatized to a serum-free medium (hybridoma-SFM: manufactured by GIBCO, 12045-076) containing penicillin/streptomycin (manufacturedbyGIBCO BRL, 15140-122) at a final concentration of 100 units/ml. and cultured to expand. Thus, a culture supernatant used for purification was obtained. IgG in the obtained culture supernatant was purified using a Protein A Sepharose (manufactured by GE Healthcare, 17-1279-03) column, MAPS-II Binding Buffer (manufactured by BIO-RAD LABORATORIES, INC., 153-6161), and MAPS-II Elution Buffer (manufactured by BIO-RAD LABORATORIES, INC., 153-6162). The eluted IgG was dialyzed with PBS, and a purified antibody fraction was obtained. The isotype of the antibody was determined using IsoStrip Kit (manufactured by Roche Diagnostics, 1493027).

<In Vitro Cell Growth>

Cells were dispersed in 10% FBS-containing DMEM at $5 \times 10^4$/ml, and seeded into a 96-well plate at 0.1 ml/well. A predetermined concentration of the antibody was added thereto and cultured at 37° C. in 5% $CO_2$ for 3 days. The cell growth was measured by the MTT method (3-(4,5-dimethyl-2-thiazolyl)-2, 5-diphenyltetrazolium bromide; manufactured by Sigma-Aldrich Co.) (see Fukazawa, H. et al., Anal. Biochem., 1995, vol. 228, pp. 83 to 90). A MTT solution (5 mg/ml PBS), 10 µl, was added to each well, followed by culturing for 4 hours. A formazan product thus produced was dissolved by adding to each well 100 µl of a 20% SDS solution containing 10 mM HCl, and the absorbance at 570 nm was measured.

<Preparation of CXADR Knockdown Cells>

An expression plasmid for a shRNA targeting the human CXADR gene or an expression plasmid for a control shRNA (both were Sure Silencing shRNA Plasmids having a puromycin resistance gene as a selection marker gene, manufactured by QIAGEN GMBH) was introduced to the human prostate cancer DU-145 cells using a gene introduction reagent (manufactured by Promega Corporation, FuGene HD). Then, the cells were cultured for 3 weeks in 10% FBS/DMEM containing puromycin at a final concentration of 0.75 µg/ml Thus, multiple puromycin-resistant clones were obtained. From the obtained clones, unpurified liquid cell extracts were prepared and subjected to the western blot using an anti-CXADR antibody (manufactured by Sigma-Aldrich Co.) to examine the amount of the CXADR protein. From the clone in which a reduction in the CXADR protein amount was observed, Total RNA was extracted using RNeasy plus kit (manufactured by QIAGEN GMBH), and a reverse transcription reaction was carried out using Reverse Transcription System (manufactured by Promega Corporation). Using the synthesized cDNA as a template, real-time PCR was performed using SYBR Premix Ex Taq II (manufactured by Takara Bio Inc.). The clone in which a reduction in the CXADR mRNA amount was observed was designated as a CXADR-persistently-knockdown cell line.

<Angiogenin Production>

Cells were dispersed in 10% FBS DMEM at $5 \times 10^4$/ml, and seeded into a 96-well plate at 0.1 ml/well. A predetermined concentration of the antibody was added thereto and cultured at 37° C. in 5% $CO_2$ for 3 days. The culture supernatant was collected. The amount of angiogenin in the culture supernatant was measured using an ELISA kit manufactured by R&D Systems, Inc.

<In Vivo Anti-Cancer Activity>

BALB/c nu/nu (male, 7 weeks old) nude mice were purchased from Charles River Laboratories Inc., and grown according to the guideline of Institute of Microbial Chemistry under SPF conditions. Cultured cells were treated with trypsin, and the cells ($8 \times 10^6$) detached from the culture dish, were dispersed in 0.3 ml of DMEM containing 10% FBS and mixed with 0.5 ml of growth factor-reduced Matrigel (manufactured by BD Bioscience). The mouse was subcutaneously inoculated with at the left groin with 0.1 ml of this cell solution ($1 \times 10^6$ cells). From the following day, the antibody was intravenously administered for a predetermined period, and a tumor formed beneath the skin was excised to measure the weight. In addition, the tumor volume was calculated from the following formula.

$$\text{Tumor volume (mm}^3\text{)}=(\text{long axis} \times \text{minor axis}^2)/2$$

(see Kawada, M. et al., Cancer Res., 2006, vol. 66, pp. 4419 to 4425).

When transplanted orthotopically, i.e., into the prostate of a mouse, the cells ($20 \times 10^6$) detached from the culture dish were dispersed in 0.15 ml of DMEM containing 10% FBS and mixed with 0.25 ml of growth factor-reduced Matrigel. The abdomen of a BALB/c nu/nu (male, 7 weeks old) nude mouse was cut open under somnopentyl anesthesia to inoculate the mouse at the prostate with 20 µl of the cell solution using a 30 G injection needle, and the opened abdomen was sutured. After a predetermined period, a tumor formed in the prostate was excised, and the weight was measured.

<CDC (Complement-Dependent Cytotoxicity) Activity>

Target cancer cells were dispersed in RPMI 1640 at $2\times10^5$ cells/ml, and labelled at 37° C. for 30 minutes by adding 10 μg/ml of calcein AM. After washed by centrifugation with an RPMI 1640 medium containing 10% FBS three times, the labelled cells were dispersed again in an RPMI 1640 medium containing 10% FBS and left at 37° C. for 1 hour. Again, the cells were washed by centrifugation with an RPMI 1640 medium containing 10% FBS three times, and then re-dispersed in an RPMI 1640 medium containing 10% FBS at $5\times10^5$ cells/ml. The cell solution was seeded into a 96-well plate at 1 ml/well. To this, a predetermined concentration of the antibody was added and cultured at 37° C. for 1 hour. Subsequently, 0.1 ml of a complement solution having been diluted with an RPMI 1640 medium containing 10% FBS was added at a predetermined concentration to each well. The culturing was further continued at 37° C. for 4 hours. After the 96-well plate was centrifuged, 0.1 ml of the culture supernatant was collected. The fluorescence intensity of calcein AM contained in the culture supernatant was measured at an excitation wavelength of 485 nm and an emission wavelength of 528 nm. The CDC cell activity (cytotoxic activity) was calculated according to the following formula.

$$\text{Cytotoxic activity (\%)}=(E-S)/(M-S)\times100$$

(E is a fluorescence intensity under each experimental condition; S is a fluorescence intensity obtained autonomously by adding 0.1 ml of an RPMI 1640 medium containing 10% FBS in place of the complement solution; M is a maximum fluorescence intensity when 0.1 ml of a cell lysate (0.5% Triton X-100, 10 mM Tris-HCl (pH 7.4), 10 mM EDTA) was added in place of the complement solution).

<ADCC (Antibody-Dependent Cell-Mediated Cytotoxicity) Activity>

A spleen was extracted from the nude mouse, and the spleen cells were dispersed using a syringe. The red blood cells were ruptured by a treatment with ice cold water for 10 seconds. The remaining spleen cells were washed by centrifugation with an RPMI 1640 medium and then adjusted to $2.5\times10^7$ cells/ml using RPMI 1640 containing 10% FBS. Target cancer cells were dispersed in RPMI 1640 at $5\times10^5$ cells/ml, and labelled at 37° C. for 30 minutes by adding 10 μg/ml of calcein AM. After washed by centrifugation with an RPMI 1640 medium containing 10% FBS three times, the labelled cells were dispersed again in an RPMI 1640 medium containing 10% FBS and left at 37° C. for 1 hour. Again, the cells were washed by centrifugation with an RPMI 1640 medium containing 10% FBS three times, and then re-dispersed in an RPMI 1640 medium containing 10% FBS at $5\times10^5$ cells/ml. The cell solution was seeded into a 96-well plate at 0.1 ml/well. To this, 0.1 ml of the spleen cell solution per well was added at a predetermined ratio and cultured at 37° C. for 4 hours. After the 96-well plate was centrifuged, 0.1 ml of the culture supernatant was collected. The fluorescence intensity of calcein AM contained in the culture supernatant was measured at an excitation wavelength of 485 nm and an emission wavelength of 528 nm. The NK cell activity (cytotoxic activity) was calculated according to the following formula.

$$\text{Cytotoxic activity (\%)}=(E-S)/(M-S)\times100$$

(E is a fluorescence intensity under each experimental condition; S is a fluorescence intensity obtained autonomously by adding 0.1 ml of an RPMI 1640 medium containing 10% FBS in place of the spleen cell solution; M is a maximum fluorescence intensity when 0.1 ml of a cell lysate (0.5% Triton X-100, 10 mM Tris-HCl (pH 7.4), 10 mM EDTA) was added in place of the spleen cell solution).

(see Kawada M. et al., Int. Immunopharmacol., 2003, vol. 3, pp. 179 to 188).

When NK cells of the mouse were removed, 100 μg of the anti-asialo GM1 antibody was administered to the caudal vein for a predetermined period (see the literature).

<Statistical Analysis>

All the data are of representative two or three independent experiments from which similar results were obtained. Student's t-test was used for the statistical analysis.

<Determination of Antibody Variable Region>

After $2\times10^6$ antibody-producing cells were suspended in 1 ml of Trizol and left standing for 5 minutes, 200 μl of chloroform was added thereto, followed by suspension for 15 seconds. After that, the resultant was centrifuged at 12000×g for 15 minutes to obtain a supernatant. The supernatant was mixed with 500 μl of isopropanol, followed by centrifugation at 12000×g for 10 minutes. The obtained pellets were washed with 80% ethanol, and 40 μg of total RNA was obtained. All of the RNA was dissolved in 20 μl of water. Of these, 5 μg was used to prepare double-stranded cDNAs. In the preparation method, SuperScript Choice System was used according to the specification. After the ethanol precipitation, Ligation High was used for the ligation for 16 hours. Of the resultant, 1 μl was used as a template to carry out PCR. Primers used were designed for constant regions of a heavy chain and a light chain. The sequences of the primers used were:

```
heavy chain
                              (SEQ ID NO: 23)
5' gtccacgaggtgctgcacaat, heavy chain
                              (SEQ ID NO: 24)
3' gtcactggctcagggaaataacc, light chain
                              (SEQ ID NO: 25)
5' aagatggatacagttggtgc,
and light chain
                              (SEQ ID NO: 26)
3' tgtcaagagcttcaacagga.
```

The PCR products were each electrophoresed on a 1.5% gel, and then cut out and purified. Using the purified DNA, sequencing was performed. The sequencing of the light chain was performed after the purified DNA was cloned.

<Epitope Analysis>

To specify an epitope of an ACT196-514_6G10A antibody, Ba/F3 cells expressing CXADR peptides of various chain lengths were prepared, and the reactivity of the antibody was evaluated. The peptides of extracellular regions of 83aa (from the N terminus. The same applies hereinafter), 133aa, 181aa, and 237aa (full extracellular length) were targeted in the analysis. The analysis was conducted using as a template the cDNA library obtained by carrying out the signal sequence trap method on LNCaP-CR, using DNAs of the following sequences as primers, and using PrimeSTAR MAX DNA Polymerase (manufactured by TaKaRa Bio Inc., #R045A) according to the specification. Note that, among the following primers, a forward primer (hereinafter referred to as an abbreviation of "F") was used in common in amplifying the genes. Moreover, in the designations for reverse primers, the numerical values added to Rs mean chain lengths of peptides encoded by the amplified products.

F:
(SEQ ID NO: 27)
ccggaattcccacggcacggcagccaccatgg

R237:
(SEQ ID NO: 28)
ttttccttttgcggccgctccagctttatttgaaggagggac

R230:
(SEQ ID NO: 29)
ttttccttttgcggccgcggacaacgtttagacgcaacag

R181:
(SEQ ID NO: 30)
ttttccttttgcggccgctgagtcagacaattttttgccactc

R134:
(SEQ ID NO: 31)
ttttccttttgcggccgcaatcttcttatttgcaacaccagg

R83:
(SEQ ID NO: 32)
ttttccttttgcggccgcgtagtcatcataaattttgtctcc.

The PCR products were each electrophoresed on a 1% gel. After cutting out and purification, the resultant was treated with restriction enzymes EcoRI and NotI. pMX-SST was also treated with restriction enzymes EcoRII and NotI, and cut out and purified. Each of the products was treated with Ligation High according to the specification. *Escherichia coli* was transformed with all of the treated products by the heat shock method. The resultant was plated on an ampicillin-containing LB agarose plate, and cultured at 37° C. overnight. PCR was carried out on the obtained colonies in such a manner as to incorporate the inserted portions. Whether the pMX-SST vector incorporated the desired sequences was checked by sequencing. As the used PCR primers, SST3'-T7 5'-TAATACGACTCACTATAGGGCGCG-CAGCTGTAAACGGTAG-3' (SEQ ID NO: 21) and SST5'-T3 5'-ATTAACCCTCACTAAAGG-GAGGGGGTGGACCATCCTCTA-3' (SEQ ID NO: 22) were used. The colonies confirmed to have the targeted inserts inserted were cultured. The plasmid was purified using NucleoBond(registered trademark) AX 500 columns. To produce a virus, $2\times10^6$ packaging cells Plat-E were suspended in 4 ml of DMEM (manufactured by Wako Pure Chemical Industries, Ltd., #044-29765), poured into a 6-cm dish, and cultured under conditions of 37° C. and 5% $CO_2$ for 24 hours. After 100 μl of opti-MEM and 9 μl of Fugene were mixed and left standing for 5 minutes at room temperature, 3 μg of the pMX-SST vector having the target sequences was added thereto and left standing at room temperature for 15 minutes. Then, the resultant was added dropwise to the prepared Plat-E. After 24 hours, the supernatant was replaced. After another 24 hours, the supernatant was filtered through a 0.45-μm filter. The obtained filtered supernatant, 0.5 ml, was added to a 10-cm dish prepared to contain $4\times10^6$ Ba/F3 cells in 9.5 ml of RPMI-1640(manufactured by Kohjin Bio Co., Ltd.). Ten μg of polybrene (manufactured by CHEMICON, #TR-1003-G) was added, and further 10 ng of IL-3 was added. After 24 hours, the cells were washed with RPMI-1640 three times, suspended in 10 ml of RPMI-1640, added to a 10-cm dish, and cultured under conditions of 37° C. and 5% $CO_2$ for 10 days. A genome was extracted from the grown cells. PCR was performed using LA Taq DNA Polymerase or PrimeSTAR MAX DNA Polymerase according to the specification. As PCR primers, SST3'-T7 5'-TAATACGACTCACTAT-AGGGCGCGCAGCTGTAAACGGTAG-3' (SEQ ID NO: 21) and SST5'-T3 5'-ATTAACCCTCACTAAAGG-GAGGGGGTGGACCATCCTCTA-3' (SEQ ID NO: 22) were used.

The PCR products were purified using Wizard(R) SV Gel and PCR Clean-Up System and so forth to perform the operation according to the specification. BigDye Terminator v3.1 Cycle sequencing was used to perform the operation according to the specification for the sequencing. As a primer in the sequencing, SST5'-T3 5'-ATTAACCCTCACTAAAGG-GAGGGGGTGGACCATCCTCTA-3' (SEQ ID NO: 22) was used. The sequence data were analyzed utilizing www.ncbi.nlm.nih.gov/BLAST/. Then, cells expressing regions of target factors obtained in this manner were subjected to epitope analysis.

<Staining Test on Human Umbilical Vein Endothelial Cells (HUVEC Cells)>

In order to examine the reactivity of the antibody against human umbilical vein endothelial cells, the reactivity with HUVEC was checked. HUVEC ($5\times10^3$/well) were seeded into a black 96-well plate (manufactured by BD Falcon, 353219) and cultured over two nights. As the culture solution, EGM-2 BulletKit medium (manufactured by Lonza group Ltd.) was used. After the culturing, the medium was removed, and the resultant was washed once using a staining buffer (0.5% BSA/PBS). Then, 50-μL solutions respectively containing purified 6G10A and 7F8A antibodies at 10 μg/mL were added as a primary antibody and allowed to react at room temperature for 30 minutes. As negative controls, mouse IgG2a-UNLB (clone: HOPC-1, manufactured by Cell Lab, 731589) and mouse IgG2b-UNLB (clone: A-1, manufactured by Cell Lab, 731597) were each dissolved in a staining buffer at a concentration of 10 μg/mL, and 50 μl thereof was added and allowed to react at room temperature for 30 minutes. After the reaction, the primary reaction solution was removed, and the resultant was washed with a staining buffer once. After the washing, 40 μL of goat anti-mouse IgG, F(ab')$_2$-PE (manufactured by Beckman Coulter Inc., IM0855) having been diluted 200 times with a staining buffer was added and allowed to react under conditions of room temperature in the dark for 20 minutes. Further, 10 mg/mL of Hoechst 33342 (manufactured by Invitrogen corp., H1399) was diluted 2000 times, and 30 μl of the resultant was added and allowed to react under conditions of room temperature in the dark for another 20 minutes. Subsequently, washing was performed with a staining buffer twice. After 100 mL of a wash buffer was added, cell staining was observed using a fluorescence microscope (manufactured by Olympus Corporation).

<Flow Cytometry Test on Human Umbilical Vein Endothelial Cells (HUVEC Cells) and Cancer Cells>

In order to examine the reactivity of the antibody against human umbilical vein endothelial cells, the reactivity with HUVEC was checked by adopting a flow cytometry method. HUVEC were cultured using EGM-2 BlettKit medium. Cancer cells were cultured using a medium (RPMI 1640: manufactured by Wako Pure Chemical Industries, Ltd. or DMEM: manufactured by SIGMA-ALDRICH CO.) containing inactivated 10% FCS (manufactured by Equitech-Bio Inc.) and 1% penicillin-streptomycin liquid (manufactured by GIBCO, 15140122). At 80% confluency, the cells were detached and collected from the culture plate using a cell dissociation buffer (manufactured by GIBCO, 13151-014), and washed once with an FCM buffer (0.5% BSA/1 mMEDTA/PBS). The cells were dispensed into a 96-well plate (manufactured by BD Falcon, 353911) at $5\times10^4$ cells/well. Solutions respectively containing purified 6G10A and 7F8A antibodies at 5 μg/mL were added as a primary antibody at 50 μl/well and allowed to react at room temperature for 30 minutes. As negative controls, mouse IgG2a-UNLB (clone: HOPC-1, manufactured by Cell Lab, 731589) and mouse IgG2b-UNLB (clone: A-1, manufactured by Cell Lab, 731597) were each dissolved in a FCM buffer at a concentration of 5 µg/mL, and 50 µl thereof was added and allowed to react at room temperature for 30 minutes. After the reaction, the primary reaction solution was removed by centrifugation at 700×g for 2 minutes, and the resultant was washed with a FCM buffer once. After the washing, 40 µl of goat anti-mouse IgG, F(ab')$_2$-PE (manufactured by Beckman Coulter Inc., IM0855) having been diluted 200 times with a FCM buffer was added and allowed to react under conditions of room temperature in the dark for 30 minutes. After the reaction, the resultant was centrifuged at 700×g for 2 minutes and washed with a FCM buffer twice. The cells were suspended in an appropriate amount of a FCM buffer, and analyzed with a flow cytometer (manufactured by Beckman Coulter Inc., FC500MPL).

Example 1

[SST-REX Analysis]

As a result of analyzing 207 clones of the LNCaP-CR cells by SST-REX, 67 factors were obtained. Moreover, as a result of analyzing 150 clones of the LNCaP cells by SST-REX, 50 factors were obtained. From the result of the LNCaP-CR and the result of the LNCaP cells, 10 factors which demonstrated the expression specifically only to the LNCaP-CR were selected as targets of the anti-cancer activity. Among these, the CXADR gene was selected.

Example 2

[Preparation of Anti-CXADR Antibody]

Figure 2:
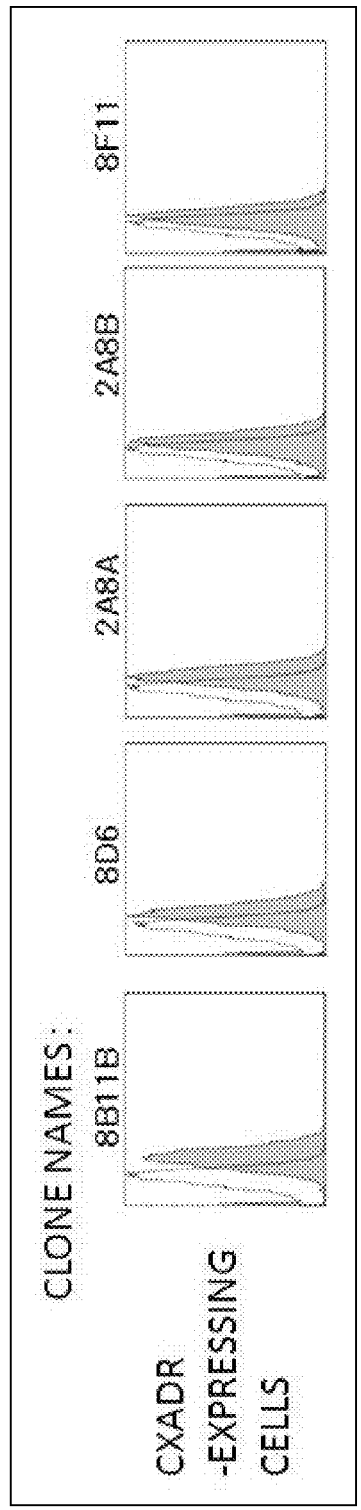
FIG. 2 shows graphs for illustrating the result of analyzing with the flow cytometer the reactivity between the CXADR-expressing cells and each of anti-CXADR antibodies produced from hybridomas (clone names: 8B11B, 8D6, 2A8A, 2A8B, 8F11). Note that, hereinafter, the clone names of the hybridomas such as "6G10A" and "7F8A" are used not only for the corresponding hybridomas but also as names of antibodies by themselves, which are produced from the hybridomas.

The mice were immunized using the Ba/F3 cells expressing the CXADR protein as an immunogen. As a result of screening by flow cytometry, 10 clones were obtained, which reacted specifically with the cells expressing the CXADR protein as shown in FIGS. 1 and 2. Using the 10 clones thus obtained, candidate antibodies were selected by function test screening and the like. Finally, two useful clones, 6G10A and 7F8A, were obtained. Moreover, the result of the class check demonstrated that both were an IgG class, and the subclass was IgG2a/k for 6G10A and IgG2b/k for 7F8A.

Example 3

[In Vitro Cancer Suppressing Effect of Unpurified Anti-CXADR Antibody]

Figure 3:
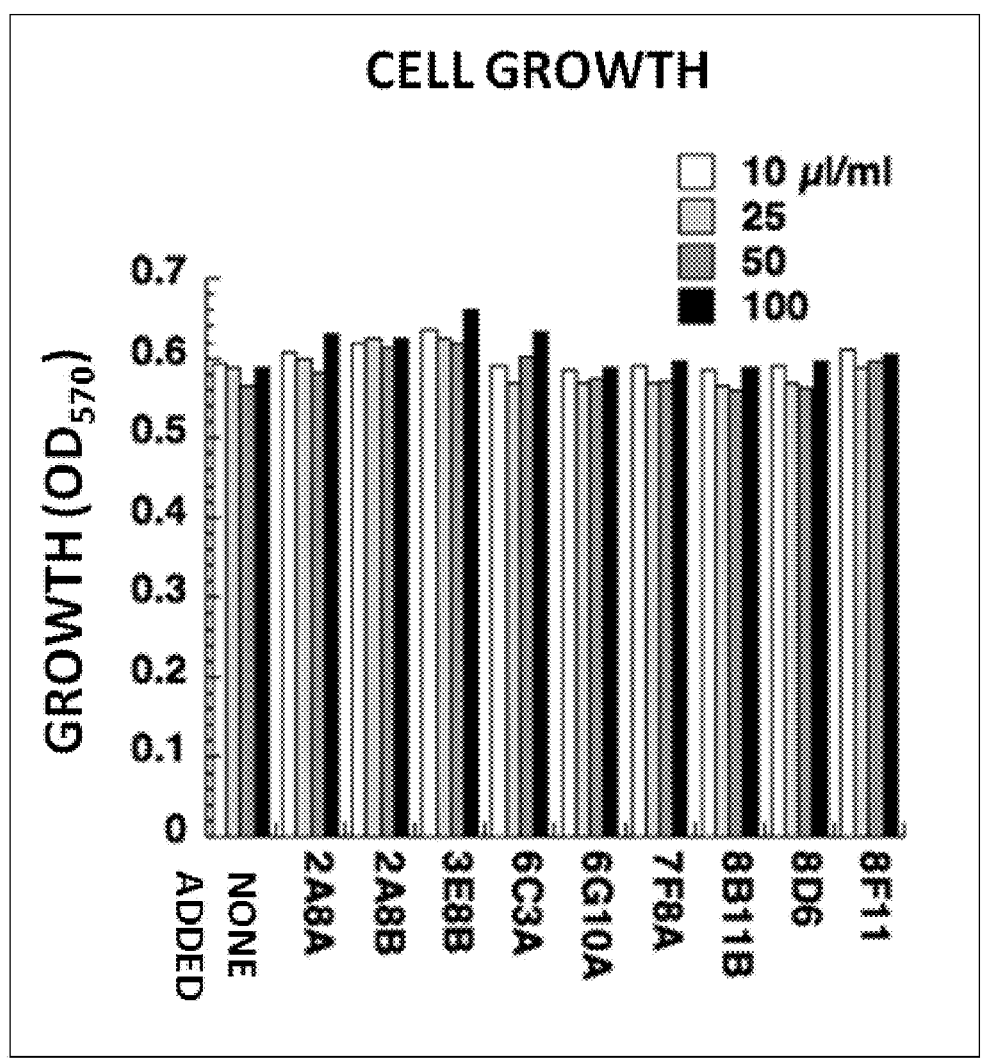
FIG. 3 is a graph for illustrating the result of analyzing the influence of unpurified anti-CXADR antibodies on cell growth. In the figure, the vertical axis represents the number of cells counted (absorbance at 570 nm) by the MTT method after LNCaP-CR cells were cultured in the presence of each unpurified anti-CXADR antibody for 3 days. Moreover, the value represented by each bar in the figure indicates an average value of two-replicate measurement values, and the standard error (SE) is 10% or less.
Figure 4:
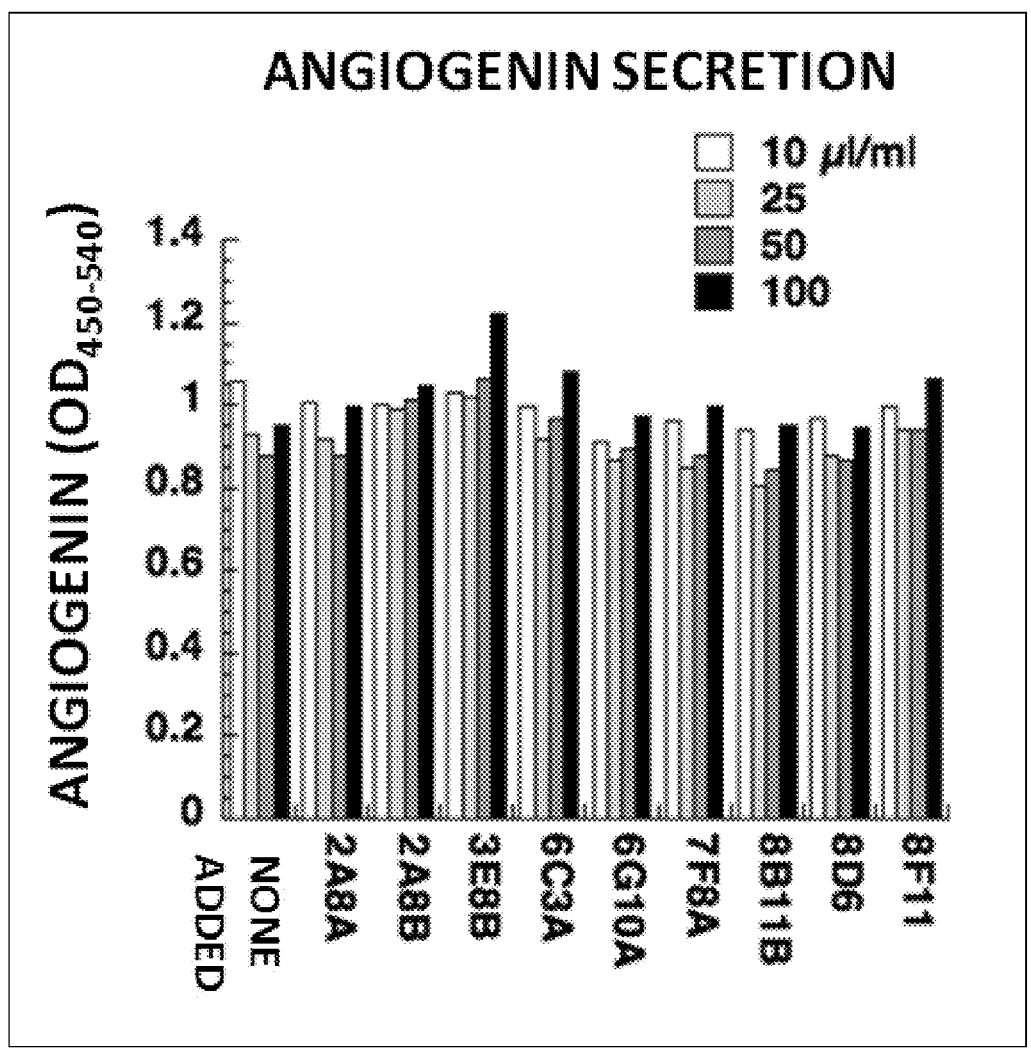
FIG. 4 is a graph for illustrating the result of analyzing the influence of the unpurified anti-CXADR antibodies on angiogenin production. In the figure, the vertical axis represents the amount of angiogenin produced in the culture supernatant, the amount being measured (absorbance at 450-540 nm) by the ELISA method after the LNCaP-CR cells were cultured in the presence of each unpurified anti-CXADR antibody for 3 days. Moreover, the value represented by each bar in the figure indicates an average value of two-replicate measurement values, and the standard error (SE) is 10% or less.

Nine unpurified antibody clones prepared against CXADR were examined for their in vitro influences on the growth of the LNCaP-CR cells and the production of an angiogic factor angiogenin. FIGS. 3 and 4 show the obtained results.

As apparent from the results shown in FIGS. 3 and 4, none of the antibody clones had in vitro influences on the growth of the LNCaP-CR cells and the angiogenin production.

Example 4

[In Vivo Cancer Suppressing Effect of Unpurified Anti-CXADR Antibody]

Figure 5:
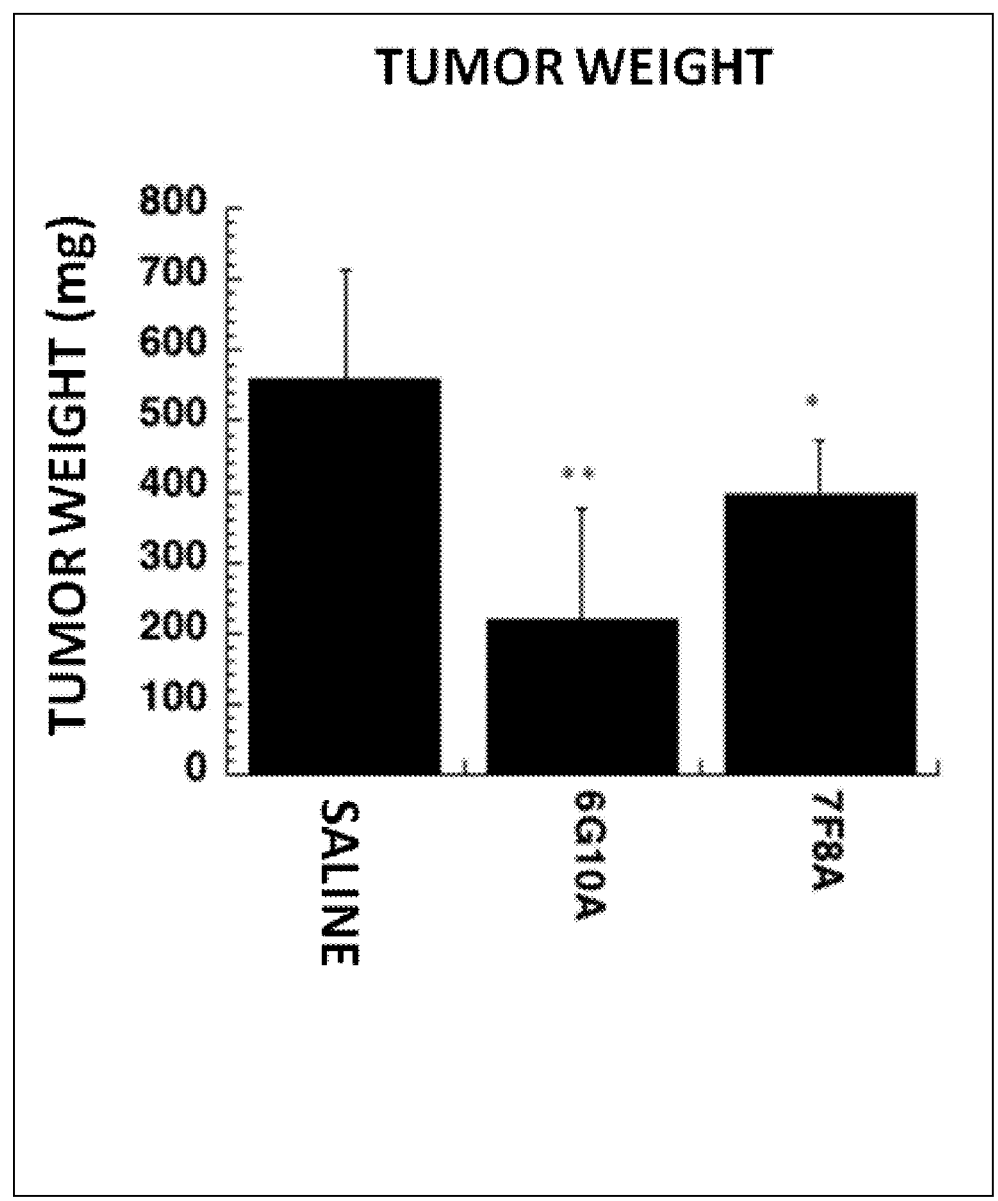
FIG. 5 is a graph for illustrating the result of analyzing the influence of the unpurified anti-CXADR antibody (6G10A or 7F8A) on LNCaP-CR tumor. Nude mice (male, n=5) were subcutaneously inoculated with with the LNCaP-CR cells. For 11 days from the following day, 100 μl of the unpurified antibody or 100 μl of a saline as a negative control was administered into the caudal veins every day. Then, the weight of tumors isolated from the mice after 21 days from the cell inoculation was measured. The value of the weight represented by each bar in the figure is an average value ±standard deviation (SD) of five mice in one group. Moreover, "*" indicates "P<0.05", and "**" indicates "P<0.01".

The LNCaP-CR cells were subcutaneously transplanted into the nude mice, and the antibody clones were intravenously administered for successive 11 days to examine the influence on the growth of LNCaP-CR tumor. FIG. 5 shows the obtained result.

As apparent from the result shown in FIG. 5, it was found out that the 6G10A clone suppressed the tumor weight by approximately 60% on day 21 after the tumor inoculation, and the 7F8A clone approximately 30%. Moreover, although unillustrated, no remarkable anti-cancer activity was observed from the other antibody clones.

Example 5

[In Vivo Cancer Suppressing Effect 1 of Purified Anti-CXADR Antibody]

Figure 6:
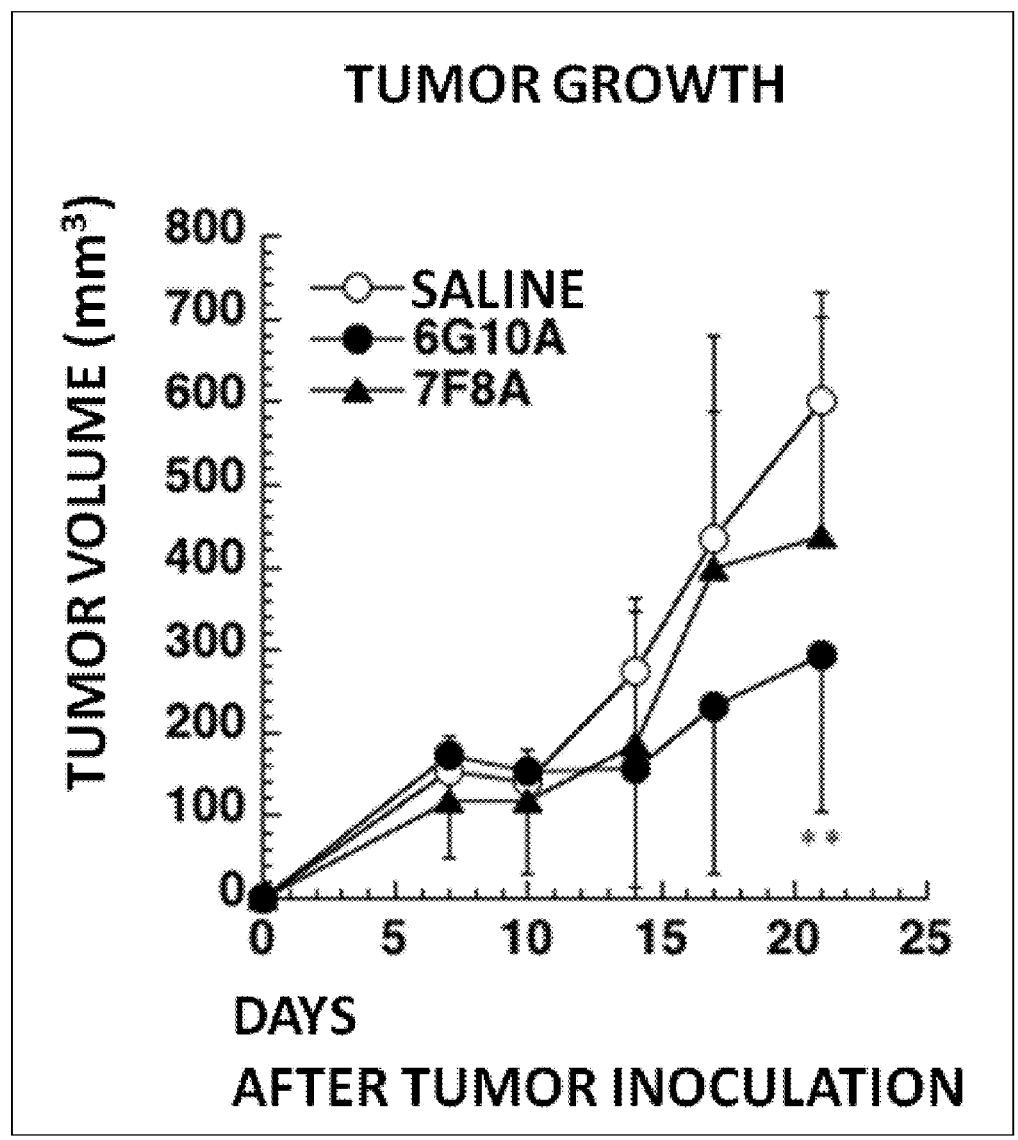
FIG. 6 is a graph for illustrating the result of analyzing the influence of a purified anti-CXADR antibody (6G10A or 7F8A) on LNCaP-CR tumor. Nude mice (male, n=5) were subcutaneously inoculated with the LNCaP-CR cells. After 1 day, 7 days, and 14 days from the inoculation, 250 μg of the purified antibody or a saline as a negative control was administered into the caudal veins. Then, the diameter of tumors isolated from the mice after predetermined periods was measured to calculate the volumes. The values of the volumes represented by each polygonal line in the figure are each an average value ±SD of five mice in one group. Moreover, "**" indicates "P<0.01".
Figure 7:
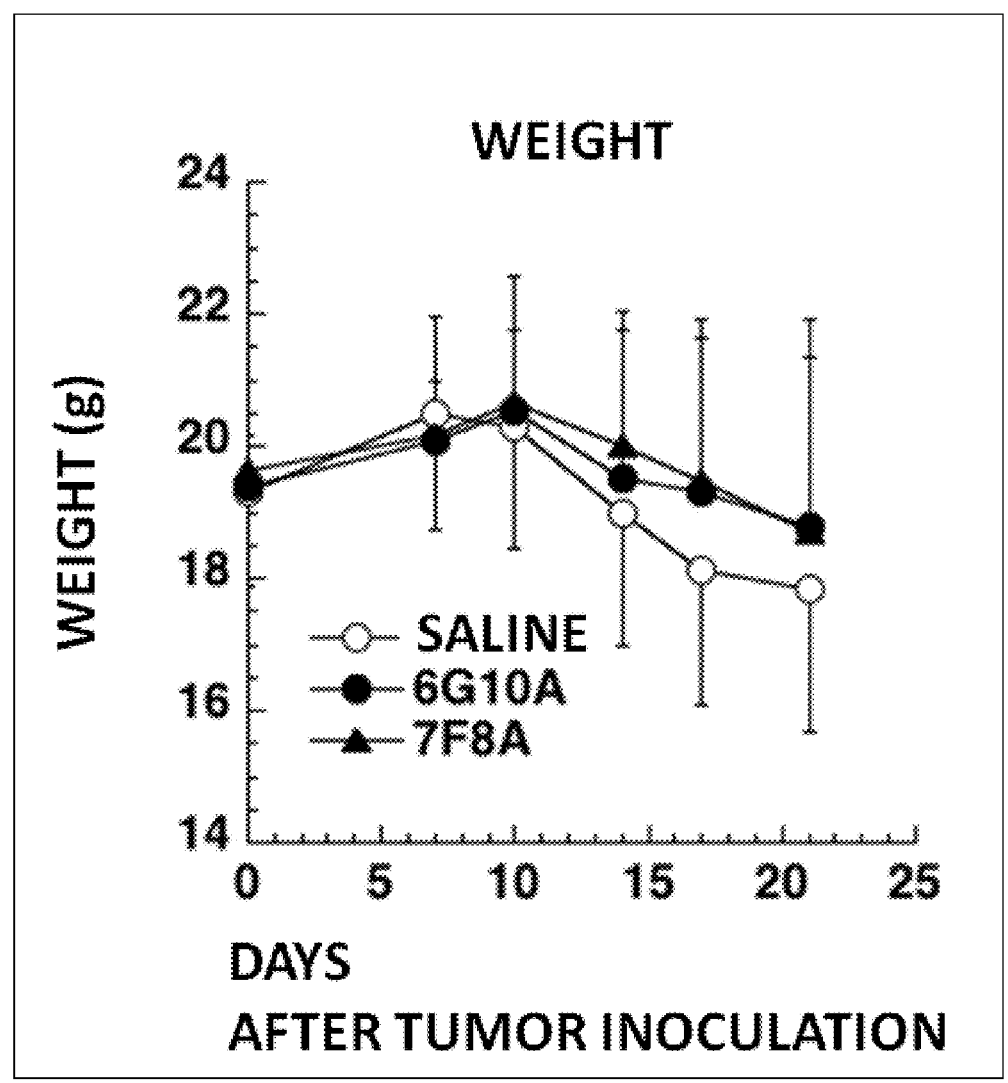
FIG. 7 is a graph for illustrating the result of analyzing the influence of the purified anti-CXADR antibody (6G10A or 7F8A) administration on mice. Nude mice (male, n=5) were subcutaneously inoculated with the LNCaP-CR cells. After 1 day, 7 days, and 14 days from the inoculation, 250 μg of the purified antibody or a saline as a negative control was administered into the caudal veins. Then, the weight of the mice was measured after predetermined periods. The values of the weight represented by each polygonal line in the figure are each an average value ±SD of five mice in one group.
Figure 8:
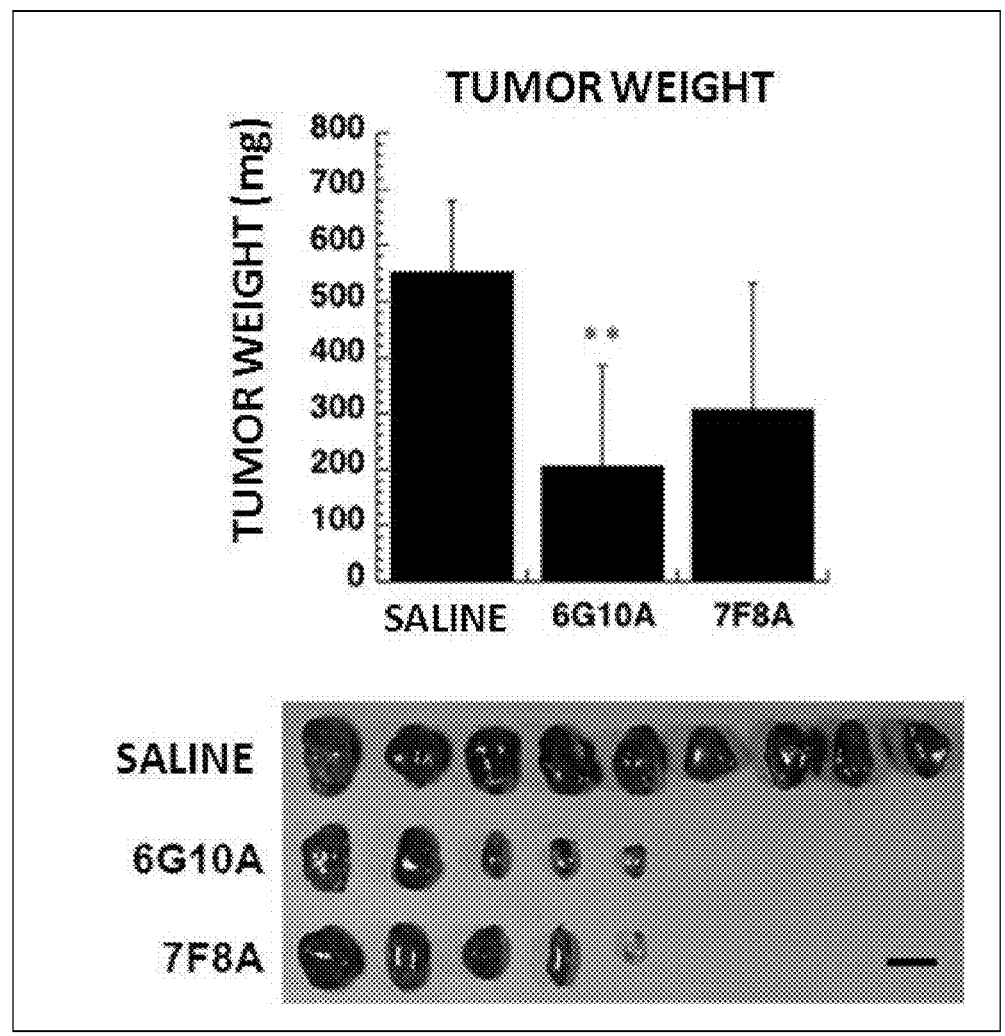
FIG. 8 shows a graph and a photograph for illustrating the result of analyzing the influence of the purified anti-CXADR antibody (6G10A or 7F8A) on LNCaP-CR tumor. Nude mice (male, n=5) were subcutaneously inoculated with the LNCaP-CR cells. After 1 day, 7 days, and 14 days from the inoculation, 250 μg of the purified antibody or a saline as a negative control was administered into the caudal veins. Then, tumors isolated from the mice after 21 days from the cell inoculation were photographed, and the weight of these tumors was measured. The value represented by each bar in the graph is an average value ±SD of five mice in one group. "**" indicates "P<0.01". Moreover, the scale bar in the photograph represents 1 cm.

The LNCaP-CR cells were subcutaneously transplanted into the nude mice, and purified antibodies were administered at 250 µg/mouse once a week three times in total to examine the anti-cancer activities of the antibodies. FIGS. 6 to 8 show the obtained result.

Figure 9:
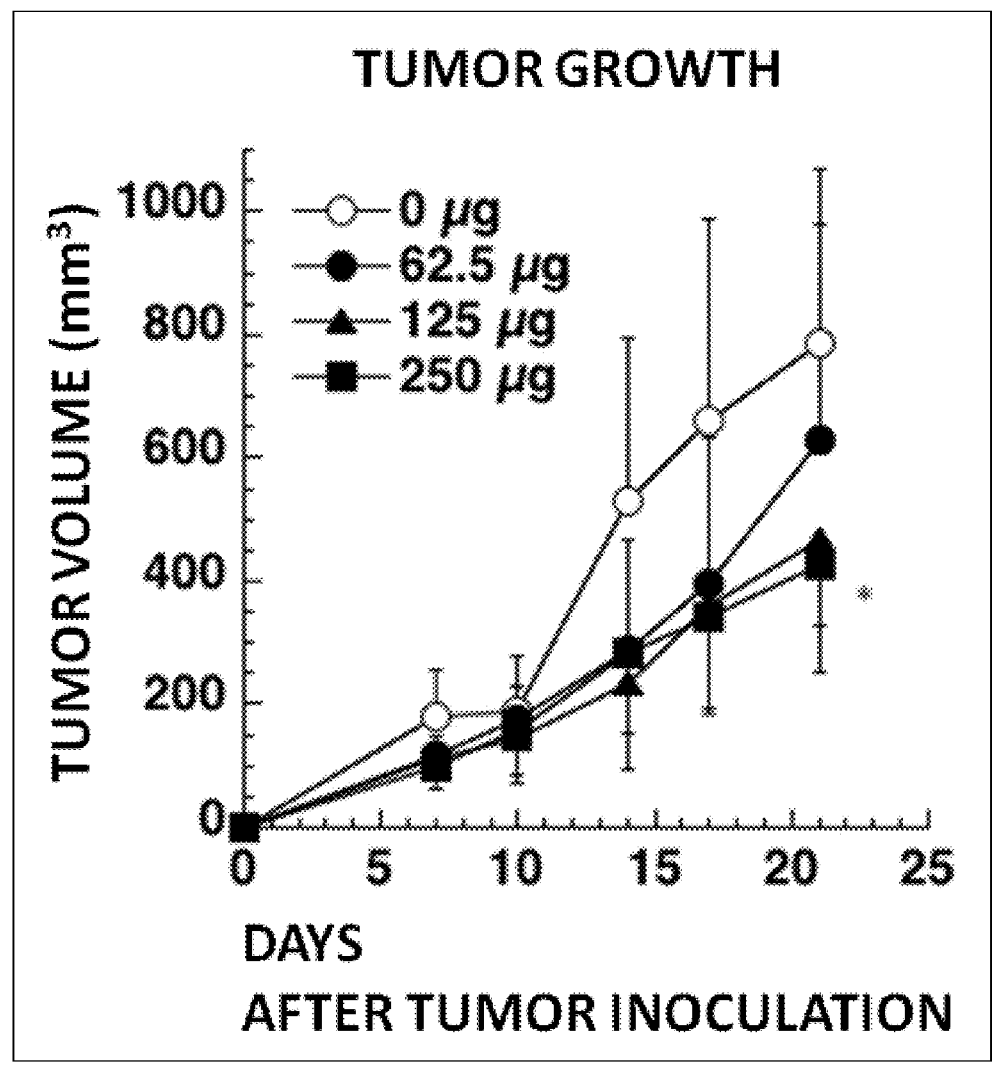
FIG. 9 is a graph for illustrating the result of analyzing the effect of the purified anti-CXADR antibody 6G10A on LNCaP-CR tumor. Nude mice (male, n=5) were subcutaneously inoculated with the LNCaP-CR cells. After 1 day, 7 days, and 14 days from the inoculation, 62.5, 125, or 250 μg of the purified antibody or a saline as a negative control (0 μg of the purified antibody) was administered into the caudal veins. Then, the diameter of tumors isolated from the mice after predetermined periods was measured to calculate the volumes. The values of the volumes represented by each polygonal line in the figure are each an average value ±SD of five mice in one group. Moreover, "*" indicates "P<0.05".
Figure 10:
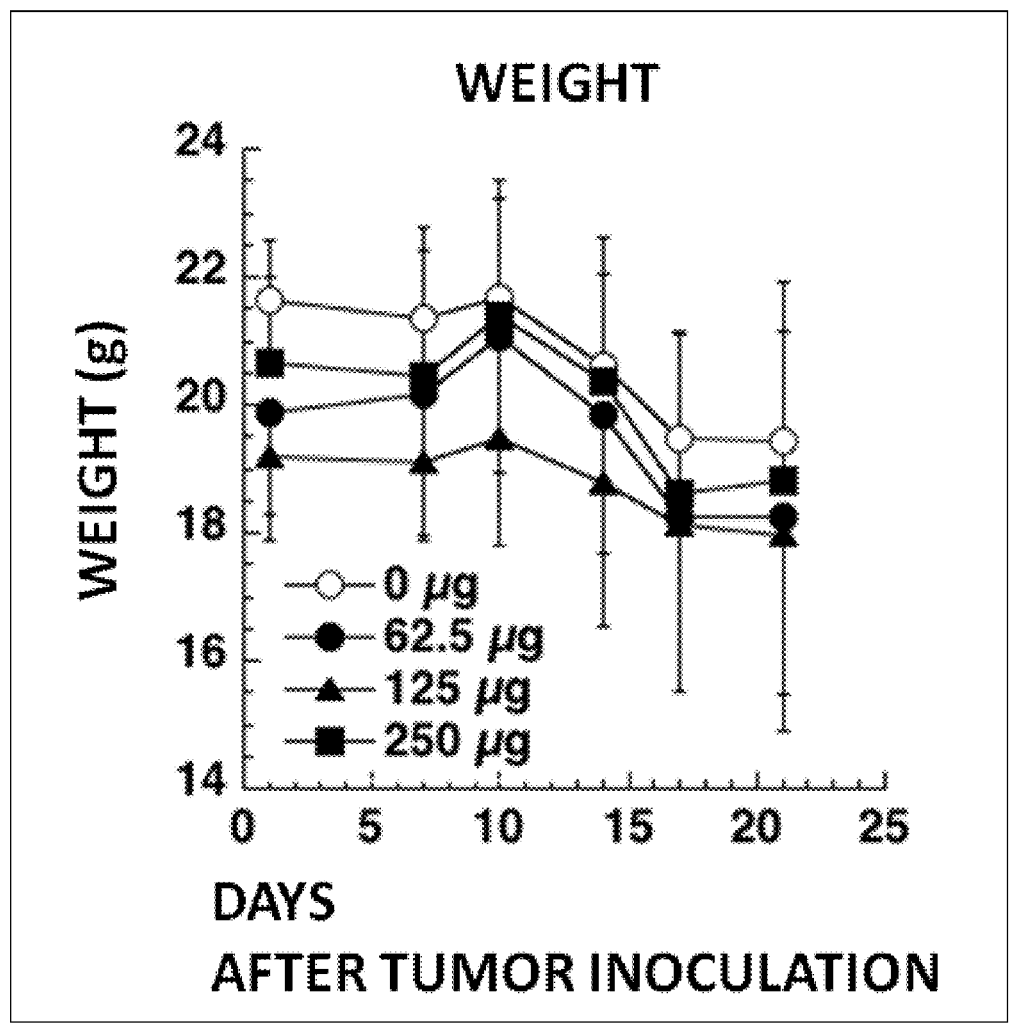
FIG. 10 is a graph for illustrating the result of analyzing the influence of the purified anti-CXADR antibody 6G10A administration on mice. Nude mice (male, n=5) were subcutaneously inoculated with the LNCaP-CR cells. After 1 day, 7 days, and 14 days from the inoculation, 62.5, 125, or 250 μg of the purified antibody or a saline as a negative control (0 μg of the purified antibody) was administered into the caudal veins. Then, the weight of the mice was measured after predetermined periods. The values of the weight represented by each polygonal line in the figure are each an average value ±SD of five mice in one group.
Figure 11:
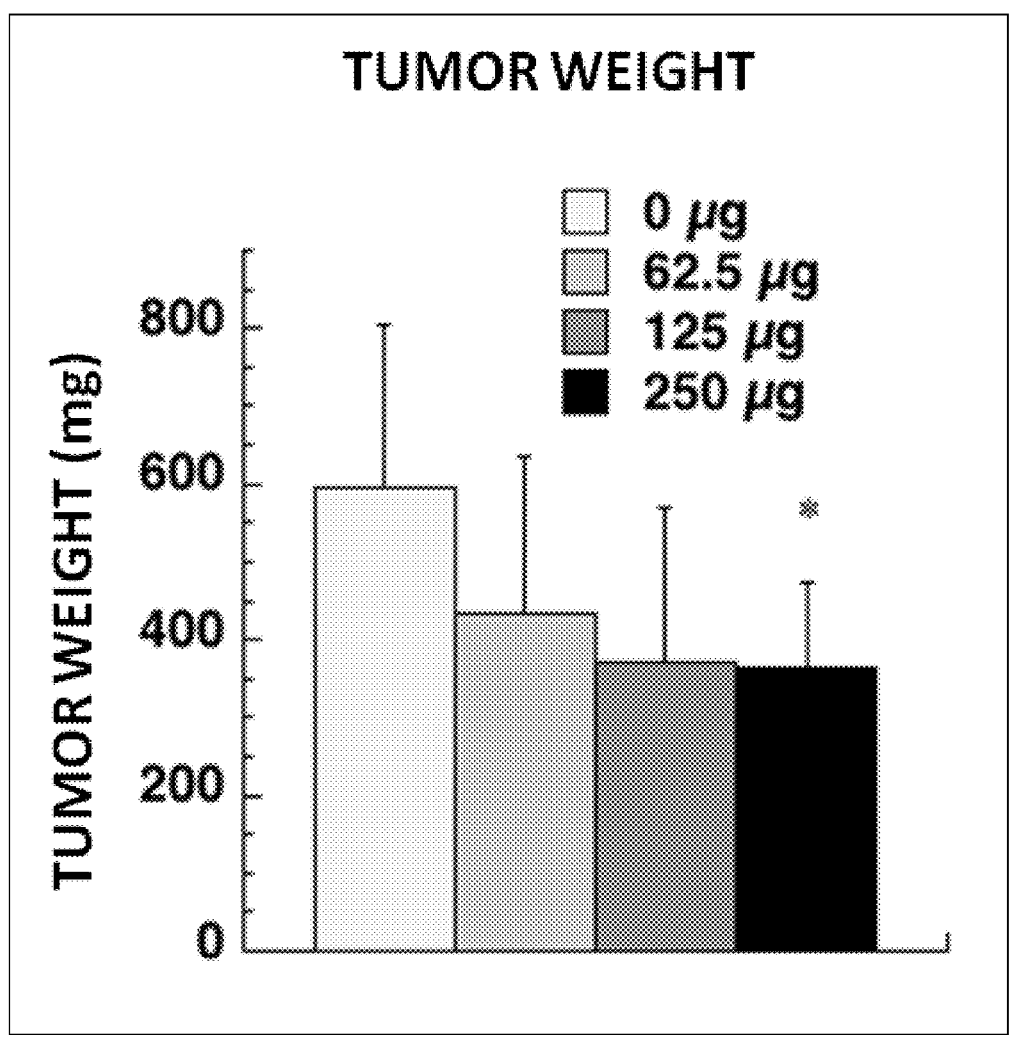
FIG. 11 is a graph for illustrating the result of analyzing the effect of the purified anti-CXADR antibody 6G10A on LNCaP-CR tumor. The LNCaP-CR cells were subcutaneously transplanted into nude mice (male, n=5). After 1 day, 7 days, and 14 days from the inoculation, 62.5, 125, or 250 μg of the purified antibody or a saline as a negative control (0 μg of the purified antibody) was administered into the caudal veins. Then, the mice were sacrificed after 21 days from the cell inoculation, and tumors were resected therefrom to measure the weight. The value represented by each bar in the figure is an average value ±SD of five mice in one group. "*" indicates is "P<0.05".

As shown in FIGS. 6 to 8, it was revealed that the 6G10A clone significantly suppressed the LNCaP-CR tumor weight by approximately 60% on day 21, the 7F8A clone approximately 45%. Moreover, during this period, no toxicity to the mice such as weight loss was observed by the administration of the antibody clones (see FIG. 7). Further, as apparent from the result shown in FIGS. 9 to 11, the 6G10A clone exhibited its anti-cancer activity dependently on the administration amount, and the tumor growth was most significantly suppressed with the administration amount of 250 µg.

Figure 12:
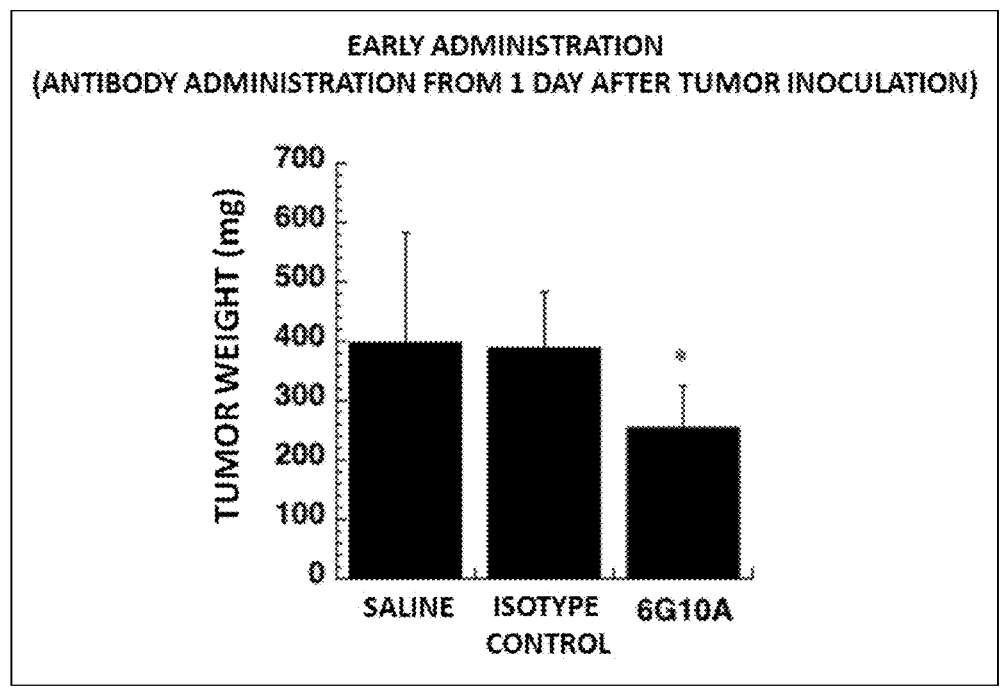
FIG. 12 is a graph for illustrating the result of analyzing the effect of the purified anti-CXADR antibody 6G10A on LNCaP-CR tumor. The LNCaP-CR cells were subcutaneously transplanted into nude mice (male, n=5). After 1 day, 7 days, and 14 days from the inoculation, 250 μg of 6G10A or an isotype control antibody, or a saline was administered into the caudal veins; thus three times (early administration). The mice were sacrificed after 21 days from the cell inoculation, and tumors were resected therefrom to measure the weight. The value represented by each bar in the figure is an average value ±SD of five mice in one group. "*" indicates "P<0.05".
Figure 13:
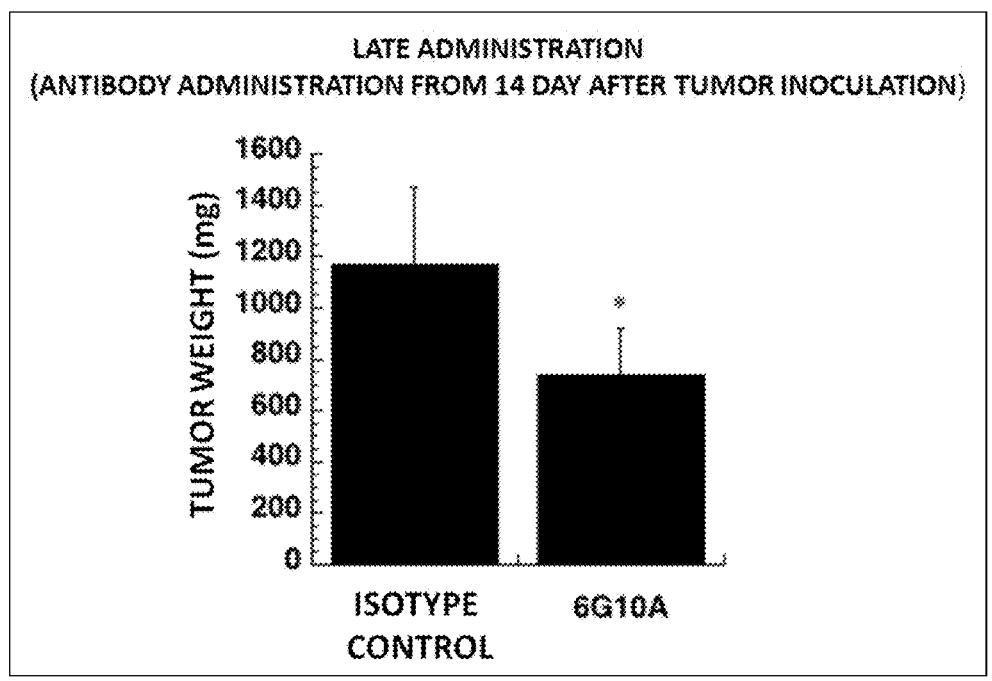
FIG. 13 is a graph for illustrating the result of analyzing the effect of the purified anti-CXADR antibody 6G10A on LNCaP-CR tumor. The LNCaP-CR cells were subcutaneously transplanted into nude mice (male, n=5). After 14 day, 21 days, and 28 days from the inoculation, 250 µg of 6G10A or the isotype control antibody was administered into the caudal veins; thus three times (late administration). The mice were sacrificed after 35 days from the cell inoculation, and tumors were resected therefrom to measure the weight. The value represented by each bar in the figure is an average value ±SD of five mice in one group. "*" indicates "$P<0.05$".

Furthermore, whether the 6G10A clone having a strong effect exhibited the anti-cancer activity against an enlarged tumor was examined. FIGS. 12 and 13 show the obtained result.

As shown in FIGS. 12 and 13, it was revealed that the tumor growth was suppressed by administering the 6G10A clone even when 14 days elapsed after the tumor inoculation.

Example 6

[In Vivo Cancer Suppressing Effect 2 of Purified Anti-CXADR Antibody]

Figure 14:
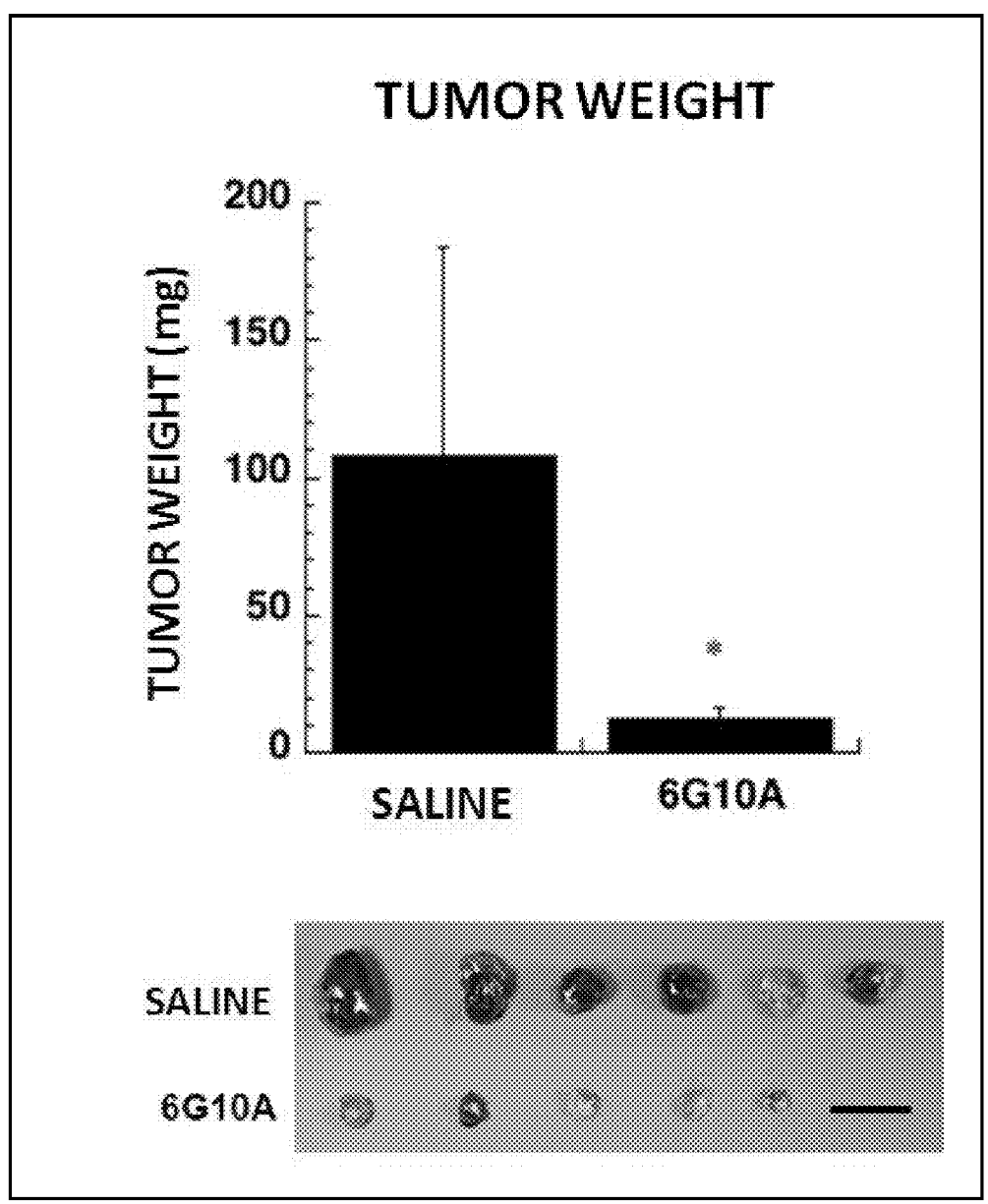
FIG. 14 shows a graph and a photograph for illustrating the result of analyzing the effect of the anti-CXADR antibody 6G10A on a LNCaP-CR orthotopic graft tumor. The LNCaP-CR cells were transplanted into the prostates of nude mice (male, n=5), and 250 µg of 6G10A or a saline was administered into the caudal veins. Then, tumors isolated from the mice after 21 days from the cell inoculation were photographed, and the weight of these tumors was measured. The value represented by each bar in the graph is an average value ±SD of five mice in one group. "*" indicates "$P<0.05$". Moreover, the scale bar in the photograph represents 1 cm.
Figure 15:
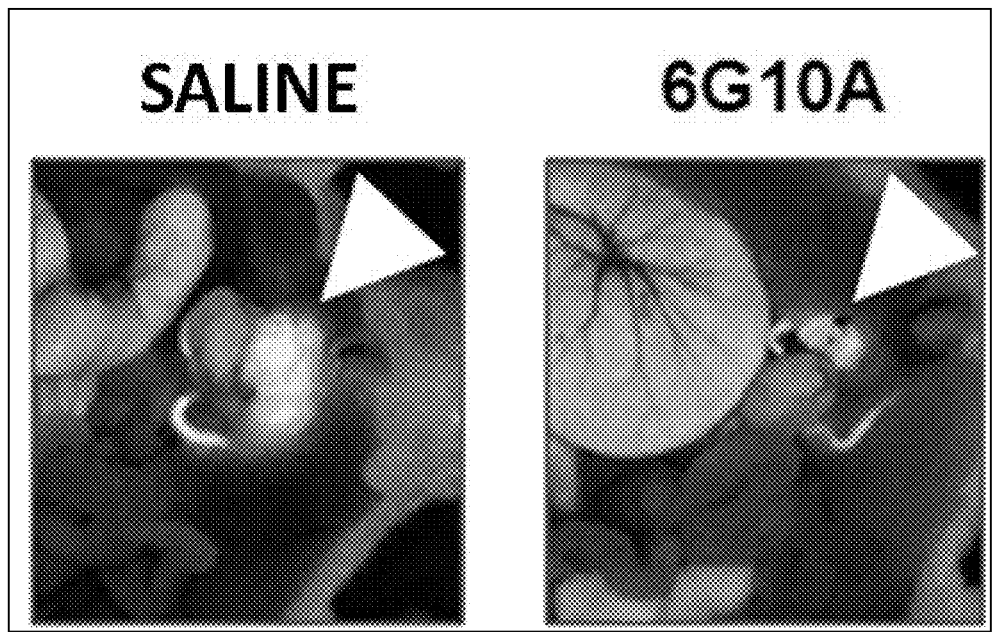
FIG. 15 shows photographs for illustrating a representative administration example (on day 21 after the LNCaP-CR transplantation) of the anti-CXADR antibody 6G10A into the LNCaP-CR orthotopic graft tumor. In the figure, a triangle indicates a "LNCaP-CR tumor."
Figure 16:
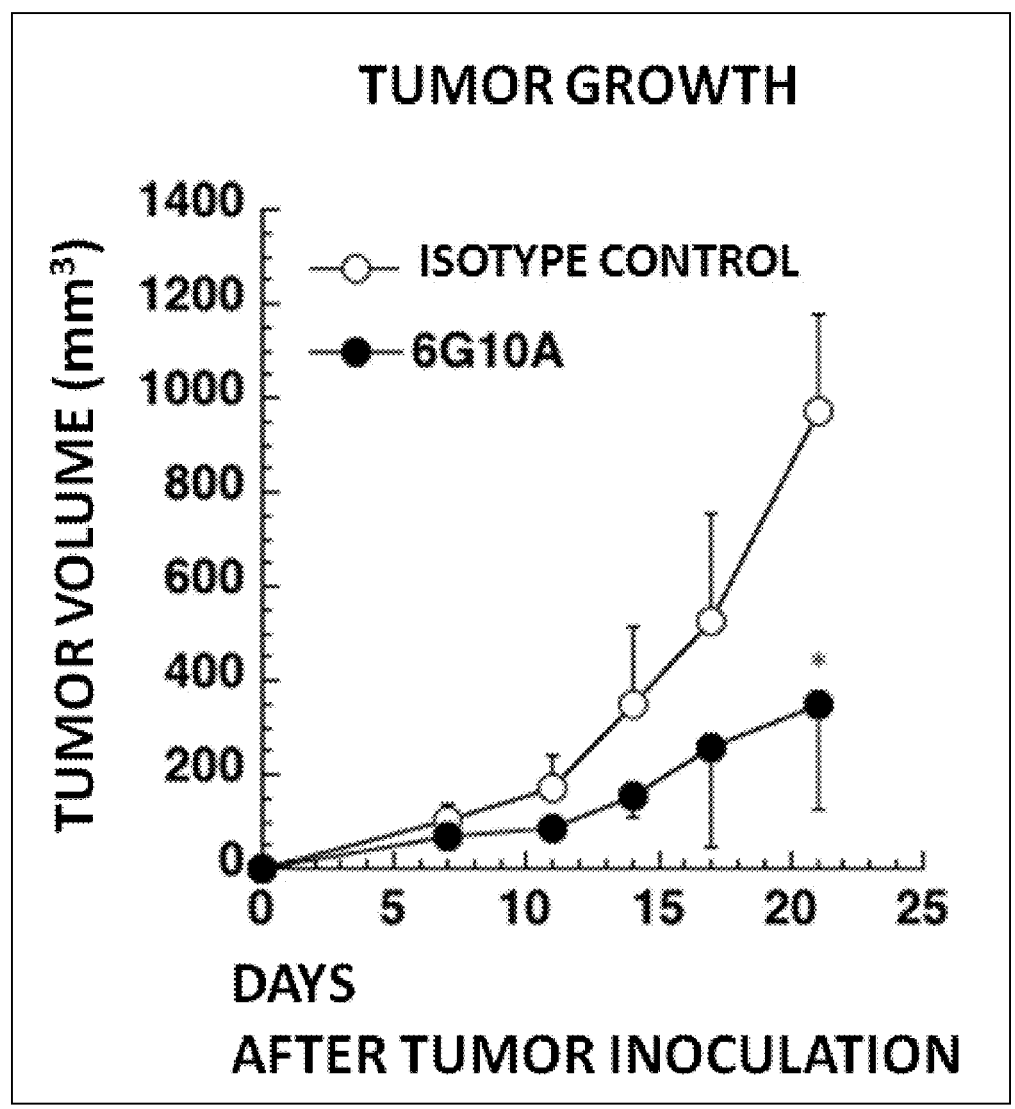
FIG. 16 is a graph for illustrating the result of analyzing the effect of the anti-CXADR antibody 6G10A on DU-145 tumor. DU-145 cells were subcutaneously transplanted into nude mice (male, n=3). After 1 day, 7 days, and 14 days from the inoculation, 250 µg of 6G10A or the isotype control antibody was administered into the caudal veins. Then, the diameter of tumors isolated from the mice after predetermined periods was measured to calculate the volumes. The values of the volumes represented by each polygonal line in the figure are each an average value ±SD of three mice in one group. Moreover, "*" indicates "$P<0.05$".
Figure 17:
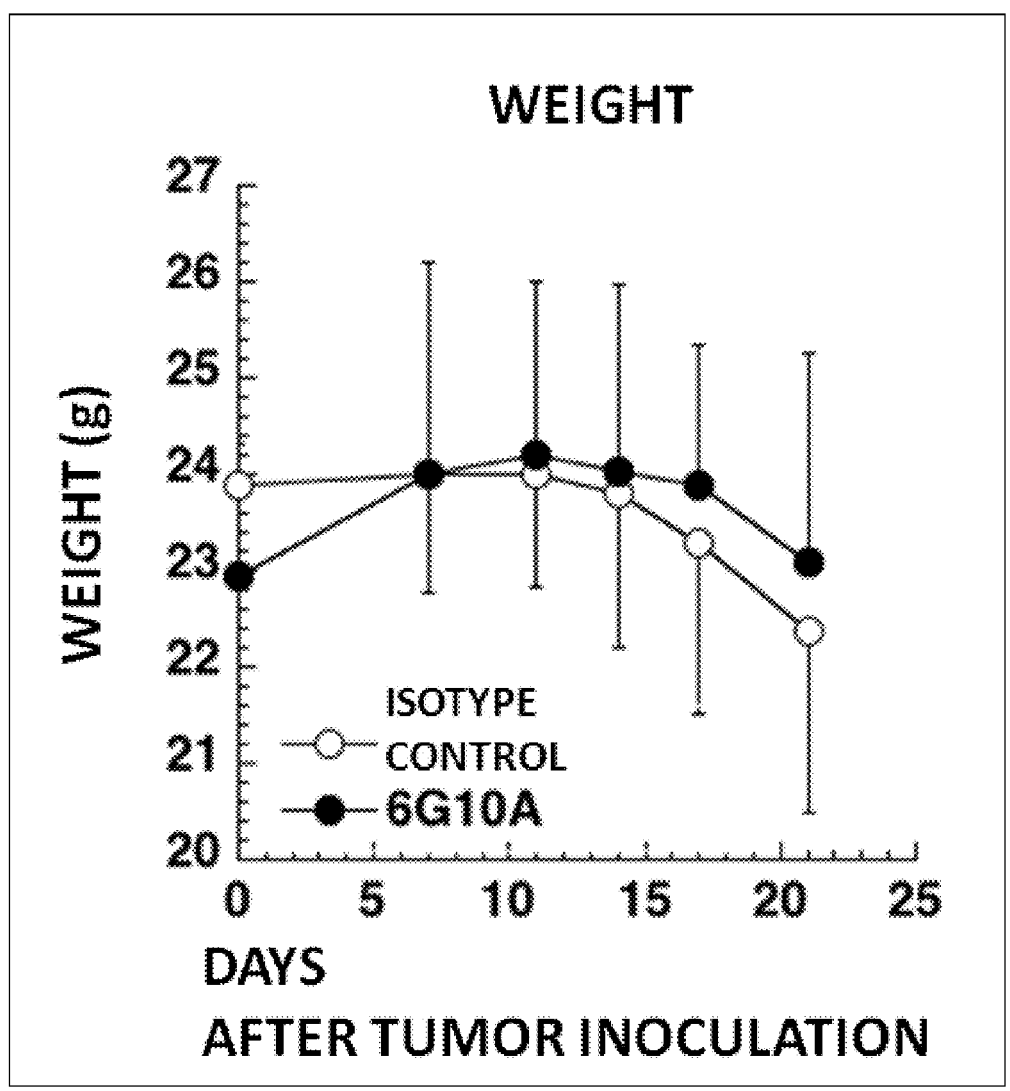
FIG. 17 is a graph for illustrating the result of analyzing the influence of the purified anti-CXADR antibody 6G10A administration on mice. Nude mice (male, n=3) were subcutaneously inoculated with the DU-145 cells. After 1 day, 7 days, and 14 days from the inoculation, 250 µg of 6G10A or the isotype control antibody was administered into the caudal veins. Then, the weight of the mice was measured after predetermined periods. The values of the weight represented by each polygonal line in the figure are each an average value ±SD of three mice in one group.
Figure 18:
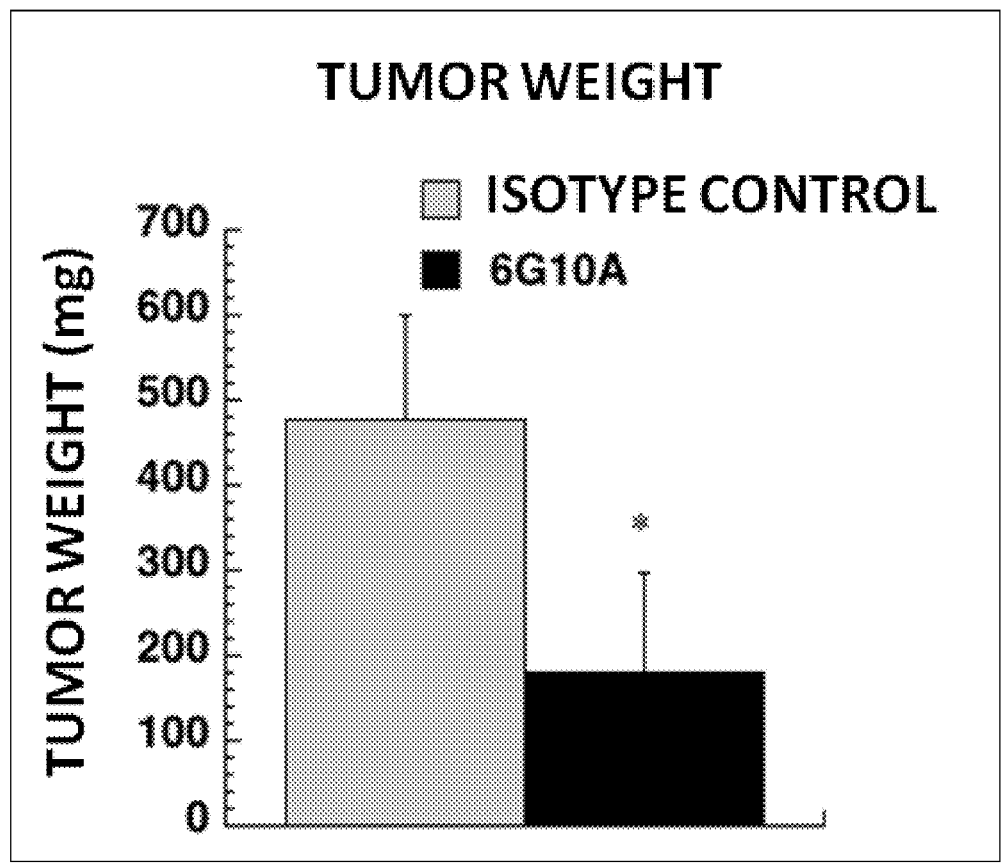
FIG. 18 is a graph for illustrating the result of analyzing the effect of the anti-CXADR antibody 6G10A on DU-145 tumor. The DU-145 cells were subcutaneously transplanted into nude mice (male, n=3). After 1 day, 7 days, and 14 days from the inoculation, 250 µg of 6G10A or the isotype control antibody was administered into the caudal veins. Then, the mice were sacrificed after 21 days from the cell inoculation, and tumors were resected therefrom to measure the weight. The value represented by each bar in the figure is an average value ±SD of three mice in one group. Moreover, "*" indicates "$P<0.05$".
Figure 19:
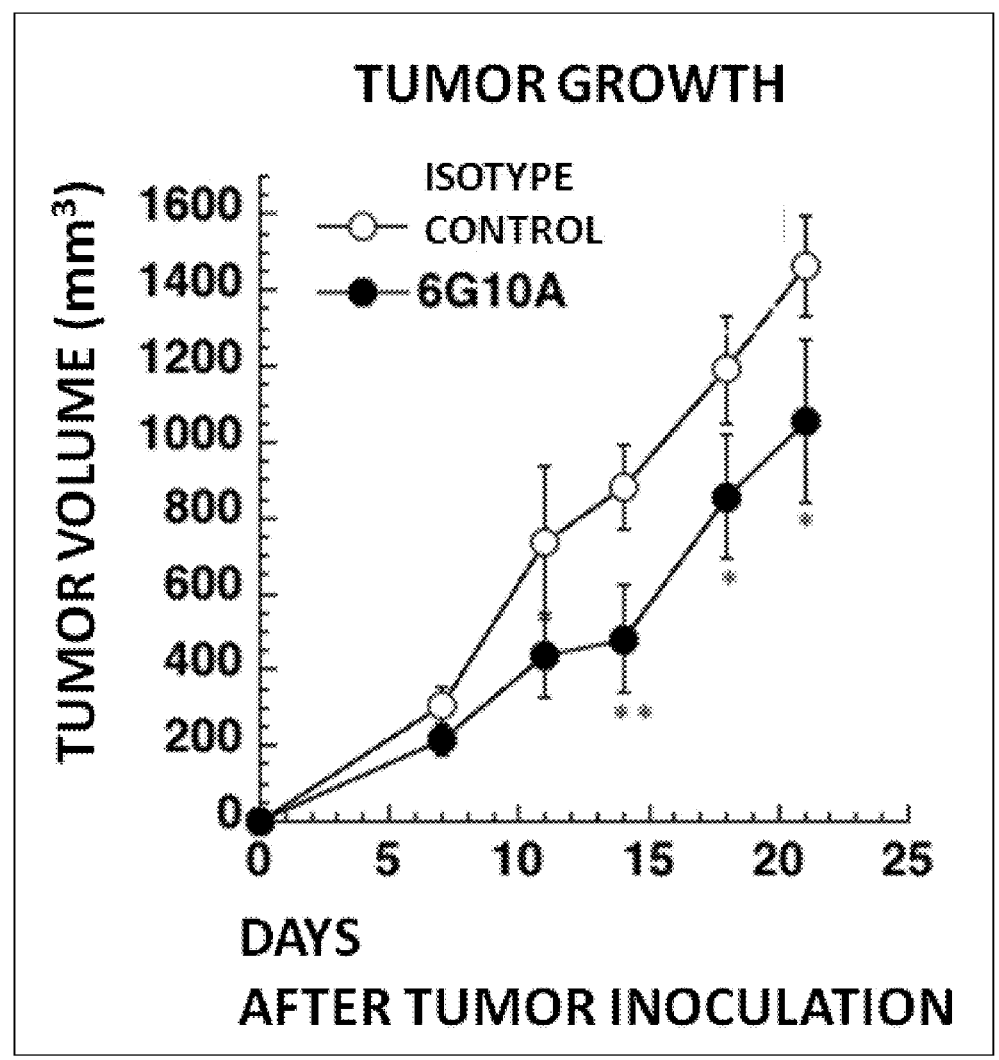
FIG. 19 is a graph for illustrating the result of analyzing the effect of the anti-CXADR antibody 6G10A on BxPC3 tumor. BxPC3 cells were subcutaneously transplanted into nude mice (male, n=4). After 1 day, 7 days, and 14 days from the inoculation, 250 µg of 6G10A or the isotype control antibody was administered into the caudal veins. Then, the diameter of tumors isolated from the mice after predetermined periods was measured to calculate the volumes. The values of the volumes represented by each polygonal line in the figure are each an average value ±SD of four mice in one group. Moreover, "*" indicates "$P<0.05$".
Figure 20:
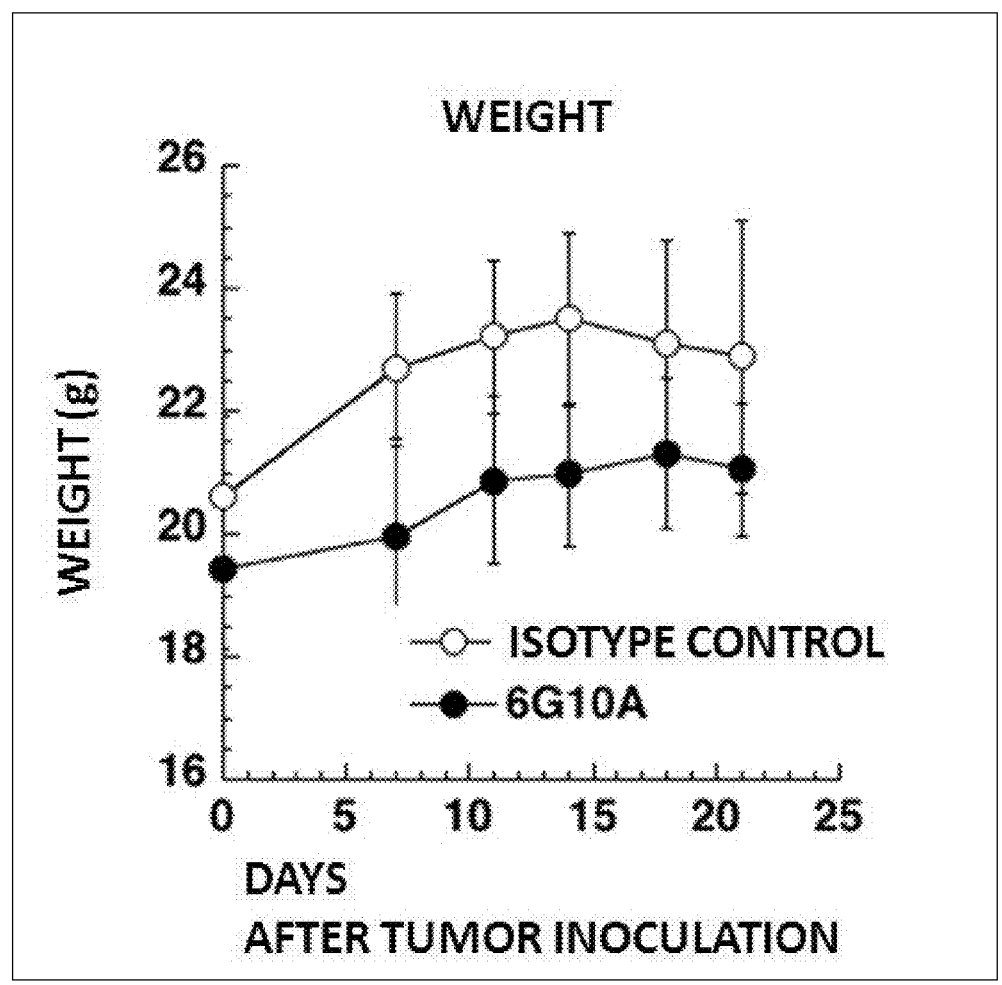
FIG. 20 is a graph for illustrating the result of analyzing the influence of the purified anti-CXADR antibody 6G10A administration on mice. Nude mice (male, n=4) were subcutaneously inoculated with the BxPC3 cells. After 1 day, 7 days, and 14 days from the inoculation, 250 µg of 6G10A or the isotype control antibody was administered into the caudal veins. Then, the weight of the mice was measured after predetermined periods. The values of the weight represented by each polygonal line in the figure are each an average value ±SD of four mice in one group.
Figure 21:
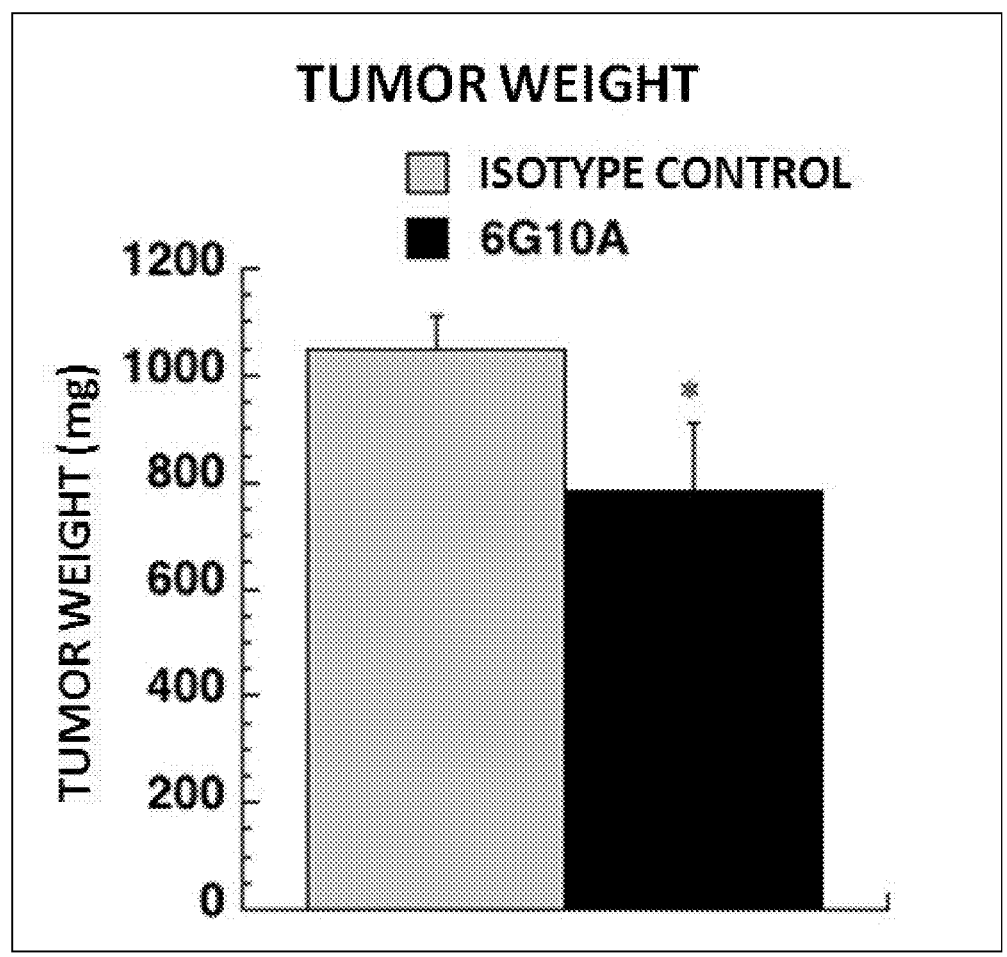
FIG. 21 is a graph for illustrating the result of analyzing the effect of the anti-CXADR antibody 6G10A on BxPC3 tumor. The BxPC3 cells were subcutaneously transplanted into nude mice (male, n=4). After 1 day, 7 days, and 14 days from the inoculation, 250 µg of 6G10A or the isotype control antibody was administered into the caudal veins. Then, the mice were sacrificed after 21 days from the cell inoculation, and tumors were resected therefrom to measure the weight. The value represented by each bar in the figure is an average value ±SD of four mice in one group. Moreover, "*" indicates "$P<0.05$".

Next, the anti-cancer activity in an orthotopic graft model obtained by transplanting the LNCaP-CR cells into the prostate of the mouse was examined. FIGS. 14 and 15 show the obtained result.

As shown in FIGS. 14 and 15, it was revealed that the intravenous administration at 250 µg/mouse once a week three times in total suppressed the growth of the LNCaP-CR prostate cancer in the mouse prostates significantly by approximately 90%.

Example 7

[In Vivo Cancer Suppressing Effect 3 of Purified Anti-CXADR Antibody]

Next, the anti-cancer activities against the androgen-independent human prostate cancer DU-145 cells and the human pancreatic cancer cells BxPC3 were examined. FIGS. 16 to 21 show the obtained result.

As shown in FIGS. 16 to 21, the intravenous administration of the 6G10A clone at 250 µg/mouse once a week three times in total suppressed the tumor growths of the DU-145 cells and the BxPC3 cells, which were subcutaneously transplanted into the mice, significantly by approximately 60% and approximately 25%, respectively.

Example 8

[In Vivo Cancer Suppressing Effect 4 of Purified Anti-CXADR Antibody]

Figure 22:
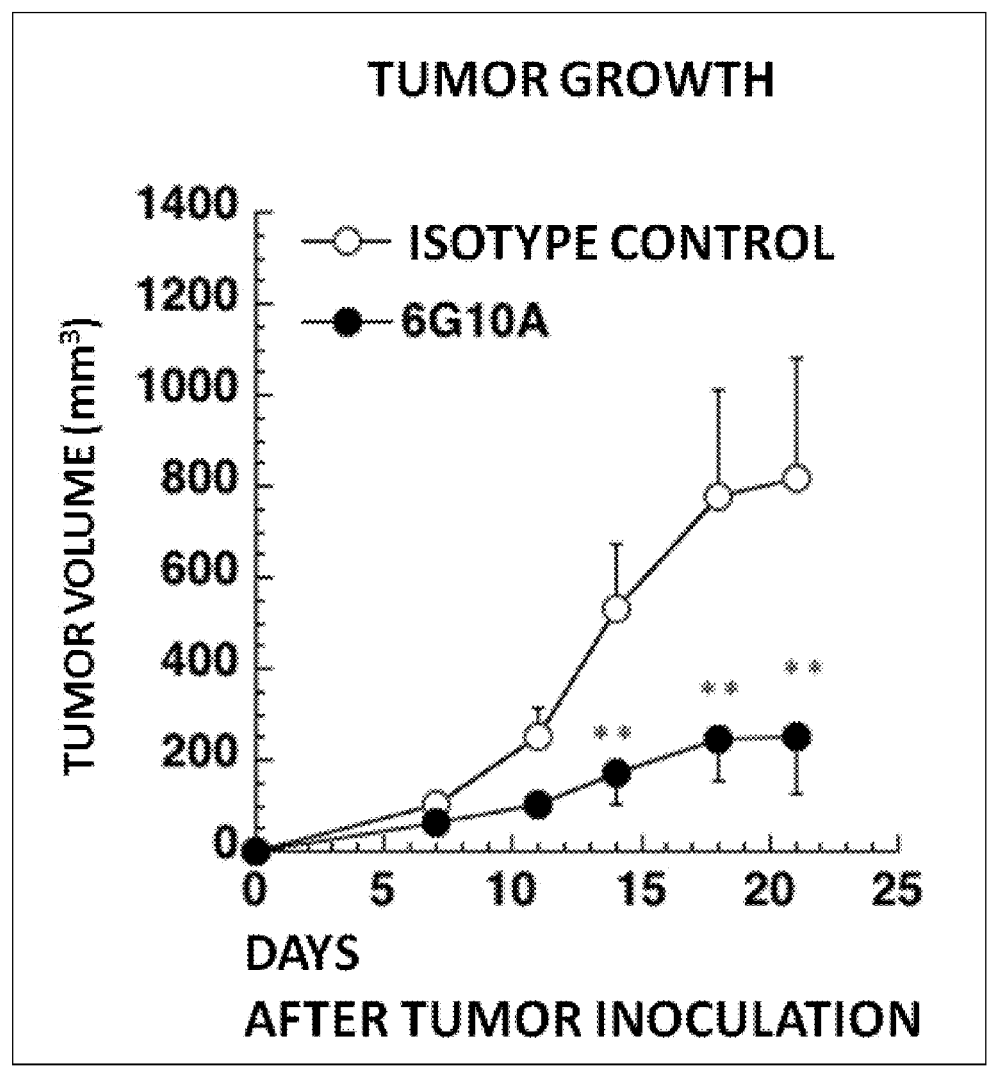
FIG. 22 is a graph for illustrating the result of analyzing the effect of the anti-CXADR antibody 6G10A on DLD-1 tumor. DLD-1 cells were subcutaneously transplanted into nude mice (male, n=3). After 1 day, 7 days, and 14 days from the inoculation, 250 µg of 6G10A or the isotype control antibody was administered into the caudal veins. Then, the diameter of tumors isolated from the mice after predetermined periods was measured to calculate the volumes. The values of the volumes represented by each polygonal line in the figure are each an average value ±SD of three mice in one group. Moreover, "**" indicates "$P<0.001$".
Figure 23:
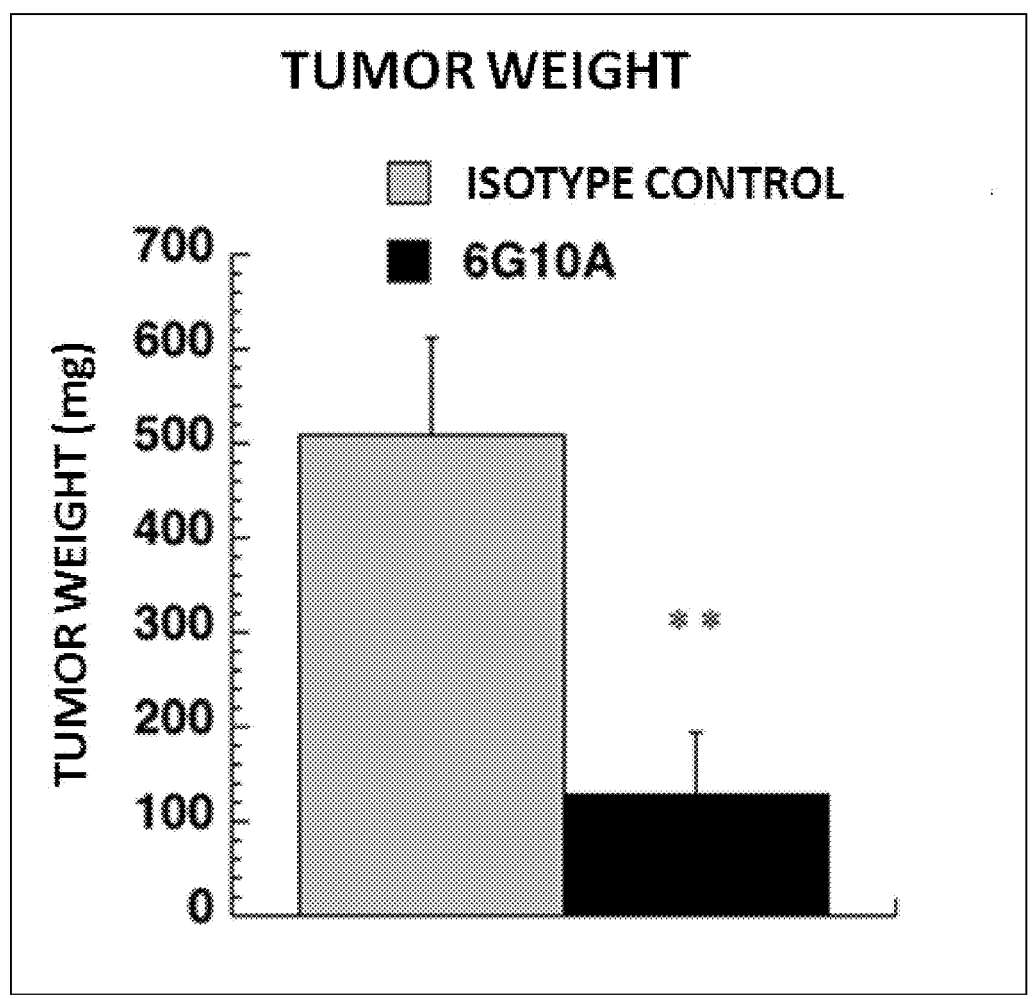
FIG. 23 is a graph for illustrating the result of analyzing the effect of the anti-CXADR antibody 6G10A on DLD-1 tumor. The DLD-1 cells were subcutaneously transplanted into nude mice (male, n=3). After 1 day, 7 days, and 14 days from the inoculation, 250 µg of 6G10A or the isotype control antibody was administered into the caudal veins. Then, the mice were sacrificed after 21 days from the cell inoculation, and tumors were resected therefrom to measure the weight. The value represented by each bar in the figure is an average value ±SD of three mice in one group. Moreover, "**" indicates "$P<0.001$".
Figure 24:
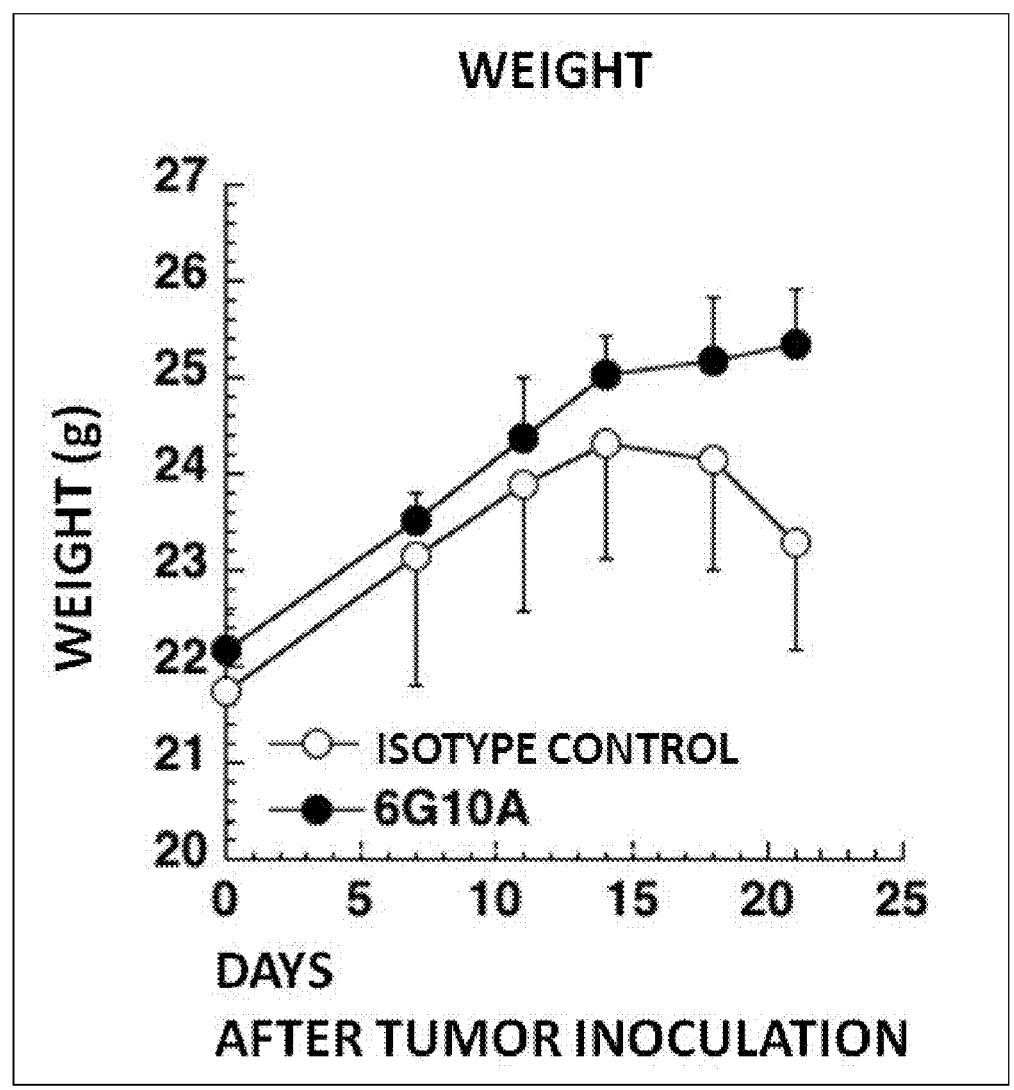
FIG. 24 is a graph for illustrating the result of analyzing the influence of the purified anti-CXADR antibody 6G10A administration on mice. Nude mice (male, n=3) were subcutaneously inoculated with the DLD-1 cells. After 1 day, 7 days, and 14 days from the inoculation, 250 µg of 6G10A or the isotype control antibody was administered into the caudal veins. Then, the weight of the mice was measured after predetermined periods. The values of the weight represented by each polygonal line in the figure are each an average value ±SD of three mice in one group.

The human colorectal cancer cells DLD-1 were subcutaneously transplanted into the nude mice, and the purified antibody was intravenously administered at 250 µg/mouse once a week three times in total to examine the anti-cancer activity of the antibody. FIGS. 22 to 24 show the obtained result.

As shown in FIG. 22, the intravenous administration of the 6G10A clone at 250 μg/mouse once a week three times in total significantly suppressed the tumor growth of the DLD-1 cells subcutaneously transplanted into the mice. Further, as shown in FIG. 23, it was revealed that the 6G10A clone was capable of significantly suppressing the DLD-1 tumor weight by approximately 70% on day 21. In addition, during this period, no toxicity to the mice such as weight loss was observed by the administration of the antibody clone (see FIG. 24).

Example 9

[Analysis 1 of Anti-Cancer Action Mechanism of Anti-CXADR Antibody]

Figure 25:
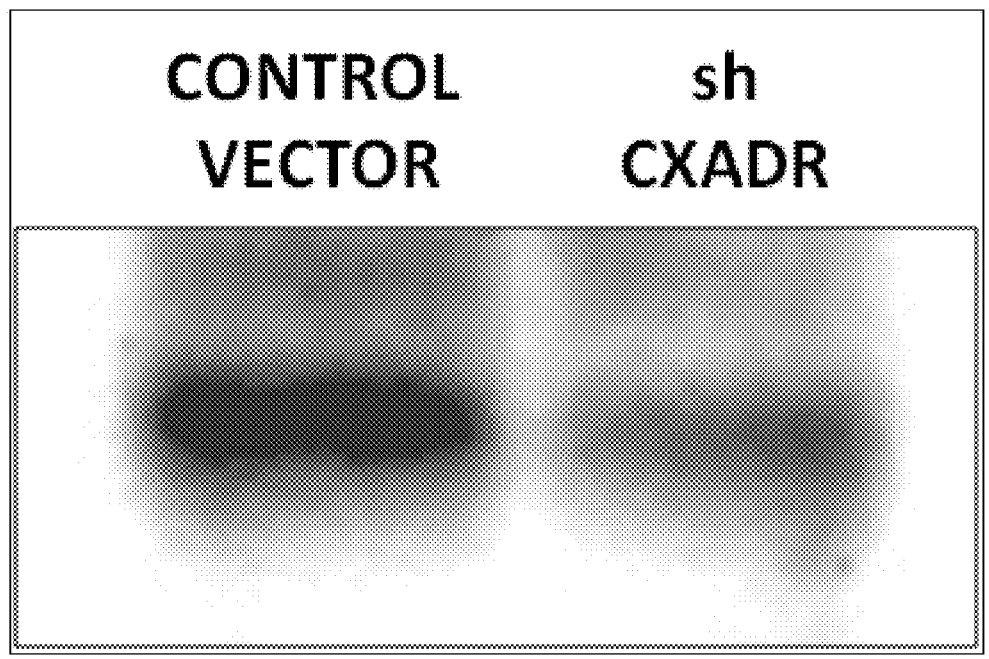
FIG. 25 is a photograph for illustrating the result of confirming by the Western blot that cells with a decreased CXADR expression were prepared by introducing a shRNA to the DU-145 cells. In the figure, "sh CXADR" shows the result of detecting the expression of the CXADR protein in the DU-145 cells having the shRNA against CXADR introduced, while "control vector" shows the result of detecting the expression of the CXADR protein in DU-145 cells having a control shRNA introduced.
Figure 26:
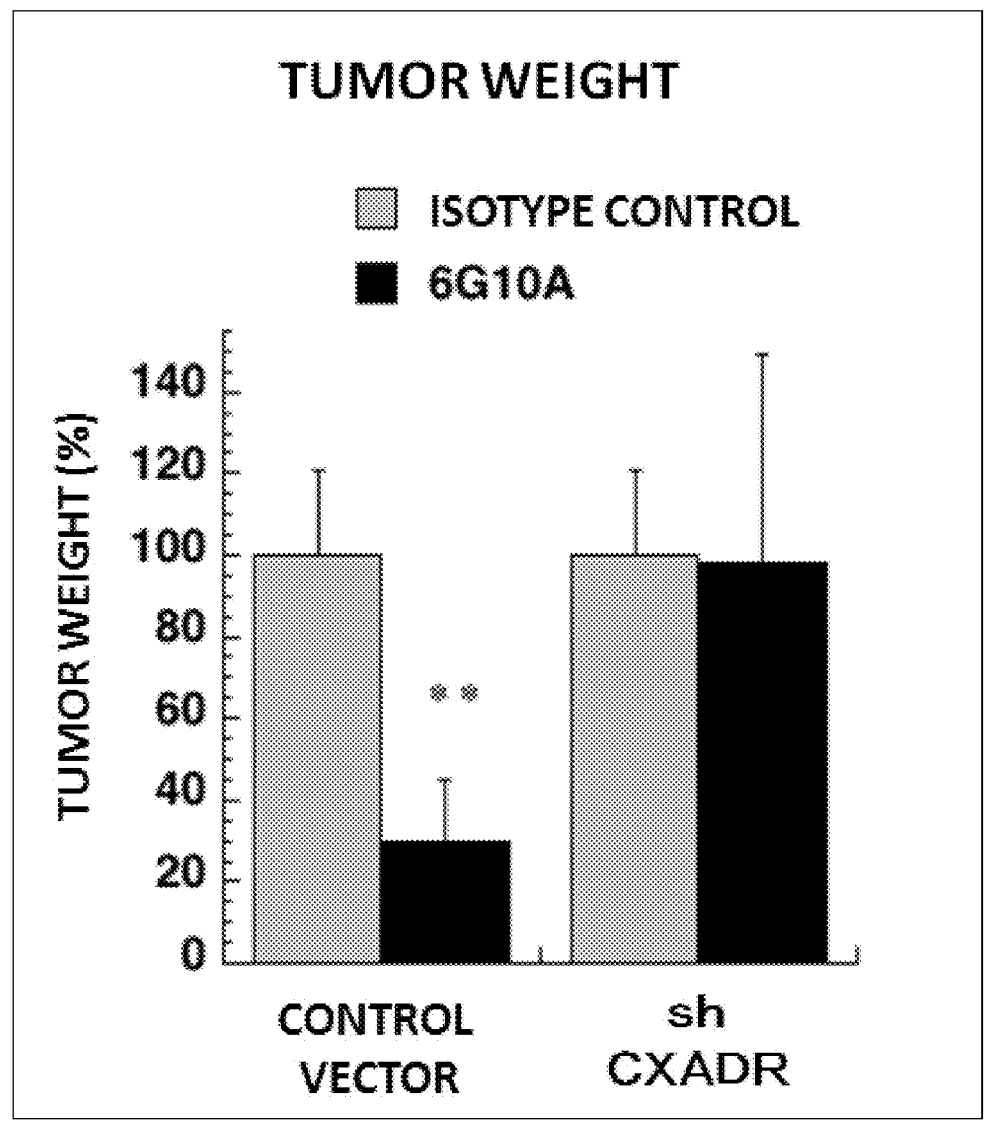
FIG. 26 is a graph for illustrating the result of analyzing the effect of the anti-CXADR antibody 6G10A on DU-145 tumor. The DU-145 cells in which the shRNA against CXADR or the control shRNA was introduced were subcutaneously transplanted into nude mice (male, n=3). After 1 day, 7 days, and 14 days from the inoculation, 250 µg of 6G10A or the isotype control antibody was administered into the caudal veins. Then, the mice were sacrificed after 21 days from the cell inoculation, and tumors were resected therefrom to measure the weight. The value represented by each bar in the figure is an average value ±SD of three mice in one group. Moreover, "*" indicates "P<0.001". In addition, "sh CXADR" shows the result of the mice inoculated with the DU-145 cells having the shRNA against CXADR introduced, while "control vector" shows the result of the mice inoculated with the DU-145 cells having the control shRNA introduced.

Cells with a decreased CXADR expression (CXADR shRNA-introduced cells) were prepared by introducing to the DU-145 cells a shRNA-expressing vector, the shRNA targeting the human CXADR gene. Moreover, DU-145 cells having a control vector introduced were also prepared (see FIG. 25). Then, these cells were respectively transplanted into the nude mice, and the purified anti-CXADR antibody (6G10A clone) was intravenously administered at 250 μg/mouse once a week three times in total to examine the anti-cancer activity of the antibody. FIG. 26 shows the obtained result.

As apparent from the result shown in FIG. 26, the tumor of the cells having the control vector introduced was decreased by approximately 70% and thus significantly inhibited by 6G10A. However, 6G10A did not exhibit a remarkable anti-cancer activity against the cells with a decreased CXADR expression.

Thus, it was verified that the in vivo cancer suppressing effect of the anti-CXADR antibody of the present invention, which was revealed in Example 7 and so forth, was demonstrated when the antibody bound to CXADR; in other words, the antibody of the present invention was capable of exhibiting the cancer suppressing effect on a cancer expressing the CXADR protein.

Example 10

[Analysis 2 of Anti-Cancer Action Mechanism of Anti-CXADR Antibody]

Figure 27:
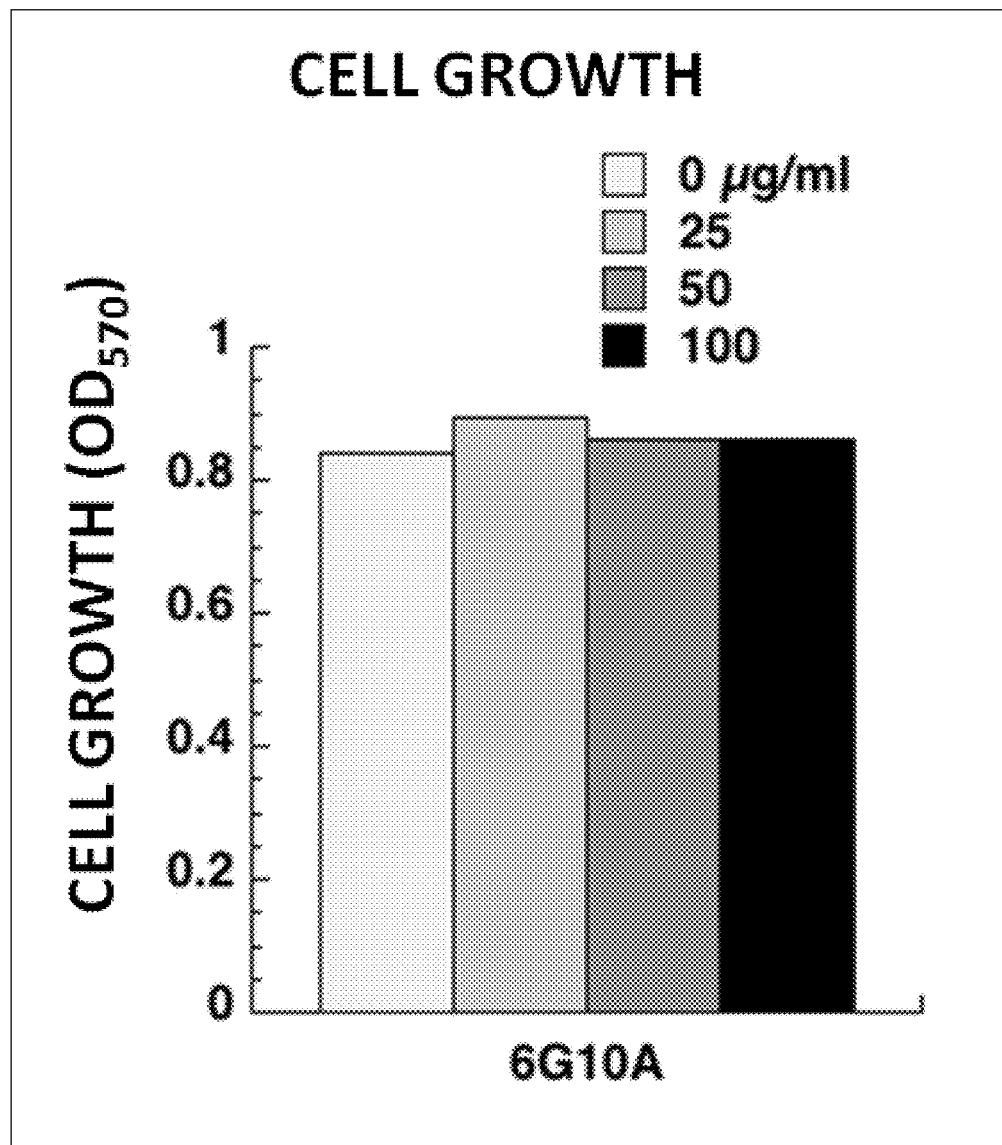
FIG. 27 is a graph for illustrating the result of analyzing the influence of the anti-CXADR antibody 6G10A on cell growth. In the figure, the vertical axis represents the number of cells counted (absorbance at 570 nm) by the MTT method after the LNCaP-CR cells were cultured in the presence of 6G10A for 3 days. Moreover, the value represented by each bar in the figure indicates an average value of two-replicate measurement values, and the standard error (SE) is 10% or less.
Figure 28:
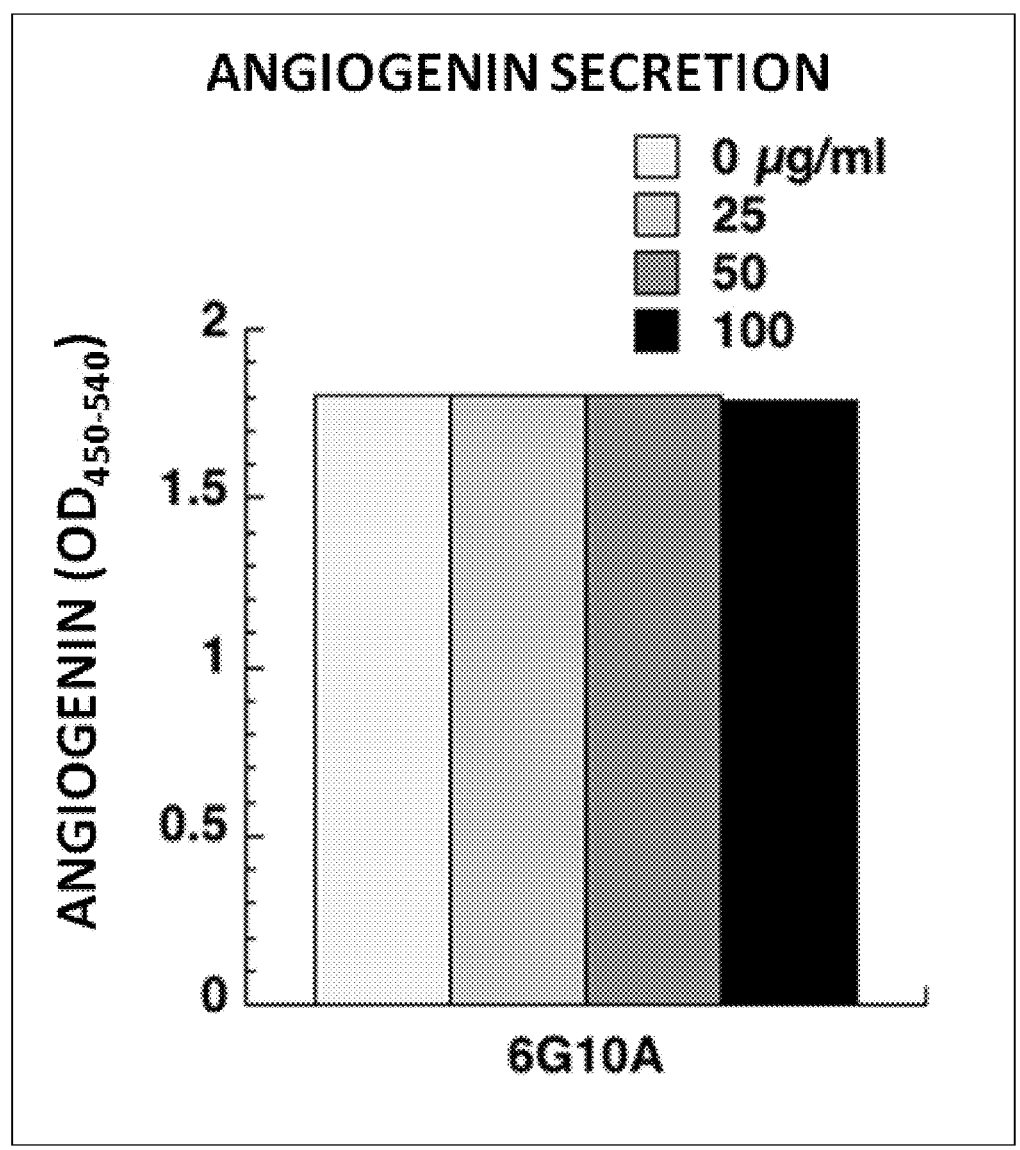
FIG. 28 is a graph for illustrating the result of analyzing the influence of the anti-CXADR antibody 6G10A on angiogenin production. In the figure, the vertical axis represents the amount of angiogenin produced in the culture supernatant, the amount being measured (absorbance at 450-540 nm) by the ELISA method after the LNCaP-CR cells were cultured in the presence of 6G10A for 3 days. Moreover, the value represented by each bar in the figure indicates an average value of two-replicate measurement values, and the standard error (SE) is 10% or less.

The purified antibody clone which had exhibited the anti-cancer activity in the mouse xenograft model was examined for the in vitro influences on the growth of the LNCaP-CR cells and the angiogenin production. Nevertheless, no change was observed at all (see FIGS. 27 and 28).

Figure 30:
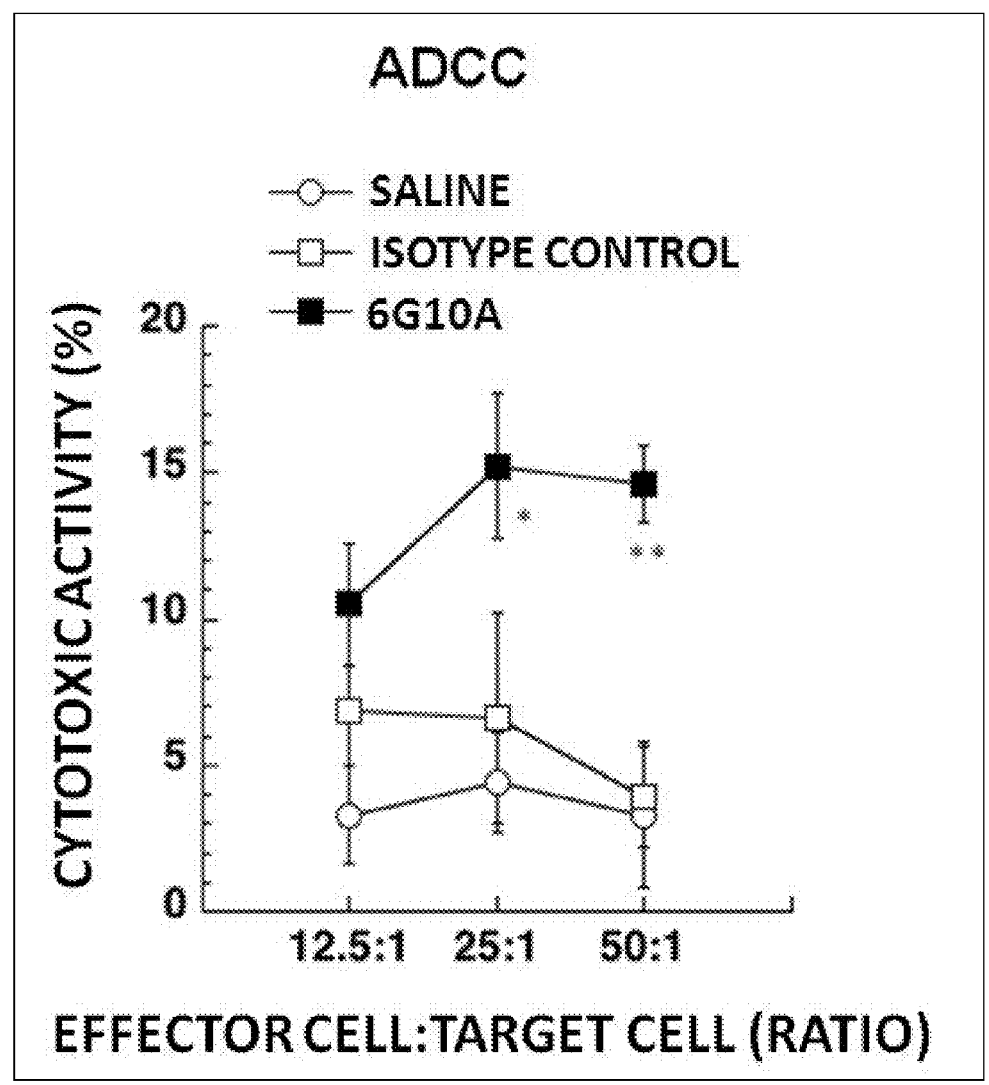
FIG. 30 is a graph for illustrating the result of analyzing the ADCC activity of the anti-CXADR antibody 6G10A. The ADCC activity was examined as follows. Spleen cells (effector cells) of a nude mouse (male) and DU-145 cells (target cells) labelled with calcein AM were cultured in the presence of 100 μg/ml of 6G10A or the isotype control antibody, or a saline for 4 hours. Then, the fluorescence intensity of calcein AM in the culture supernatant was measured, and the cytotoxic activity (lysis activity) against the DU-145 cells was calculated. The values of the cytotoxic activity represented by each polygonal line in the figure are each an average value ±SD of three-replicate measurement values. "*" indicates "P<0.05", and "**" indicates "P<0.01".
Figure 31:
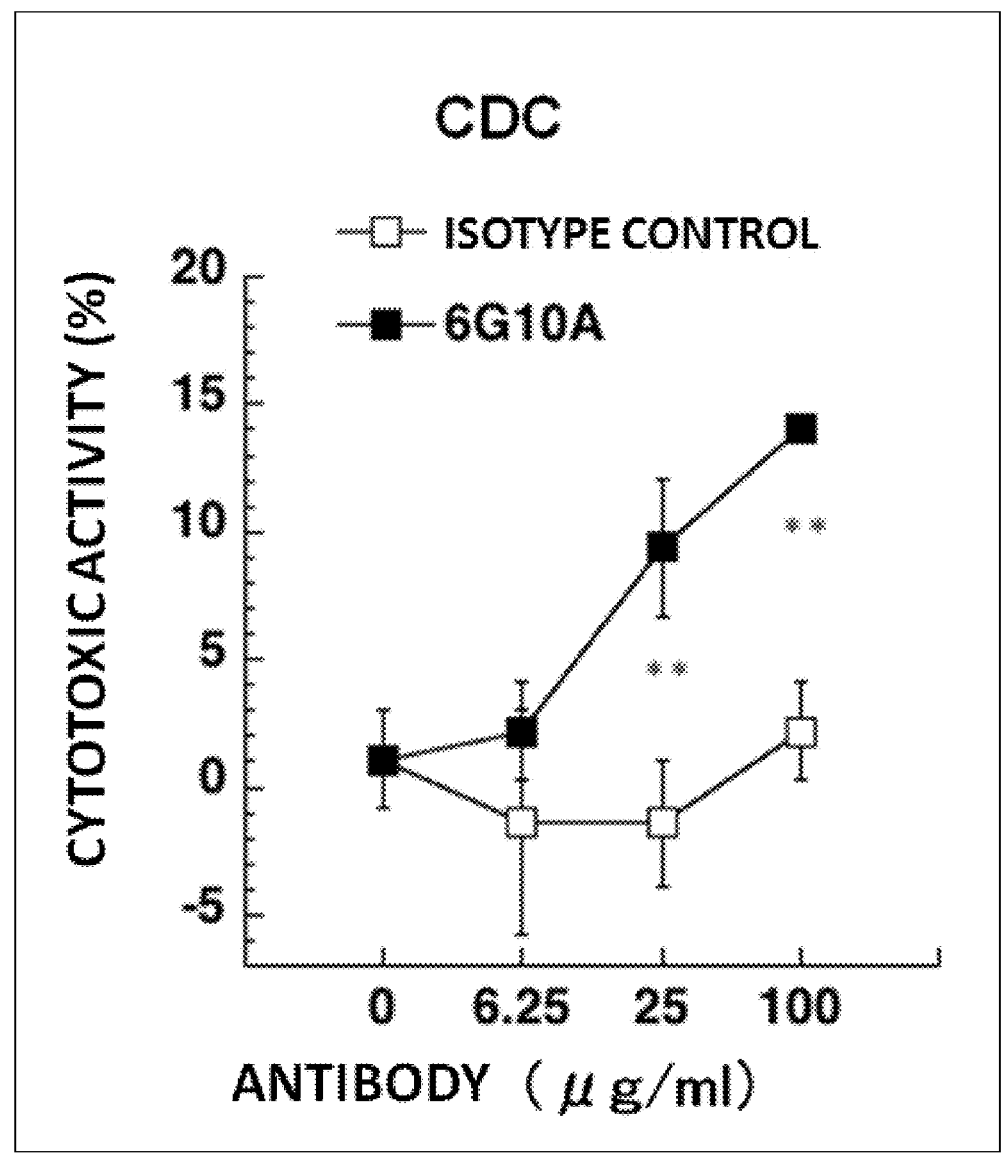
FIG. 31 is a graph for illustrating the result of analyzing the CDC activity of the anti-CXADR antibody 6G10A. The CDC activity was examined as follows. DU-145 cells labelled with calcein AM and 6G10A or the isotype control antibody were cultured in the presence of 10% complement for 4 hours. Then, the fluorescence intensity of calcein AM in the culture supernatant was measured, and the cytotoxic activity (lysis activity) against the DU-145 cells was calculated. The values of the cytotoxic activity represented by each polygonal line in the figure are each an average value ±SD of three-replicate measurement values. "**" indicates "P<0.01".

Generally, the in vivo anti-cancer activity of an antibody is demonstrated by neutralizing or inhibiting the function of a target molecule, or the ADCC activity or CDC activity of the antibody. Since no in vitro effect was demonstrated on such as the cell growth and the protein production, the ADCC activity and the CDC activity were examined. Note that although unillustrated, the LNCaP-CR cells were not suitable for the analysis of the ADCC activity and the CDC activity. For this reason, the androgen-independent human prostate cancer cells: DU-145 cells were used. FIGS. 30 and 31 show the obtained results.

Figure 29:
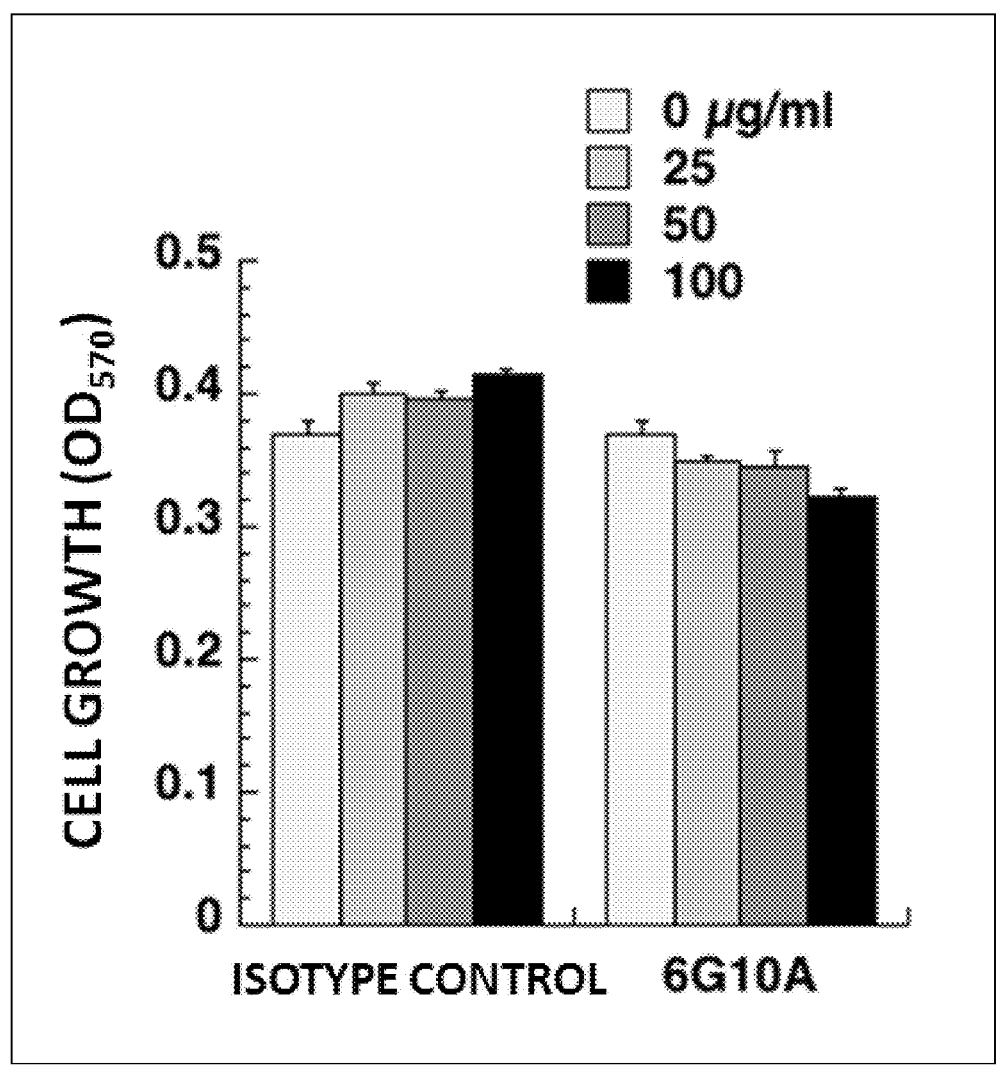
FIG. 29 is a graph for illustrating the result of analyzing the influence of the anti-CXADR antibody 6G10A on cell growth. In the figure, the vertical axis represents the number of cells counted (absorbance at 570 nm) by the MTT method after DU-145 cells were cultured in the presence of 6G10A for 3 days. Moreover, the value represented by each bar in the figure is an average value ±SD of three-replicate measurement values.

As in the case of the LNCaP-CR cells, 6G10A had no in vitro influence on the growth of the DU-145 cells at all (see FIG. 29). In contrast, as shown in FIGS. 30 and 31, it was found that 6G10A exhibited an ADCC activity and a CDC activity against the DU-145 cells.

Figure 32:
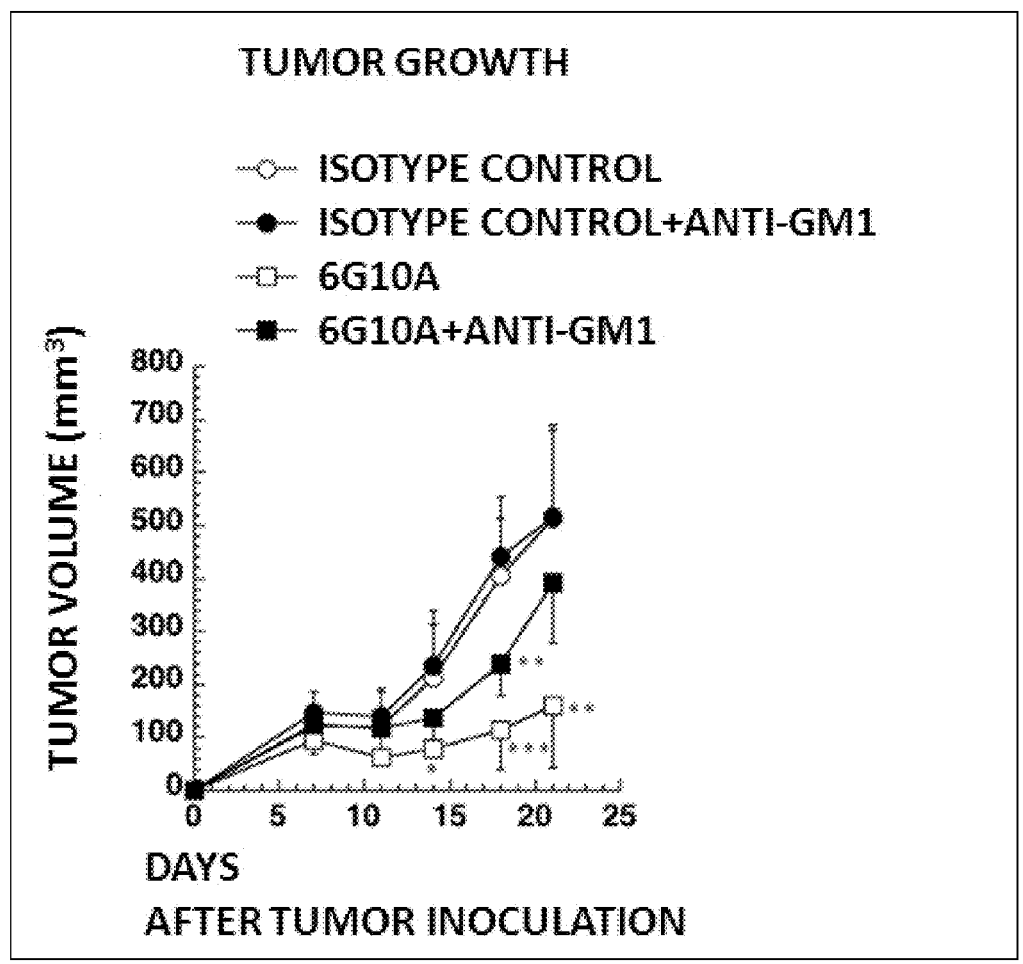
FIG. 32 is a graph for illustrating the result of analyzing the influence of an anti-asialo GM1 antibody on the anti-cancer activity of the anti-CXADR antibody 6G10A. The DU-145 cells were subcutaneously transplanted into nude mice (male, n=5). After 0 days, 7 days, and 14 days from the inoculation, 250 μg of 6G10A or the isotype control antibody was administered into the caudal veins. The anti-asialo GM1 antibody (anti-GM1), 100 μg, was administered into the caudal veins on the day before the cell inoculation, and on day 6 and day 13 after the cell inoculation. Then, the diameter of tumors isolated from the mice after predetermined periods was measured to calculate the volumes. The values of the volumes represented by each polygonal line in the figure are each an average value ±SD of five mice in one group. Moreover, "" indicates "P<0.01", and "*" indicates "P<0.001".
Figure 33:
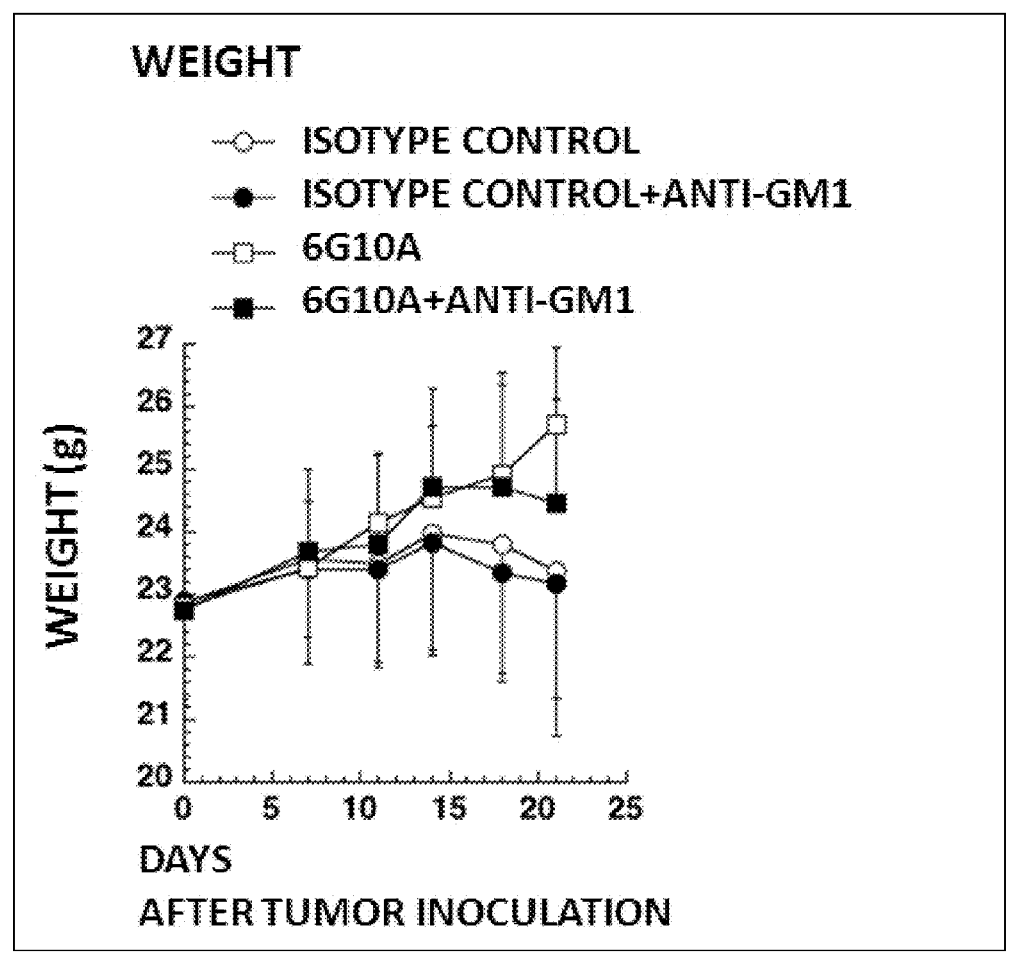
FIG. 33 is a graph for illustrating the result of analyzing the influence of the anti-CXADR antibody 6G10A and the anti-asialo GM1 administration on mice. The DU-145 cells were subcutaneously transplanted into nude mice (male, n=5). After 0 days, 7 days, and 14 days from the inoculation, 250 μg of 6G10A or the isotype control antibody was administered into the caudal veins. The anti-asialo GM1 antibody (anti-GM1), 100 μg, was administered into the caudal veins on the day before the cell inoculation, and on day 6 and day 13 after the cell inoculation. Then, the weight of the mice was measured after predetermined periods. The values of the weight represented by each polygonal line in the figure are each an average value ±SD of five mice in one group.
Figure 34:
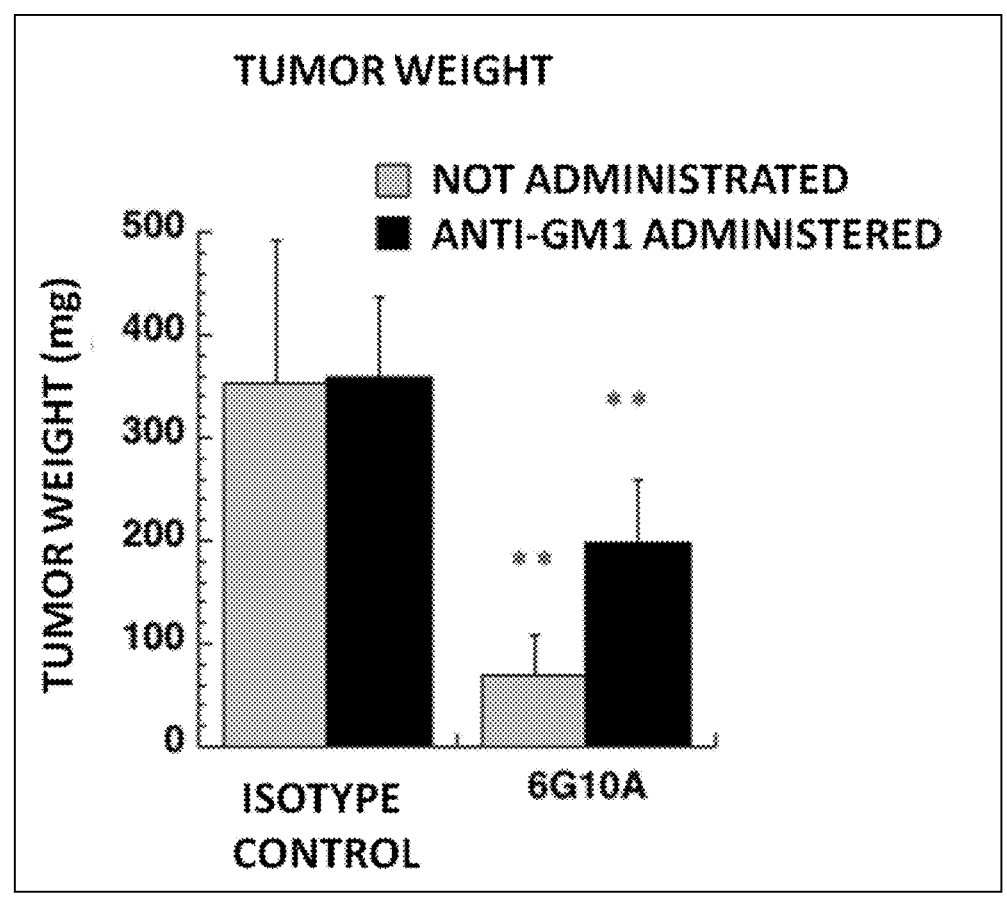
FIG. 34 is a graph for illustrating the result of analyzing the influence of the anti-asialo GM1 antibody on the anti-cancer activity of the anti-CXADR antibody 6G10A. The DU-145 cells were subcutaneously transplanted into nude mice (male, n=5). After 0 days, 7 days, and 14 days from the inoculation, 250 μg of 6G10A or the isotype control antibody was administered into the caudal veins. The anti-asialo GM1 antibody (anti-GM1), 100 μg, was administered into the caudal veins on the day before the cell inoculation, and on day 6 and day 13 after the cell inoculation. Then, the mice were sacrificed after 21 days from the cell inoculation, and tumors were resected therefrom to measure the weight. The value represented by each bar in the figure is an average value ±SD of five mice in one group. Moreover, "**" indicates "P<0.01".

Hence, in order to verify that the CDC activity and the ADCC activity were actually involved in the in vivo anti-cancer activity, the examination was conducted using mice to which the anti-asialo GM1 antibody was administered to remove NK cells where the ADCC activity was mainly demonstrated. FIGS. 32 to 34 show the obtained result.

As shown in FIGS. 32 to 34, it was revealed that the administration of the anti-asialo GM1 antibody significantly weakened the anti-cancer activity of 6G10A. Because the anti-cancer activity was not completely lost by removing the NK-cells, it is conceivable that 6G10A exhibits the anti-cancer activity by both actions of the ADCC activity and the CDC activity.

Example 11

[Determination of Antibody Variable Region]

Of the 6G10A and 7F8A antibodies confirmed to have functions such as an anti-cancer activity in Examples 1 to 8, the sequences of heavy and light chains were determined, and the variable regions and CDRs were determined. FIGS. 35 and 36 show the obtained result regarding the sequence of 6G10A. FIGS. 37 and 38 show the obtained result regarding the sequence of 7F8A.

In addition, the base sequence of the variable region of the light chain of the anti-CXADR antibody 6G10A thus determined is shown in SEQ ID NO: 4, and the amino acid sequence thereof is shown in SEQ ID NO: 5. The base sequence of the variable region of the heavy chain is shown in SEQ ID NO: 9, and the amino acid sequence thereof is shown in SEQ ID NO: 10. Further, the amino acid sequences of CDR1, CDR2, and CDR3 of the light chain of the anti-CXADR antibody 6G10A are shown in SEQ ID NOs: 1 to 3. The amino acid sequences of CDR1, CDR2, and CDR3 of the heavy chain are shown in SEQ ID NOs: 6 to 8.

Additionally, the base sequence of the variable region of the light chain of the anti-CXADR antibody 7F8A thus determined is shown in SEQ ID NO: 14, and the amino acid sequence thereof is shown in SEQ ID NO: 15. The base sequence of the variable region of the heavy chain is shown in SEQ ID NO: 19, and the amino acid sequence thereof is shown in SEQ ID NO: 20. Further, the amino acid sequences of CDR1, CDR2, and CDR3 of the light chain of the anti-CXADR antibody 7F8A are shown in SEQ ID NOs: 11 to 13. The amino acid sequences of CDR1, CDR2, and CDR3 of the heavy chain are shown in SEQ ID NOs: 16 to 18.

Example 12

[Epitope Analysis]

Figure 39:
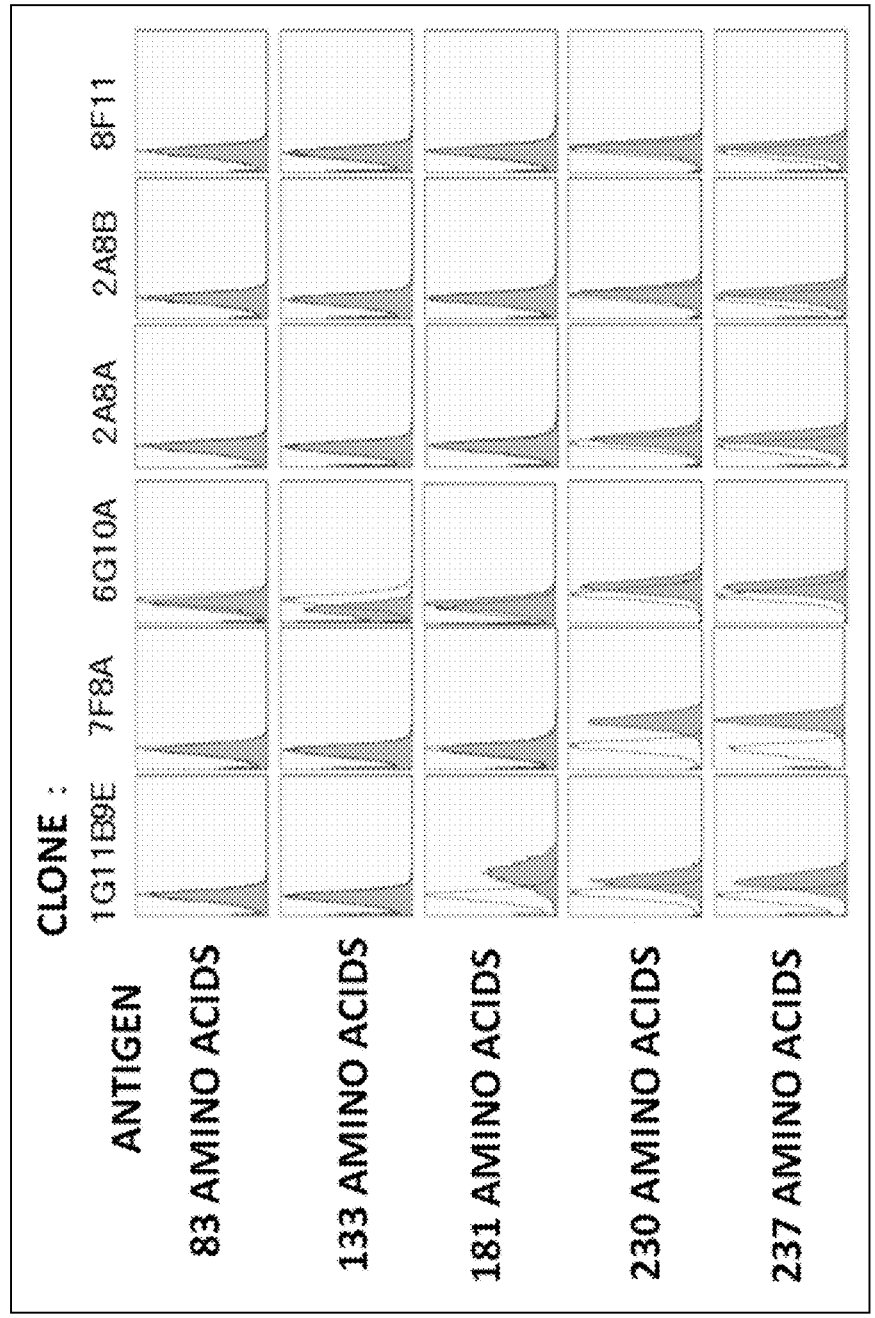
FIG. 39 shows graphs for illustrating the result of analyzing with the flow cytometer the reactivity between the anti-CXADR antibody produced from the hybridoma (clone name: 1G11B9E, 7F8A, 6G10A, 2A8A, 2A8B, or 8F11) and a CXADR extracellular region (83 amino acids from the N terminus, 133 amino acids from the N terminus, 181 amino acids from the N terminus, 230 amino acids from the N terminus, or 237 amino acid from the N terminus (full length of the CXADR extracellular region). A filled histogram part in each flow cytometer data illustrates the reaction with the anti-CXADR antibody produced from the corresponding hybridoma, whereas a white histogram part illustrates a reaction with a negative control mouse IgG (mixture of isotype control antibodies).

The epitope was determined by constructing cells expressing fragments of 83 amino acids, 133 amino acids, 181 amino acids, 230 amino acids, and 237 amino acids (full length of extracellular region) from the N-terminal side of the extracellular region of the CXADR protein, and then checking whether cells deficient in any of these regions would not react with the antibodies (6G10A, 7F8A). FIG. 39 shows the obtained result.

As shown in FIG. 39, it was revealed that 6G10A and 7F8A recognized the region from the 181st amino acid to the 230th amino acid as the epitope. Moreover, the analysis for epitope was similarly conducted also for four other antibody clones which stably had an activity but had no function in the in vivo studies (1G11B9E, 2A8A, 2A8B, and 8F11). As a result, the clone 1G11B9E was revealed to recognize the region from the 134th amino acid to the 180th amino acid as the epitope. The clones 2A8A, 2A8B, and 8F11 were revealed to recognize the region from the 231st amino acid to the 237th amino acid as the epitope. Thus, these results revealed that the 181st to the 230 amino acids recognized by 6G10A and 7F8A as the epitope are important sites having an anti-cancer action.

Example 13

[Reactivity with HUVEC]

Figure 40:
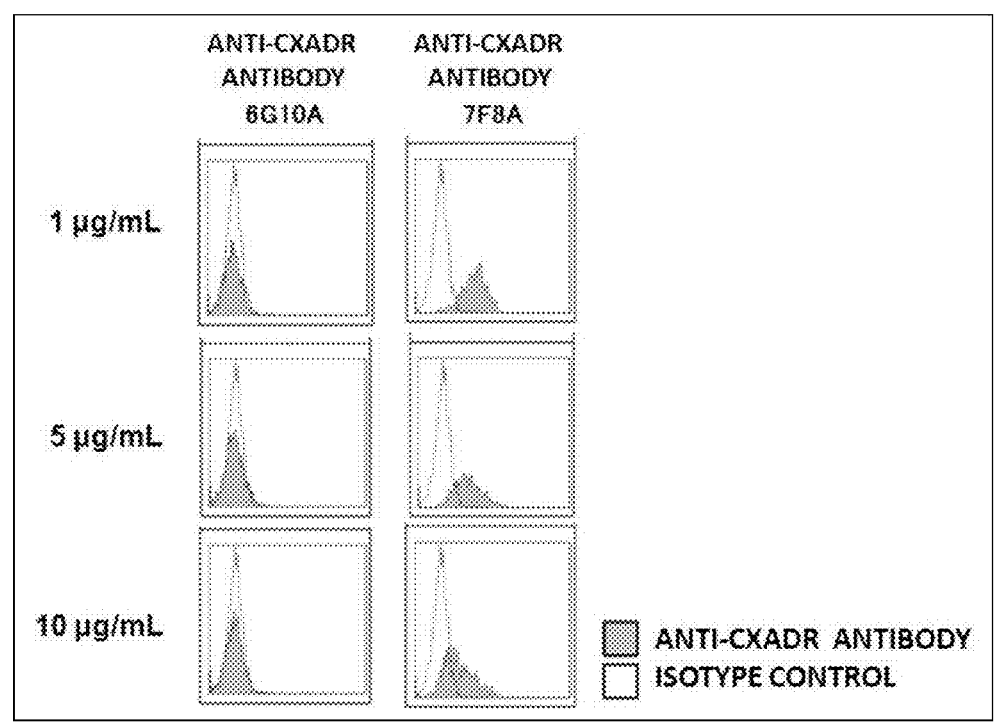
FIG. 40 shows graphs for illustrating the result of analyzing with the flow cytometer the reactivity between the anti-CXADR antibody 6G10A or 7F8A and human umbilical vein endothelial cells (HUVEC). A filled histogram part in each flow cytometer data illustrates the reaction with the anti-CXADR antibody, whereas a white histogram part illustrates a reaction with a negative control mouse IgG2a or IgG2b (isotype control antibody).
Figure 41:
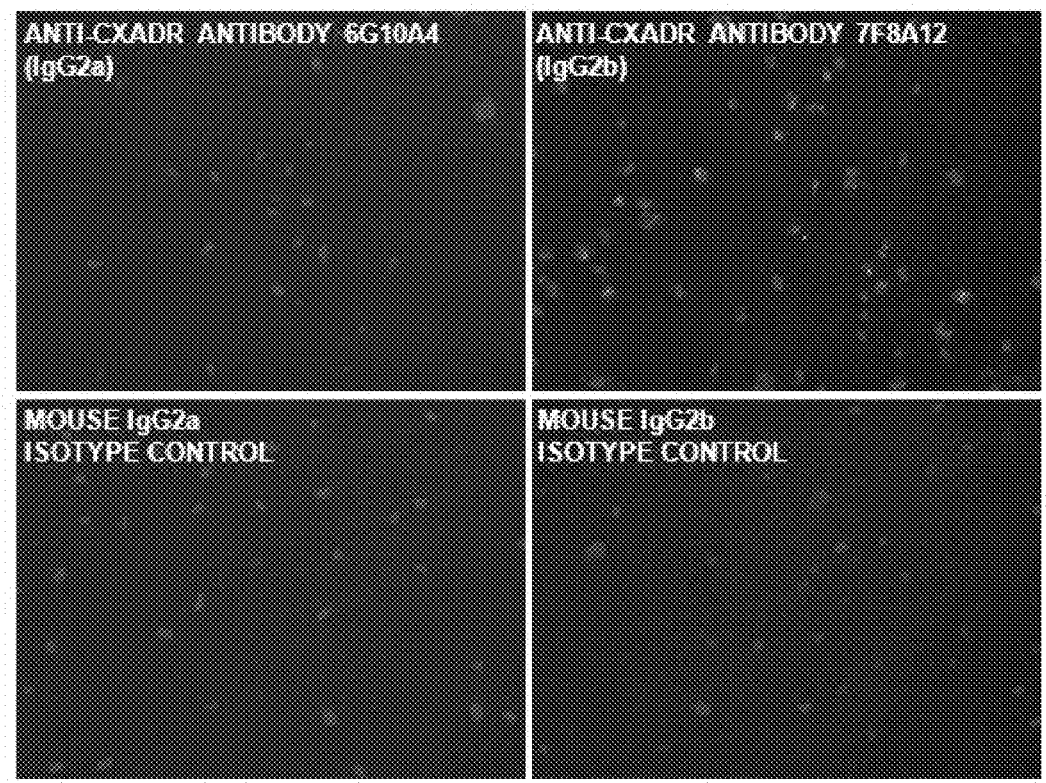
FIG. 41 shows micrographs for illustrating the result of analyzing the reactivity between the anti-CXADR antibody 6G10A or 7F8A and HUVEC by cell immunostaining.

Assuming an antibody drug administration by intravenous injection, the reactivity with human umbilical vein endothelial cells was examined by the flow cytometry method and cell staining method. HUVEC were used as the human umbilical vein endothelial cells. FIGS. 40 and 41 show the obtained result.

As shown in FIGS. 40 and 41, it was revealed that 6G10A did not react with HUVEC, but 7F8A reacted with HUVEC. By taking the reactivity with HUVEC into consideration, 6G10A seems to be more useful as antibody drug seeds.

Example 14

[Reactivity of Anti-CXADR Antibody of the Present Invention with Cancer Cells]

Figure 42:
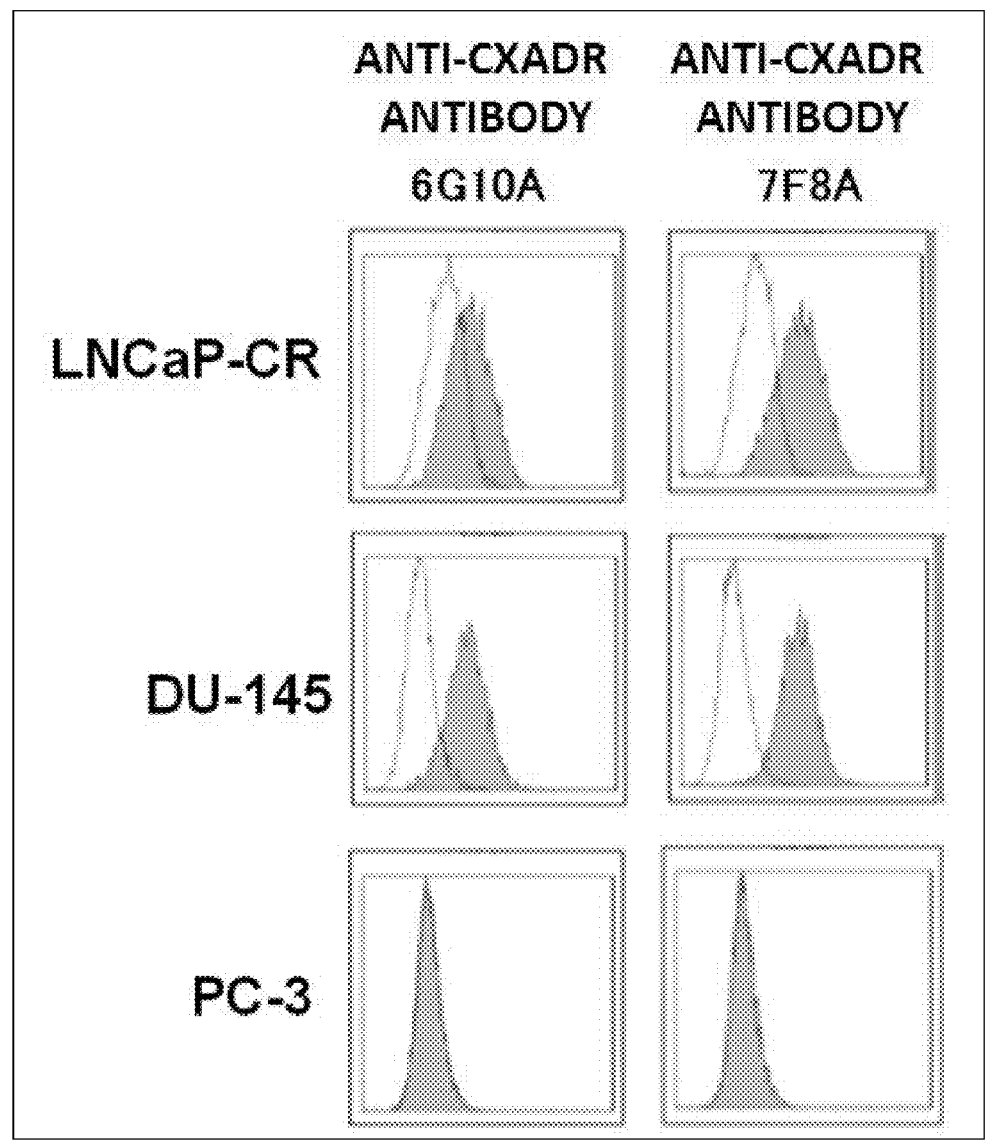
FIG. 42 shows graphs for illustrating the result of analyzing with the flow cytometer the reactivity between the anti-CXADR antibody 6G10 or 7F8A and various cancer cells (LNCaP-CR, DU-145, or PC-3). A filled histogram part in each flow cytometer data illustrates the reaction with the anti-CXADR antibody, whereas a white histogram part illustrates a reaction with a negative control mouse IgG2a or IgG2b (isotype control antibody).
Figure 43:
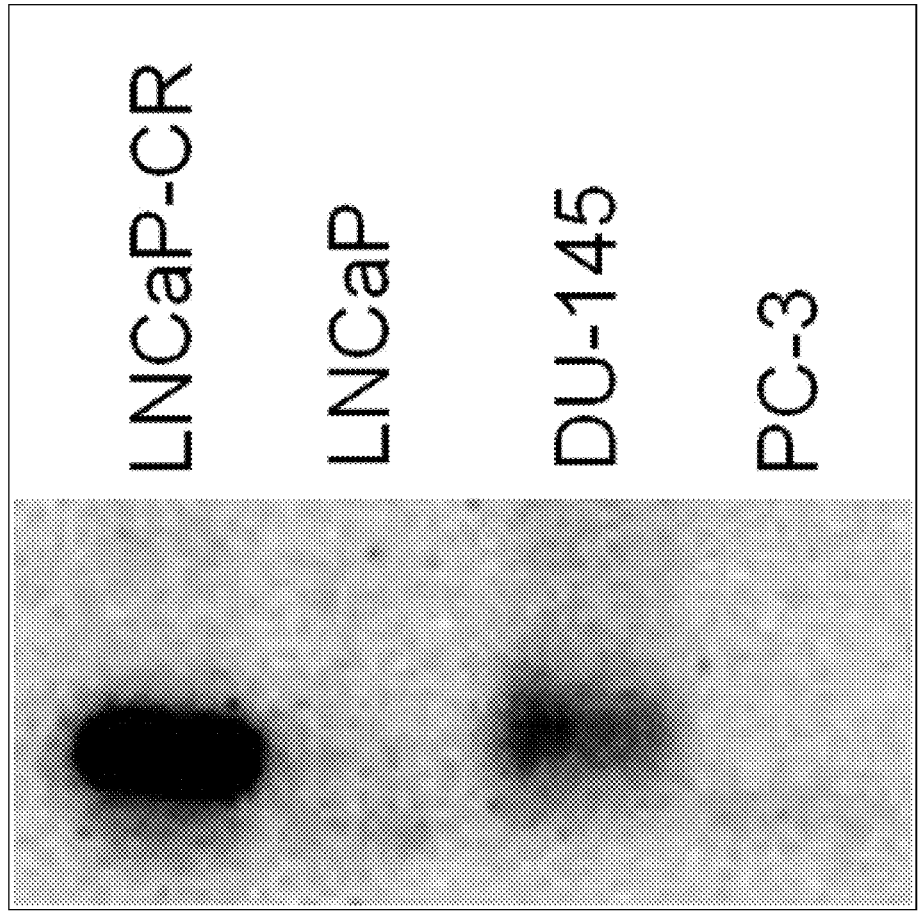
FIG. 43 is a photograph for illustrating the result of analyzing the expression of the CXADR protein in various cancer cells (LNCaP-CR, LNCaP, DU-145, or PC-3) by Western blotting.

The reactivity of the anti-CXADR antibody of the present invention with prostate cancer cells was examined by the flow cytometry method. FIG. 42 shows the obtained result. Note that the expression of CXADR in the prostate cancer cells was analyzed by the Western blotting method using an anti-CXADR antibody (manufactured by Sigma-Aldrich Co., HPA003342). FIG. 43 shows the obtained result.

As shown in FIGS. 42 and 43, it was revealed that, in the prostate cancer, the anti-CXADR antibody of the present invention reacted with the LNCaP-CR cells and the Du145 cells against which the anti-cancer activity was demonstrated in vivo. On the other hand, it was also revealed that CXADR was not expressed in PC-3 against which no anti-cancer activity was observed in vivo, and that PC-3 and the anti-CXADR antibody of the present invention did not react with each other.

INDUSTRIAL APPLICABILITY

As described above, the antibody of the present invention becomes capable of exhibiting excellent anti-cancer activity and so forth in vivo by binding to the epitope present at the positions 181 to 230 of the CXADR protein derived from human. Thus, the antibody of the present invention is useful in the treatment, prevention, testing, and so forth for diseases associated with the CXADR protein, particularly treatment, prevention, testing, and so forth for cancers.

SEQUENCE LISTING FREE TEXT

SEQ ID NO: 1
<223> 6G10A light chain variable region CDR1
SEQ ID NO: 2
<223> 6G10A light chain variable region CDR2
SEQ ID NO: 3
<223> 6G10A light chain variable region CDR3
SEQ ID NO: 4
<223> 6G10A light chain variable region cDNA
SEQ ID NO: 6
<223> 6G10A heavy chain variable region CDR1
SEQ ID NO: 7
<223> 6G10A heavy chain variable region CDR2
SEQ ID NO: 8
<223> 6G10A heavy chain variable region CDR3
SEQ ID NO: 9
<223> 6G10A heavy chain variable region cDNA
SEQ ID NO: 11
<223> 7F8A light chain variable region CDR1
SEQ ID NO: 12
<223> 7F8A light chain variable region CDR2
SEQ ID NO: 13
<223> 7F8A light chain variable region CDR3
SEQ ID NO: 14
<223> 7F8A light chain variable region cDNA
SEQ ID NO: 16
<223> 7F8A heavy chain variable region CDR1
SEQ ID NO: 17
<223> 7F8A heavy chain variable region CDR2
SEQ ID NO: 18
<223> 7F8A heavy chain variable region CDR3
SEQ ID NO: 19
<223> 7F8A heavy chain variable region cDNA
SEQ ID NOs: 21 to 32
<223> Artificially synthesized primer sequences

The invention claimed is:

1. An antibody capable of binding to an epitope present at positions 181 to 230 of human CXADR protein, wherein said antibody is selected from the group consisting of (a) and (b):
   (a) an antibody comprising a light chain variable region and a heavy chain variable region, wherein the light chain variable region comprises complementarity determining regions (CDRs) 1 to 3 which comprise the amino acid sequences set forth in SEQ ID NOs: 1 to 3, respectively, and wherein the heavy chain variable region comprises CDRs 1 to 3 which comprise the amino acid sequences set forth in SEQ ID NOs: 6 to 8, respectively; and
   (b) an antibody comprising a light chain variable region and a heavy chain variable region, wherein the light chain variable region comprises CDRs 1 to 3 which comprise the amino acid sequences set forth in SEQ ID NOs: 11 to 13, respectively, and wherein the heavy chain variable region comprises CDRs 1 to 3 which comprise the amino acid sequences set forth in SEQ ID NOs: 16 to 18, respectively.

2. A pharmaceutical composition comprising the antibody according to claim 1 as an active ingredient, and a carrier.

3. A method for detecting the presence or absence of a human CXADR protein in a sample isolated from a patient who has cancer or who is suspected of having cancer, the method comprising reacting the sample with the antibody according to claim 1, and detecting whether the antibody binds to the human CXADR protein.

4. A method for treating CXADR-expressing cancer, comprising administering an effective amount of the antibody according to claim 1 to a patient in need of such treatment.

5. The antibody according to claim 1, wherein the light chain variable region of said antibody comprises the amino acid sequence set forth in SEQ ID NO: 5 from which a signal sequence is removed; or comprises the amino acid sequence set forth in SEQ ID NO: 5 from which a signal sequence is removed and wherein ten or fewer amino acids in the framework region are substituted, deleted, added, and/or inserted,
   and wherein the heavy chain variable region of said antibody comprises the amino acid sequence set forth in SEQ ID NO: 10 from which a signal sequence is removed; or comprises the amino acid sequence set forth in SEQ ID NO: 10 from which a signal sequence is removed and wherein ten or fewer amino acids in the framework region are substituted, deleted, added, and/or inserted.

6. The antibody according to claim 1, wherein the light chain variable region of said antibody comprises the amino acid sequence set forth in SEQ ID NO: 15 from which a signal sequence is removed; or comprises the amino acid sequence set forth in SEQ ID NO: 15 from which a signal sequence is removed and wherein ten or fewer amino acids in the framework region are substituted, deleted, added, and/or inserted,
   and wherein the heavy chain variable region of said antibody comprises the amino acid sequence set forth in SEQ ID NO: 20 from which a signal sequence is removed; or comprises the amino acid sequence set forth in SEQ ID NO: 20 from which a signal sequence is removed and wherein ten or fewer amino acids in the framework region are substituted, deleted, added, and/or inserted.

7. A method for treating CXADR-expressing cancer, comprising administering an effective amount of an antibody capable of binding to an epitope present at positions 181 to 230 of human CXADR protein to a patient in need of such treatment.

* * * * *

SEQUENCE LISTING

```
<160> NUMBER OF SEQ ID NOS: 32

<210> SEQ ID NO 1
<211> LENGTH: 11
<212> TYPE: PRT
<213> ORGANISM: Mus musculus
<220> FEATURE:
<221> NAME/KEY: SITE
<222> LOCATION: (1)..(11)
<223> OTHER INFORMATION: 6G10A Lv CDR1

<400> SEQUENCE: 1

Arg Ala Ser Glu Asn Ile Asp Ser Tyr Leu Ala
1               5                   10

<210> SEQ ID NO 2
<211> LENGTH: 7
<212> TYPE: PRT
<213> ORGANISM: Mus musculus
```

-continued

```
<220> FEATURE:
<221> NAME/KEY: SITE
<222> LOCATION: (1)..(7)
<223> OTHER INFORMATION: 6G10A Lv CDR2

<400> SEQUENCE: 2

Ala Ala Thr Leu Leu Ala Asp
1               5

<210> SEQ ID NO 3
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: 6G10A Lv CDR3

<400> SEQUENCE: 3

Gln His Tyr Tyr Ser Thr Pro Trp Thr
1               5

<210> SEQ ID NO 4
<211> LENGTH: 387
<212> TYPE: DNA
<213> ORGANISM: Mus musculus
<220> FEATURE:
<221> NAME/KEY: CDS
<222> LOCATION: (1)..(387)
<223> OTHER INFORMATION: 6G10A Lv cDNA

<400> SEQUENCE: 4 atg agt gtg ccc act cag ctc ctg ggg ttg ctg ctg ctg tgg ctt aca       48
Met Ser Val Pro Thr Gln Leu Leu Gly Leu Leu Leu Leu Trp Leu Thr
1               5                   10                  15 gat gcc aga tgt gac atc cag atg act cag tct cca gct tcc ctg tct       96
Asp Ala Arg Cys Asp Ile Gln Met Thr Gln Ser Pro Ala Ser Leu Ser
                20                  25                  30 gca tct gtg gga gaa act gtc acc atc aca tgt cga gca agt gag aat      144
Ala Ser Val Gly Glu Thr Val Thr Ile Thr Cys Arg Ala Ser Glu Asn
            35                  40                  45 att gac agt tat tta gca tgg tat cag cag aaa cag gga aaa tct cct      192
Ile Asp Ser Tyr Leu Ala Trp Tyr Gln Gln Lys Gln Gly Lys Ser Pro
        50                  55                  60 cag ctc ctg gtc tat gct gca aca ctc tta gca gat ggt gtg cca tca      240
Gln Leu Leu Val Tyr Ala Ala Thr Leu Leu Ala Asp Gly Val Pro Ser
65                  70                  75                  80 agg ttc agt ggc agt gga tca ggc aca cag tat tct ctc aag atc aac      288
Arg Phe Ser Gly Ser Gly Ser Gly Thr Gln Tyr Ser Leu Lys Ile Asn
                85                  90                  95 agc ctg cag tct gaa gat gtt gcg aga tat tac tgt caa cat tat tat      336
Ser Leu Gln Ser Glu Asp Val Ala Arg Tyr Tyr Cys Gln His Tyr Tyr
                100                 105                 110 agt act ccg tgg acg ttc ggt gga ggc acc aag ctg gaa atc aaa cgg      384
Ser Thr Pro Trp Thr Phe Gly Gly Gly Thr Lys Leu Glu Ile Lys Arg
            115                 120                 125 gct                                                                  387
Ala

<210> SEQ ID NO 5
<211> LENGTH: 129
<212> TYPE: PRT
<213> ORGANISM: Mus musculus
```

<400> SEQUENCE: 5

Met Ser Val Pro Thr Gln Leu Leu Gly Leu Leu Leu Trp Leu Thr
1               5                   10                  15

Asp Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Asp Ser Tyr Leu Ala Trp Tyr Gln Gln Lys Gln Gly Lys Ser Pro
    50                  55                  60

Gln Leu Leu Val Tyr Ala Ala Thr Leu Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Arg Tyr Tyr Cys Gln His Tyr Tyr
            100                 105                 110

Ser Thr Pro Trp Thr Phe Gly Gly Thr Lys Leu Glu Ile Lys Arg
        115                 120                 125

Ala

<210> SEQ ID NO 6
<211> LENGTH: 5
<212> TYPE: PRT
<213> ORGANISM: Mus musculus
<220> FEATURE:
<221> NAME/KEY: SITE
<222> LOCATION: (1)..(5)
<223> OTHER INFORMATION: 6G10A Hv CDR1

<400> SEQUENCE: 6

Ser Tyr Trp Ile Asn
1               5

<210> SEQ ID NO 7
<211> LENGTH: 17
<212> TYPE: PRT
<213> ORGANISM: Mus musculus
<220> FEATURE:
<221> NAME/KEY: SITE
<222> LOCATION: (1)..(17)
<223> OTHER INFORMATION: 6G10A Hv CDR2

<400> SEQUENCE: 7

Asn Ile Tyr Pro Gly Ser Ser Ser Thr Lys Tyr Asn Glu Lys Phe Lys
1               5                   10                  15

Ser

<210> SEQ ID NO 8
<211> LENGTH: 8
<212> TYPE: PRT
<213> ORGANISM: Mus musculus
<220> FEATURE:
<221> NAME/KEY: SITE
<222> LOCATION: (1)..(8)
<223> OTHER INFORMATION: 6G10A Hv CDR3

<400> SEQUENCE: 8

Gly Asp Gly Asp Tyr Phe Ala Asp
1               5

-continued

<210> SEQ ID NO 9
<211> LENGTH: 408
<212> TYPE: DNA
<213> ORGANISM: Mus musculus
<220> FEATURE:
<221> NAME/KEY: CDS
<222> LOCATION: (1)..(408)
<223> OTHER INFORMATION: 6G10A Hv cDNA

<400> SEQUENCE: 9

```
atg gga tgg agc tgt atc atc ctc tct ttg gta gca gca gct aca ggt      48
Met Gly Trp Ser Cys Ile Ile Leu Ser Leu Val Ala Ala Ala Thr Gly
1               5                   10                  15 gtc cac tcc cag gtc caa ctg cag cag cct ggt gct gaa ctt gtg aag      96
Val His Ser Gln Val Gln Leu Gln Gln Pro Gly Ala Glu Leu Val Lys
            20                  25                  30 cct ggg gcc tca gtg aag ctg tcc tgc aag gct tct ggc tac act ttc     144
Pro Gly Ala Ser Val Lys Leu Ser Cys Lys Ala Ser Gly Tyr Thr Phe
        35                  40                  45 acc agc tac tgg ata aac tgg gtg aag cag agg cct gga caa ggc ctt     192
Thr Ser Tyr Trp Ile Asn Trp Val Lys Gln Arg Pro Gly Gln Gly Leu
    50                  55                  60 gag tgg att gga aat att tat cct ggt agt agt agt act aag tac aat     240
Glu Trp Ile Gly Asn Ile Tyr Pro Gly Ser Ser Ser Thr Lys Tyr Asn
65                  70                  75                  80 gag aag ttc aag agc aag gcc aca ctg act gta gac aca tcc tcc agc     288
Glu Lys Phe Lys Ser Lys Ala Thr Leu Thr Val Asp Thr Ser Ser Ser
                85                  90                  95 aca gcc cac atg cag ctc agc agc ctg aca tct gac gac tct gcg gtc     336
Thr Ala His Met Gln Leu Ser Ser Leu Thr Ser Asp Asp Ser Ala Val
            100                 105                 110 tat tat tgt gca aag ggg gat ggt gac tac ttt gct gac tgg ggc caa     384
Tyr Tyr Cys Ala Lys Gly Asp Gly Asp Tyr Phe Ala Asp Trp Gly Gln
        115                 120                 125 ggg act ctg gtc act gtc tct gca                                     408
Gly Thr Leu Val Thr Val Ser Ala
    130                 135
```

<210> SEQ ID NO 10
<211> LENGTH: 136
<212> TYPE: PRT
<213> ORGANISM: Mus musculus

<400> SEQUENCE: 10

```
Met Gly Trp Ser Cys Ile Ile Leu Ser Leu Val Ala Ala Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Gly Ser Ser Ser Thr Lys Tyr Asn
65                  70                  75                  80

Glu Lys Phe Lys Ser Lys Ala Thr Leu Thr Val Asp Thr Ser Ser Ser
                85                  90                  95

Thr Ala His Met Gln Leu Ser Ser Leu Thr Ser Asp Asp Ser Ala Val
            100                 105                 110
```

```
              Tyr Tyr Cys Ala Lys Gly Asp Gly Asp Tyr Phe Ala Asp Trp Gly Gln
                      115                 120                 125

Gly Thr Leu Val Thr Val Ser Ala
                      130                 135

<210> SEQ ID NO 11
<211> LENGTH: 11
<212> TYPE: PRT
<213> ORGANISM: Mus musculus
<220> FEATURE:
<221> NAME/KEY: SITE
<222> LOCATION: (1)..(11)
<223> OTHER INFORMATION: 7F8A Lv CDR1

<400> SEQUENCE: 11

Arg Ala Ser Glu Asn Ile Asp Ser Tyr Leu Ala
1               5                   10

<210> SEQ ID NO 12
<211> LENGTH: 6
<212> TYPE: PRT
<213> ORGANISM: Mus musculus
<220> FEATURE:
<221> NAME/KEY: SITE
<222> LOCATION: (1)..(6)
<223> OTHER INFORMATION: 7F8A Lv CDR2

<400> SEQUENCE: 12

Ala Thr Leu Leu Ala Asp
1               5

<210> SEQ ID NO 13
<211> LENGTH: 9
<212> TYPE: PRT
<213> ORGANISM: Mus musculus
<220> FEATURE:
<221> NAME/KEY: SITE
<222> LOCATION: (1)..(9)
<223> OTHER INFORMATION: 7F8A Lv CDR3

<400> SEQUENCE: 13

Gln His Tyr Tyr Ser Thr Pro Leu Thr
1               5

<210> SEQ ID NO 14
<211> LENGTH: 387
<212> TYPE: DNA
<213> ORGANISM: Mus musculus
<220> FEATURE:
<221> NAME/KEY: CDS
<222> LOCATION: (1)..(387)
<223> OTHER INFORMATION: 7F8A Lv cDNA

<400> SEQUENCE: 14 atg agt gtg ccc act cag ctc ctg ggg ttg ctg ctg ctg tgg ctt aca        48
Met Ser Val Pro Thr Gln Leu Leu Gly Leu Leu Leu Leu Trp Leu Thr
1               5                   10                  15 gat gcc aga tgt gac atc cag atg act cag tct cca gct tcc ctg tct        96
Asp Ala Arg Cys Asp Ile Gln Met Thr Gln Ser Pro Ala Ser Leu Ser
                20                  25                  30 gca tct gtg gga gaa act gtc acc atc aca tgt cga gca agt gag aat       144
Ala Ser Val Gly Glu Thr Val Thr Ile Thr Cys Arg Ala Ser Glu Asn
            35                  40                  45 att gac agt tat tta gca tgg tat cag cag aaa cag gga aaa tct cct       192
Ile Asp Ser Tyr Leu Ala Trp Tyr Gln Gln Lys Gln Gly Lys Ser Pro
        50                  55                  60
```

```
cag ctc ctg gtc tat gct gca aca ctc tta gca gat ggt gtg cca tca   240
Gln Leu Leu Val Tyr Ala Ala Thr Leu Leu Ala Asp Gly Val Pro Ser
 65                  70                  75                  80 agg ttc agt ggc agt gga tca ggc aca cag tat tct ctc aag atc aac   288
Arg Phe Ser Gly Ser Gly Ser Gly Thr Gln Tyr Ser Leu Lys Ile Asn
                 85                  90                  95 agc ctg cag tct gaa gat gtt gcg aga tat tac tgt caa cat tat tat   336
Ser Leu Gln Ser Glu Asp Val Ala Arg Tyr Tyr Cys Gln His Tyr Tyr
            100                 105                 110 agt act cca ctc acg ttc ggt gct ggg acc aag ctg gag ctg aaa cgg   384
Ser Thr Pro Leu Thr Phe Gly Ala Gly Thr Lys Leu Glu Leu Lys Arg
        115                 120                 125 gct                                                                387
Ala

<210> SEQ ID NO 15
<211> LENGTH: 129
<212> TYPE: PRT
<213> ORGANISM: Mus musculus

<400> SEQUENCE: 15

Met Ser Val Pro Thr Gln Leu Leu Gly Leu Leu Leu Leu Trp Leu Thr
  1               5                  10                  15

Asp Ala Arg Cys Asp Ile Gln Met Thr Gln Ser Pro Ala Ser Leu Ser
             20                  25                  30

Ala Ser Val Gly Glu Thr Val Thr Ile Thr Cys Arg Ala Ser Glu Asn
         35                  40                  45

Ile Asp Ser Tyr Leu Ala Trp Tyr Gln Gln Lys Gln Gly Lys Ser Pro
     50                  55                  60

Gln Leu Leu Val Tyr Ala Ala Thr Leu Leu Ala Asp Gly Val Pro Ser
 65                  70                  75                  80

Arg Phe Ser Gly Ser Gly Ser Gly Thr Gln Tyr Ser Leu Lys Ile Asn
                 85                  90                  95

Ser Leu Gln Ser Glu Asp Val Ala Arg Tyr Tyr Cys Gln His Tyr Tyr
            100                 105                 110

Ser Thr Pro Leu Thr Phe Gly Ala Gly Thr Lys Leu Glu Leu Lys Arg
        115                 120                 125

Ala

<210> SEQ ID NO 16
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: 7F8A Hv CDR1

<400> SEQUENCE: 16

Asn Gly Asn His Trp Trp Asn
  1               5

<210> SEQ ID NO 17
<211> LENGTH: 16
<212> TYPE: PRT
<213> ORGANISM: Mus musculus
<220> FEATURE:
<221> NAME/KEY: SITE
<222> LOCATION: (1)..(16)
<223> OTHER INFORMATION: 7F8A Hv CDR2
```

```
<400> SEQUENCE: 17

Tyr Ile Asn Ser Ser Gly Ser Thr Asp Ser Asn Pro Ser Leu Lys Ser
1               5                   10                  15

<210> SEQ ID NO 18
<211> LENGTH: 7
<212> TYPE: PRT
<213> ORGANISM: Mus musculus
<220> FEATURE:
<221> NAME/KEY: SITE
<222> LOCATION: (1)..(7)
<223> OTHER INFORMATION: 7F8A Hv CDR3

<400> SEQUENCE: 18

Asp Asp Tyr Tyr Phe Asp Tyr
1               5

<210> SEQ ID NO 19
<211> LENGTH: 405
<212> TYPE: DNA
<213> ORGANISM: Mus musculus
<220> FEATURE:
<221> NAME/KEY: CDS
<222> LOCATION: (1)..(405)
<223> OTHER INFORMATION: 7F8A Hv cDNA

<400> SEQUENCE: 19 atg aga gtg ttg att ctt gtg tac ctg ttg aca gcc ctt cct ggt atc      48
Met Arg Val Leu Ile Leu Val Tyr Leu Leu Thr Ala Leu Pro Gly Ile
1               5                   10                  15 ttg tct gat gta cag ctt cag gag tca gga cct ggc ctg gtg aag cct      96
Leu Ser Asp Val Gln Leu Gln Glu Ser Gly Pro Gly Leu Val Lys Pro
                20                  25                  30 tct cag aca gtg tcc ctc acc tgc act gtc act ggc tac tct atc act     144
Ser Gln Thr Val Ser Leu Thr Cys Thr Val Thr Gly Tyr Ser Ile Thr
            35                  40                  45 aat ggt aat cac tgg tgg aac tgg atc cgg cag gtt tca gga agc aaa     192
Asn Gly Asn His Trp Trp Asn Trp Ile Arg Gln Val Ser Gly Ser Lys
        50                  55                  60 ctg gag tgg ata ggg tac att aac tcc agt ggt agc act gac agc aat     240
Leu Glu Trp Ile Gly Tyr Ile Asn Ser Ser Gly Ser Thr Asp Ser Asn
65                  70                  75                  80 cca tct ctc aaa agt cga atc tcc atc act aga gac act tcc aag aac     288
Pro Ser Leu Lys Ser Arg Ile Ser Ile Thr Arg Asp Thr Ser Lys Asn
                85                  90                  95 cag tta ttc ctg cag ttg aac tct gtg aca att gaa gat ata gcc aca     336
Gln Leu Phe Leu Gln Leu Asn Ser Val Thr Ile Glu Asp Ile Ala Thr
            100                 105                 110 tat tac tgt gca aga gat gat tac tac ttt gac tac tgg ggc caa ggc     384
Tyr Tyr Cys Ala Arg Asp Asp Tyr Tyr Phe Asp Tyr Trp Gly Gln Gly
        115                 120                 125 acc act ctc aca gtc tcc tca                                          405
Thr Thr Leu Thr Val Ser Ser
130                 135

<210> SEQ ID NO 20
<211> LENGTH: 135
<212> TYPE: PRT
<213> ORGANISM: Mus musculus
```

<400> SEQUENCE: 20

| Met | Arg | Val | Leu | Ile | Leu | Val | Tyr | Leu | Leu | Thr | Ala | Leu | Pro | Gly | Ile |
|---|---|---|---|---|---|---|---|---|---|---|---|---|---|---|---|
| 1 | | | | 5 | | | | | 10 | | | | | 15 | |

| Leu | Ser | Asp | Val | Gln | Leu | Gln | Glu | Ser | Gly | Pro | Gly | Leu | Val | Lys | Pro |
|---|---|---|---|---|---|---|---|---|---|---|---|---|---|---|---|
| | | | 20 | | | | | 25 | | | | | 30 | | |

| Ser | Gln | Thr | Val | Ser | Leu | Thr | Cys | Thr | Val | Thr | Gly | Tyr | Ser | Ile | Thr |
|---|---|---|---|---|---|---|---|---|---|---|---|---|---|---|---|
| | | 35 | | | | | 40 | | | | | 45 | | | |

| Asn | Gly | Asn | His | Trp | Trp | Asn | Trp | Ile | Arg | Gln | Val | Ser | Gly | Ser | Lys |
|---|---|---|---|---|---|---|---|---|---|---|---|---|---|---|---|
| | 50 | | | | | 55 | | | | | 60 | | | | |

| Leu | Glu | Trp | Ile | Gly | Tyr | Ile | Asn | Ser | Ser | Gly | Ser | Thr | Asp | Ser | Asn |
|---|---|---|---|---|---|---|---|---|---|---|---|---|---|---|---|
| 65 | | | | | 70 | | | | | 75 | | | | | 80 |

| Pro | Ser | Leu | Lys | Ser | Arg | Ile | Ser | Ile | Thr | Arg | Asp | Thr | Ser | Lys | Asn |
|---|---|---|---|---|---|---|---|---|---|---|---|---|---|---|---|
| | | | | 85 | | | | | 90 | | | | | 95 | |

| Gln | Leu | Phe | Leu | Gln | Leu | Asn | Ser | Val | Thr | Ile | Glu | Asp | Ile | Ala | Thr |
|---|---|---|---|---|---|---|---|---|---|---|---|---|---|---|---|
| | | | 100 | | | | | 105 | | | | | 110 | | |

| Tyr | Tyr | Cys | Ala | Arg | Asp | Asp | Tyr | Tyr | Phe | Asp | Tyr | Trp | Gly | Gln | Gly |
|---|---|---|---|---|---|---|---|---|---|---|---|---|---|---|---|
| | | 115 | | | | | 120 | | | | | 125 | | | |

| Thr | Thr | Leu | Thr | Val | Ser | Ser |
|---|---|---|---|---|---|---|
| | 130 | | | | 135 | |

<210> SEQ ID NO 21
<211> LENGTH: 40
<212> TYPE: DNA
<213> ORGANISM: Artificial Sequence
<220> FEATURE:
<223> OTHER INFORMATION: Artificially synthesized primer sequence

<400> SEQUENCE: 21
taatacgact cactataggg cgcgcagctg taaacggtag                     40

<210> SEQ ID NO 22
<211> LENGTH: 39
<212> TYPE: DNA
<213> ORGANISM: Artificial
<220> FEATURE:
<223> OTHER INFORMATION: Artificially synthesized primer sequence

<400> SEQUENCE: 22
attaaccctc actaaaggga gggggtggac catcctcta                      39

<210> SEQ ID NO 23
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 23
gtccacgagg tgctgcacaa t                                         21

<210> SEQ ID NO 24
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 24
gtcactggct cagggaaata acc                                       23

```
<210> SEQ ID NO 25
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 25
aagatggata cagttggtgc                                                20

<210> SEQ ID NO 26
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 26
tgtcaagagc ttcaacagga                                                20

<210> SEQ ID NO 27
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 27
ccggaattcc cacggcacgg cagccaccat gg                                  32

<210> SEQ ID NO 28
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 28
ttttcctttt gcggccgctc cagctttatt tgaaggaggg ac                       42

<210> SEQ ID NO 29
<211> LENGTH: 40
<212> TYPE: DNA
<213> ORGANISM: Artificial Sequence
<220> FEATURE:
<223> OTHER INFORMATION: Artificially synthesized primer sequence

<400> SEQUENCE: 29
ttttcctttt gcggccgcgg acaacgttta gacgcaacag                          40

<210> SEQ ID NO 30
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 30
ttttcctttt gcggccgctg agtcagacaa tttttgccac tc                       42

<210> SEQ ID NO 31
<211> LENGTH: 42
<212> TYPE: DNA
<213> ORGANISM: Artificial Sequence
<220> FEATURE:
<223> OTHER INFORMATION: Artificially synthesized primer sequence
```

```
<400> SEQUENCE: 31
ttttcctttt gcggccgcaa tcttcttatt tgcaacacca gg                      42

<210> SEQ ID NO 32
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 32
ttttcctttt gcggccgcgt agtcatcata aattttgtct cc                      42
```